(12) United States Patent
So

(10) Patent No.: US 10,799,501 B2
(45) Date of Patent: Oct. 13, 2020

(54) COMBINATION OF AN INHIBITOR OF PARP WITH AN INHIBITOR OF GSK-3 OR DOT1L

(71) Applicant: King's College London, London (GB)

(72) Inventor: Chi Wai Eric So, London (GB)

(73) Assignee: King's College Hospital NHS Foundation Trust, London (GB)

( * ) Notice: Subject to any disclaimer, the term of this patent is extended or adjusted under 35 U.S.C. 154(b) by 0 days.

(21) Appl. No.: 15/773,947

(22) PCT Filed: Nov. 4, 2016

(86) PCT No.: PCT/GB2016/053451
§ 371 (c)(1),
(2) Date: May 4, 2018

(87) PCT Pub. No.: WO2017/077326
PCT Pub. Date: May 11, 2017

(65) Prior Publication Data
US 2019/0076427 A1 Mar. 14, 2019

(30) Foreign Application Priority Data

Nov. 5, 2015 (GB) .................................. 1519573.8

(51) Int. Cl.
| | | |
|---|---|---|
| A61K 31/502 | (2006.01) | |
| A61K 45/06 | (2006.01) | |
| A61P 35/02 | (2006.01) | |
| A61K 31/404 | (2006.01) | |
| A61K 31/4184 | (2006.01) | |
| A61K 31/519 | (2006.01) | |
| A61K 31/7076 | (2006.01) | |
| A61K 33/00 | (2006.01) | |

(52) U.S. Cl.
CPC .......... *A61K 31/502* (2013.01); *A61K 31/404* (2013.01); *A61K 31/4184* (2013.01); *A61K 31/519* (2013.01); *A61K 31/7076* (2013.01); *A61K 33/00* (2013.01); *A61K 45/06* (2013.01); *A61P 35/02* (2018.01)

(58) Field of Classification Search
CPC .............. A61K 31/404; A61K 31/4184; A61K 31/502; A61K 31/7076; A61K 33/00; A61K 31/7064; A61K 31/519; A61K 45/06; A61K 2300/00; A61P 35/02
See application file for complete search history.

(56) References Cited

U.S. PATENT DOCUMENTS

| | | |
|---|---|---|
| 5,587,384 A | 12/1996 | Zhang et al. |
| 6,426,415 B1 | 7/2002 | Jackson et al. |
| 6,444,676 B1 | 9/2002 | Pang et al. |
| 6,476,048 B1 | 11/2002 | Szabo et al. |
| 6,514,983 B1 | 2/2003 | Li et al. |
| 6,635,642 B1 | 10/2003 | Jackson et al. |
| 6,828,319 B2 | 12/2004 | Jagtap et al. |
| 6,903,101 B1 | 6/2005 | Dumas et al. |
| 6,924,284 B2 | 8/2005 | Beaton et al. |
| 6,964,960 B2 | 11/2005 | Zimmermann et al. |
| 6,989,388 B2 | 1/2006 | Pellicciari et al. |
| 7,041,675 B2 | 5/2006 | Lubisch et al. |
| 7,087,637 B2 | 8/2006 | Grandel et al. |
| 2004/0254372 A1 | 12/2004 | Xu et al. |
| 2005/0148575 A1 | 7/2005 | Ferraris et al. |
| 2006/0003987 A1 | 1/2006 | Ferraris et al. |
| 2006/0004028 A1 | 1/2006 | Shiromizu et al. |
| 2006/0063926 A1 | 3/2006 | Ma et al. |
| 2006/0094743 A1 | 5/2006 | Fujio et al. |
| 2006/0094746 A1 | 5/2006 | Pellicciari et al. |

(Continued)

FOREIGN PATENT DOCUMENTS

| | | |
|---|---|---|
| EP | 412848 A2 | 2/1991 |
| EP | 453210 A2 | 10/1991 |

(Continued)

OTHER PUBLICATIONS

Grimwade (The Am Soc. of Hematology, 2000, 96, 4, Blood, p. 1297-1308) (Year: 2000).*
Faraoni et al. (Biochimica et Blophysica Acta, 2015, 462-472) (Year: 2015).*
Gardini et al. (PLos Genetics, 4, 11, p. 1-12, Nov. 2008) (Year: 2008).*
Flandrin (Classification of acute myeloid leukemias, Atlas of Genetics and Cytogenetics in Oncology and Haematology, Oct. 1, 2002). (Year: 2002).*
Daigle et al. (Blood, Aug. 2013, 122, 6, 2013) (Year: 2013).*
Alcalay et al., Acute myeloid leukemia fusion proteins deregulate genes involved in stem cell maintenance and DNA repair, *J. Clin. Invest.* 112:1751-61 (2003).

(Continued)

*Primary Examiner* — Umamaheswari Ramachandran
(74) *Attorney, Agent, or Firm* — Marshall, Gerstein & Borun LLP

(57) ABSTRACT

Provided herein is a pharmaceutical combination comprising (a) a poly-(ADP-ribose)-polymerase (PARP) inhibitor and (b) a second agent comprising (i) an inhibitor of glycogen synthase kinase 3 (GSK-3) or (ii) an inhibitor of disrupter of telomeric silencing 1-like (DOT1L). Also provided is a method of treating a subject suffering from acute myeloid leukaemia, comprising administering to the subject a therapeutically effective amount of the pharmaceutical combination. There is also described herein a method for selecting a therapy for a subject suffering from acute myeloid leukaemia, comprising determining whether a chromosomal abnormality at 11q23 is present in a sample obtained from the subject; wherein if the chromosomal abnormality at 11q23 is present in the sample, a therapy comprising combined administration of (a) a poly-(ADP-ribose)-polymerase (PARP) inhibitor and (b) a second agent comprising (i) an inhibitor of glycogen synthase kinase 3 (GSK-3) or (ii) an inhibitor of disrupter of telomeric silencing 1-like (DOT1L) is selected for the subject.

10 Claims, 57 Drawing Sheets

Specification includes a Sequence Listing.

(56) References Cited

U.S. PATENT DOCUMENTS

| | | |
|---|---|---|
| 2006/0229289 A1 | 10/2006 | Zhu et al. |
| 2006/0229351 A1 | 10/2006 | Zhu et al. |
| 2007/0015814 A1 | 1/2007 | Kun et al. |
| 2007/0032489 A1 | 2/2007 | Weintraub et al. |
| 2007/0072841 A1 | 3/2007 | Helleday et al. |
| 2007/0072842 A1 | 3/2007 | Dominique et al. |
| 2007/0072912 A1 | 3/2007 | Hideg et al. |
| 2007/0105118 A1* | 5/2007 | Dugas ................ C12Q 1/6886 435/6.12 |
| 2010/0011921 A1* | 1/2010 | Dall .................. A61B 17/8863 83/13 |
| 2016/0346306 A1* | 12/2016 | Rassool ............... A61K 31/145 |

FOREIGN PATENT DOCUMENTS

| | | |
|---|---|---|
| EP | 454831 A1 | 11/1991 |
| EP | 879820 A1 | 11/1998 |
| EP | 1212328 A1 | 6/2002 |
| EP | 1582520 A1 | 10/2005 |
| EP | 03/007959 A1 | 4/2016 |
| WO | WO-1991/007404 A1 | 5/1991 |
| WO | WO-1995/024379 A1 | 9/1995 |
| WO | WO-2000/042025 A1 | 7/2000 |
| WO | WO-2001/012199 A2 | 2/2001 |
| WO | WO-2001/016136 A2 | 3/2001 |
| WO | WO-2001/16137 A1 | 3/2001 |
| WO | WO-2001/021615 A1 | 3/2001 |
| WO | WO-2001/023390 A2 | 4/2001 |
| WO | WO-2001/057038 A1 | 8/2001 |
| WO | WO-2001/079184 A1 | 10/2001 |
| WO | WO-2001/085686 A2 | 11/2001 |
| WO | WO-2001/085687 A1 | 11/2001 |
| WO | WO-2001/090077 A1 | 11/2001 |
| WO | WO-2002/36576 A1 | 5/2002 |
| WO | WO-2002/044157 A2 | 6/2002 |
| WO | WO-2002/068407 A1 | 9/2002 |
| WO | WO-2002/094790 A1 | 11/2002 |
| WO | WO-03/0805 A1 | 1/2003 |
| WO | WO-2003/004472 A1 | 1/2003 |
| WO | WO-2003/051879 A1 | 6/2003 |
| WO | WO-03/057145 A2 | 7/2003 |
| WO | WO-2003/055492 A1 | 7/2003 |
| WO | WO-2003/057699 A1 | 7/2003 |
| WO | WO-2003/082853 A1 | 10/2003 |
| WO | WO-2004/018455 A1 | 3/2004 |
| WO | WO-2004/037791 A1 | 5/2004 |
| WO | WO-2004/048339 A1 | 6/2004 |
| WO | WO-2004/080976 A1 | 9/2004 |
| WO | WO-2004/087713 A1 | 10/2004 |
| WO | WO-2004/096779 A1 | 11/2004 |
| WO | WO-2004/105700 A2 | 12/2004 |
| WO | WO-2004/108723 A1 | 12/2004 |
| WO | WO-2005/012305 A2 | 2/2005 |
| WO | WO-2005/023246 A1 | 3/2005 |
| WO | WO-2005/023800 A1 | 3/2005 |
| WO | WO-2005/054201 A1 | 6/2005 |
| WO | WO-2005/054209 A1 | 6/2005 |
| WO | WO-2005/054210 A1 | 6/2005 |
| WO | WO-2005/058843 A1 | 6/2005 |
| WO | WO-2005/0080096 A2 | 9/2005 |
| WO | WO-2005/097750 A1 | 10/2005 |
| WO | WO-2005/108400 A1 | 11/2005 |
| WO | WO-2005/112935 A1 | 12/2005 |
| WO | WO-2005/123687 A1 | 12/2005 |
| WO | WO-2006/001754 A1 | 1/2006 |
| WO | WO-2006/003146 A1 | 1/2006 |
| WO | WO-2006/003147 A1 | 1/2006 |
| WO | WO-2006/003148 A1 | 1/2006 |
| WO | WO-2006/003150 A1 | 1/2006 |
| WO | WO-2006/008118 A1 | 1/2006 |
| WO | WO-2006/008119 A1 | 1/2006 |
| WO | WO-2006/033006 A2 | 3/2006 |
| WO | WO-2006/033007 A2 | 3/2006 |
| WO | WO-2006/042638 A1 | 4/2006 |
| WO | WO-2006/046035 A1 | 5/2006 |
| WO | WO-2006/065392 A2 | 6/2006 |
| WO | WO-2006/066172 A1 | 6/2006 |
| WO | WO-2006/078503 A2 | 7/2006 |
| WO | WO-2006/078711 A2 | 7/2006 |
| WO | WO-2006/135873 A2 | 12/2006 |
| WO | WO-2006/137510 A1 | 12/2006 |
| WO | WO-2007/0011962 A2 | 1/2007 |
| WO | WO-07/040440 A1 | 4/2007 |
| WO | WO-2007/040436 A1 | 4/2007 |
| WO | WO-2007/040438 A2 | 4/2007 |
| WO | WO-2007/040439 A1 | 4/2007 |
| WO | WO-2007/041357 A1 | 4/2007 |
| WO | WO-08/002244 A2 | 1/2008 |
| WO | WO-08/002245 A2 | 1/2008 |
| WO | WO-2011/029054 A1 | 3/2011 |
| WO | WO-2012/166151 A1 | 12/2012 |
| WO | WO-2014/026198 A1 | 2/2014 |
| WO | WO-2014/035140 A2 | 3/2014 |
| WO | WO-2014/039839 A1 | 3/2014 |
| WO | WO-2014/100662 A1 | 6/2014 |
| WO | WO-2014/127191 A1 | 8/2014 |
| WO | WO-2014/152562 A1 | 9/2014 |
| WO | WO-2014/153001 A1 | 9/2014 |
| WO | WO-2014/164543 A1 | 10/2014 |
| WO | WO-2014/200479 A1 | 12/2014 |
| WO | WO-2015/013256 A1 | 1/2015 |
| WO | WO-2015/017863 A1 | 2/2015 |
| WO | WO-2015/040378 A1 | 3/2015 |
| WO | WO-2015/073706 A1 | 5/2015 |
| WO | WO-2015/112598 A2 | 7/2015 |
| WO | WO-2015/134603 A2 | 9/2015 |
| WO | WO-2016/043874 A2 | 3/2016 |

OTHER PUBLICATIONS

Anglin et al., Synthesis and structure-activity relationship investigation of adenosine-containing inhibitors of histone methyltransferase DOT1L, *J. Med. Chem.* 55:8066-74 (2012).

Armstrong et al., MLL translocations specify a distinct gene expression profile that distinguishes a unique leukemia, *Nat. Genet.* 30:41-47 (2002).

Arteaga et al., The histone demethylase PHF8 governs retinoic acid response in acute promyelocytic leukemia, *Cancer Cell.* 23:376-89 (2013).

Ayton et al., Binding to nonmethylated CpG DNA is essential for target recognition, transactivation, and myeloid transformation by an MLL oncoprotein, *Mol. Cell Biol.* 24:10470-8 (2004).

Ayton et al., Transformation of myeloid progenitors by MLL oncoproteins is dependent on Hoxa7 and Hoxa9, *Genes Dev.* 17:2298-307 (2003).

Banasik et al., Inhibitors and activators of ADP-ribosylation reactions, *Mol. Cell Biochem.* 138:185-97 (1994).

Banasik et al., Specific inhibitors of poly(ADP-ribose) synthetase and mono(ADP-ribosyl)transferase, *J. Biol. Chem.* 267:1569-75 (1992).

Basavapathruni et al., Conformational adaptation drives potent, selective and durable inhibition of the human protein methyltransferase DOT1L, *Chem. Biol. Drug Des.* 80:971-80 (2012).

Baumann et al., Human Rad51 protein promotes ATP-dependent homologous pairing and strand transfer reactions in vitro, *Cell.* 87:757-66 (1996).

Bitoun et al., The mixed-lineage leukemia fusion partner AF4 stimulates RNA polymerase II transcriptional elongation and mediates coordinated chromatin remodeling, *Hum. Mol. Genet.* 16:92-106 (2007).

Blanpain et al., DNA-damage response in tissue-specific and cancer stem cells, *Cell Stem Cell.* 8:16-29 (2011).

Boichuk et al., Functional connection between Rad51 and PML in homology-directed repair, *PLoS One.* 6:e25814 (2011).

Borkin et al., Pharmacologic inhibition of the Menin-MLL interaction blocks progression of MLL leukemia in vivo, *Cancer Cell.* 27:589-602 (2015).

Brightwell et al., Poly(adenosine diphosphate ribose) polymerase in Physarum polycephalum nuclei, *Biochem. J.* 125:67P (1971).

(56) References Cited

OTHER PUBLICATIONS

Bryant et al., PARP is activated at stalled forks to mediate Mre11-dependent replication restart and recombination, *EMBO J.* 28:2601-15 (2009).
Bryant et al., Specific killing of BRCA2-deficient tumours with inhibitors of poly(ADP-ribose) polymerase, *Nature.* 434:913-7 (2005).
Calvert et al., The clinical development of inhibitors of poly(ADP-ribose) polymerase, *Ann. Oncol. Suppl.* 1:i53-9 (2011).
Carreira et al., The BRC repeats of BRCA2 modulate the DNA-binding selectivity of RAD51, *Cell.* 136:1032-43 (2009).
Chen et al., Targeting DOT1L and HOX gene expression in MLL-rearranged leukemia and beyond, *Exp. Hermatol.* 43:673-84 (2015).
Cheung et al., Transcriptional and epigenetic networks in haematological malignancy, *FEBS Lett.* 585:2100-11 (2011).
Chiba et al., Homeobox B9 induces epithelial-to-mesenchymal transition-associated radioresistance by accelerating DNA damage responses, *Proc. Natl. Acad. Sci. USA.* 109:2760-5 (2012).
Choi et al., Axin1 expression facilitates cell death induced by aurora kinase inhibition through PARP activation, *J. Cell. Biochem.* 112:2392-402 (2011).
Coghlan et al., Selective small molecule inhibitors of glycogen synthase kinase-3 modulate glycogen metabolism and gene transcription, *Chem. Biol.* 7:793-803 (2000).
Cohen et al., GSK3 inhibitors: development and therapeutic potential, *Nat. Rev. Drug Discov.* 3:479-87 (2004).
Cosi, New inhibitors of ply(ADP-ribose) polymerase and their potential therapeutic targets, *Expert Opin. Ther. Patents.* 12: 1047-1071 (2002).
Costa et al., Reversing HOXA9 oncogene activation by PI3K inhibition: epigenetic mechanism and prognostic significance in human glioblastoma, *Cancer Res.* 70:453-62 (2010).
Daigle et al., Potent inhibition of DOT1L as treatment of MLL-fusion leukemia, *Blood.* 122:1017-25 (2013).
Daigle et al., Selective killing of mixed lineage leukemia cells by a potent small-molecule DOT1L inhibitor, *Cancer Cell.* 20:53-65 (2011).
De Lorenzo et al., The Elephant and the Blind Men: Making Sense of PARP Inhibitors in Homologous Recombination Deficient Tumor Cells, *Front. Oncol.* 3:228 (2013).
Deng et al., Synthesis, Activity and Metabolic Stability of Non-Ribose Containing Inhibitors of Histone Methyltransferase DOT1L, *Medchemcomm.* 4:822-826 (2013).
Dimri et al., A biomarker that identifies senescent human cells in culture and in aging skin in vivo, *Proc. Natl. Acad. Sci. USA.* 92:9363-7 (1995).
Dorrance et al., Mll partial tandem duplication induces aberrant Hox expression in vivo via specific epigenetic alterations, *J. Clin. Invest.* 116:2707-16 (2006).
El-Khamisy et al., A requirement for PARP-1 for the assembly or stability of XRCC1 nuclear foci at sites of oxidative DNA damage, *Nucleic Acids Red.* 31:5526-33 (2003).
Eldar-Finkelman et al., GSK-3 Inhibitors: Preclinical and Clinical Focus on CNS, *Front Mol. Neurosci.* 4:32 (2011).
Esposito et al., Synthetic lethal targeting of oncogenic transcription factors in acute leukemia by PARP inhibitors, *Nat. Med.* 21:1481-90 (2015).
Esposito et al., DNA damage accumulation and repair defects in acute myeloid leukemia: implications for pathogenesis, disease progression, and chemotherapy resistance, *Chromosoma.* 123:545-61 (2014).
Faber et al., HOXA9 is required for survival in human MLL-rearranged acute leukemias, *Blood.* 113:2375-85 (2009).
Farmer et al., Targeting the DNA repair defect in BRCA mutant cells as a therapeutic strategy, *Nature.* 434:917-21 (2005).
Feng et al., Methylation of H3-lysine 79 is mediated by a new family of HMTases without a SET domain, *Curr. Biol.* 12:1052-8 (2002).
Fong et al., Inhibition of poly(ADP-ribose) polymerase in tumors from BRCA mutation carriers, *N. Engl. J. Med.* 36:123-34 (2009).

Fung et al., Overcoming treatment resistance in acute promyelocytic leukemia and beyond, *Oncotarget.* 4:1128-9 (2013).
Gaspar et al., MGMT-independent temozolomide resistance in pediatric glioblastoma cells associated with a PI3-kinase-mediated HOX/stem cell gene signature, *Cancer Res.* 70:9243-52 (2010).
Gautier et al., affy—analysis of Affymetrix GeneChip data at the probe level, *Bioinformatics.* 20:307-15 (2004).
Gaymes et al., Increased error-prone non homologous DNA end-joining—a proposed mechanism of chromosomal instability in Bloom's syndrome, *Oncogene.* 21:2525-33 (2002).
Gaymes et al., Myeloid leukemias have increased activity of the nonhomologous end-joining pathway and concomitant DNA misrepair that is dependent on the Ku70/86 heterodimer, *Cancer Res.* 62:2791-7 (2002).
GEO accession: GSE115932, RRBS in Smchd1 control and Smchd1 deleted male and female neural stem cells, Jun. 30, 2018.
GEO accession: GSE6891, Acute myeloid leukemia samples of samples =< 60yrs on HG-U133 plus 2, Mar. 12, 2008.
Golub et al., Molecular classification of cancer: class discovery and class prediction by gene expression monitoring, *Science.* 286:531-7 (1999).
Grembecka et al., Menin-MLL inhibitors reverse oncogenic activity of MLL fusion proteins in leukemia, *Nat. Chem. Biol.* 8:277-84 (2012).
Guenther et al., Aberrant chromatin at genes encoding stem cell regulators in human mixed-lineage leukemia, *Genes Dev.* 22:3403-8 (2008).
Haince et al., Ataxia telangiectasia mutated (ATM) signaling network is modulated by a novel poly(ADP-ribose)-dependent pathway in the early response to DNA-damaging agents, *J. Biol. Chem.* 282:16441-53 (2007).
Haince et al., PARP1-dependent kinetics of recruitment of MRE11 and NBS1 proteins to multiple DNA damage sites, *J. Biol. Chem.* 283:1197-208 (2008).
Helleday et al., DNA repair pathways as targets for cancer therapy, *Nat. Rev. Cancer.* 8:193-204 (2008).
Helleday, The underlying mechanism for the PARP and BRCA synthetic lethality: clearing up the misunderstandings, *Mol Oncol.* 5:387-93 (2011).
Hess et al., c-Myb is an essential downstream target for homeobox-mediated transformation of hematopoietic cells, *Blood.* 108:297-304 (2006).
Hess, MLL: a histone methyltransferase disrupted in leukemia, *Trends Mol. Med.* 10:500-7 (2004).
Huang et al., Identification and characterization of Hoxa9 binding sites in hematopoietic cells, *Blood.* 119:388-98 (2012).
International Preliminary Report on Patentability, PCT/GB2016/053451 (dated May 8, 2018).
International Search Report and Written Opinion, PCT/GB2016/053451 (dated Feb. 13, 2017).
Izon et al., Loss of function of the homeobox gene Hoxa-9 perturbs early T-cell development and induces apoptosis in primitive thymocytes, *Blood.* 92:383-93 (1998).
Kawagoe et al., Expression of HOX genes, HOX cofactors, and MLL in phenotypically and functionally defined subpopulations of leukemic and normal human hematopoietic cells, *Leukemia.* 13:687-98 (1999).
Kramer et al., Small-Molecule Inhibitors of GSK-3: Structural Insights and Their Application to Alzheimer's Disease Models, *Int. J. Alzheimers Dis.* 2012:381029 (2012).
Kraus, Transcriptional control by PARP-1: chromatin modulation, enhancer-binding, coregulation, and insulation, *Curr. Opin. Cell Biol.* 20:294-302 (2008).
Krishnakumar et al., The PARP side of the nucleus: molecular actions, physiological outcomes, and clinical targets, *Mol. Cel.* 39:8-24 (2010).
Krivtsov et al., MLL translocations, histone modifications and leukemia stem-cell development, *Nat. Rev. Cancer.* 7:823-33 (2007).
Kumar et al., Hoxa9 influences the phenotype but not the incidence of Mll-AF9 fusion gene leukemia, *Blood.* 103:1823-8 (2004).
Lawrence et al., Loss of expression of the Hoxa-9 homeobox gene impairs the proliferation and repopulating ability of hematopoietic stem cells, *Blood.* 106:3988-94 (2005).

(56) References Cited

OTHER PUBLICATIONS

Li et al., A SALL4/MLL/HOXA9 pathway in murine and human myeloid leukemogenesis, *J. Clin. Invest.* 123:4195-207 (2013).
Liu et al., Phosphorylation of MLL by ATR is required for execution of mammalian S-phase checkpoint, *Nature.* 467:343-6 (2010).
Mah et al., gammaH2AX: a sensitive molecular marker of DNA damage and repair, *Leukemia.* 24:679-86 (2010).
Martin et al., Interplay between Homeobox proteins and Polycomb repressive complexes in p16INK[4]a regulation, *EMBO J.* 32:982-95 (2013).
Masson et al., XRCC1 is specifically associated with poly(ADP-ribose) polymerase and negatively regulates its activity following DNA damage, *Mol. Cell Biol.* 18:3563-71 (1998).
McLoran et al., Applying synthetic lethality for the selective targeting of cancer, *N. Engl. J. Med.* 371:1725-35 (2014).
Miknyoczki et al., The selective poly(ADP-ribose) polymerase-1(2) inhibitor, CEP-8983, increases the sensitivity of chemoresistant tumor cells to temozolomide and irinotecan but does not potentiate myelotoxicity, *Mol. Cancer Ther.* 6:2290-302 (2007).
Milne et al., Leukemogenic MLL fusion proteins bind across a broad region of the Hox a9 locus, promoting transcription and multiple histone modifications, *Cancer Res.* 65:11367-74 (2005).
Milne et al., MLL targets SET domain methyltransferase activity to Hox gene promoters, *Mol. Cell.* 10:1107-17 (2002).
Mohan et al., Linking H3K79 trimethylation to Wnt signaling through a novel Dot1-containing complex (DotCom), *Genes Dev.* 24:574-89 (2010).
Monroe et al., MLL-AF9 and MLL-ENL alter the dynamic association of transcriptional regulators with genes critical for leukemia, *Exp. Hematol.* 39:77-86 (2011).
Moynahan et al., Mitotic homologous recombination maintains genomic stability and suppresses tumorigenesis, *Nat. Rev. Mol. Cell Biol.* 11:196-207 (2010).
Mueller et al., A role for the MLL fusion partner ENL in transcriptional elongation and chromatin modification, *Blood.* 110:4445-54 (2007).
Mueller et al., Misguided transcriptional elongation causes mixed lineage leukemia, *PLoS Biol.* 7:e1000249 (2009).
Nakamura et al., ALL-1 is a histone methyltransferase that assembles a supercomplex of proteins involved in transcriptional regulation, *Mol. Cell.* 10:1119-28 (2002).
Nieborowska-Skorska et al, Oncogene-Induced DNA repair defects promote PARP1-Mediated "Dual Synthetic Lethality" to eradicate quiescent and proliferating leukemia stem and progenitor cells, *Blood Journal.* 122:810 (2013).
Okada et al., hDOT1L links histone methylation to leukemogenesis, *Cell.* 121:167-78 (2005).
Paddock et al., Competition between PARP-1 and Ku70 control the decision between high-fidelity and mutagenic DNA repair, *DNA Repair (Amst).* 10:338-43 (2011).
Park et al., Characterization of the DOT1L network: implications of diverse roles for DOT1L, *Protein J.* 29:213-23 (2010).
Penning, Small-molecule PARP modulators—current status and future therapeutic potential, *Curr. Opin. Drug Discov. Devel.* 13:577-86 (2010).
Pierce et al., XRCC3 promotes homology-directed repair of DNA damage in mammalian cells, *Genes Dev.* 13:2633-8 (1999).
Rouleau et al., PARP inhibition:PARP1 and beyond, *Nat. Rev. Cancer.* 10:293-301 (2010).
Roy et al., BRCA1 and BRCA2: different roles in a common pathway of genome protection, *Nat. Rev. Cancer.* 12:68-78 (2011).
Rubin et al., A role for the HOXB7 homeodomain protein in DNA repair, *Cancer Res.* 67:1527-35 (2007).
Santos et al., DNA-damage-induced differentiation of leukaemic cells as an anti-cancer barrier, *Nature.* 514:107-11 (2014).
Schmittgen et al., Analyzing real-time PCR data by the comparative C(T) method, *Nat. Protoc.* 3:1101-8 (2008).
Slany et al., The molecular biology of mixed lineage leukemia, *Haematologica.* 94:984-93 (2009).
Slany et al., The oncogenic capacity of HRX-ENL requires the transcriptional transactivation activity of ENL and the DNA binding motifs of HRX, *Mol. Cell. Biol.* 18:122-9 (1998).
Smith et al., Functional crosstalk between Bmi1 and MLL/Hoxa9 axis in establishment of normal hematopoietic and leukemic stem cells, *Cell Stem Cell.* 8:649-62 (2011).
So et al., Dimerization contributes to oncogenic activation of MLL chimeras in acute leukemias, *Cancer Cell.* 4:99-110 (2003).
So et al., Leukemic transformation of hematopoietic progenitors by MLL-GAS7 in the absence of Hoxa7 or Hoxa9, *Blood.* 103:3192-9 (2004).
So et al., MLL-GAS7 transforms multipotent hematopoietic progenitors and induces mixed lineage leukemias in mice, *Cancer Cell.* 3:161-71 (2003).
Southan et al., Poly(ADP-ribose) polymerase inhibitors, *Curr. Med. Chem.* 14:321-40 (2003).
Steger et al., DOT1L/KMT4 recruitment and H3K79 methylation are ubiquitously coupled with gene transcription in mammalian cells, *Mol. Cell Biol.* 28:2825-39 (2008).
Takacova et al., DNA damage response and inflammatory signaling limit the MLL-ENL-induced leukemogenesis in vivo, *Cancer cell.* 21:517-31 (2012).
Thiel et al., MLL-AF9-induced leukemogenesis requires coexpression of the wild-type Mll allele, *Cancer Cell.* 17:148-59 (2010).
Turner et al., Hallmarks of 'BRCAness' in sporadic cancers, *Nat. Rev. Cancer.* 4:814-9 (2004).
Tutt et al., Oral poly(ADP-ribose) polymerase inhibitor olaparib in patients with BRCA1 or BRCA2 mutations and advanced breast cancer: a proof-of-concept trial, *Lancet.* 376:235-44 (2010).
Utsch et al., A novel stable polyalanine [poly(A)] expansion in the HOXA13 gene associated with hand-foot-genital syndrome: proper function of poly(A)-harbouring transcription factors depends on a critical repeat length? *Hum. Genet.* 110:488-94 (2002).
Valk et al., Prognostically useful gene-expression profiles in acute myeloid leukemia, *N. Engl. J. Med.* 350:1617-28 (2004).
Verhaak et al., Prediction of molecular subtypes in acute myeloid leukemia based on gene expression profiling, *Haematologica.* 94:131-4 (2009).
Viale et al., Cell-cycle restriction limits DNA damage and maintains self-renewal of leukaemia stem cells, *Nature.* 457:51-6 (2009).
Wahlberg et al., Family-wide chemical profiling and structural analysis of PARP and tankyrase inhibitors, *Nat. Biotechnol.* 30:283-8 (2012).
Wang et al., Glycogen synthase kinase 3 in MLL leukaemia maintenance and targeted therapy, *Nature.* 455:1205-9 (2008).
Wang et al., GSK-3 promotes conditional association of CREB and its coactivators with MEIS1 to facilitate HOX-mediated transcription and oncogenesis, *Cancer Cell.* 17:597-608 (2010).
Woodgett, A common denominator linking glycogen metabolism, nuclear oncogenes and development, *Trends Biochem. Sci.* 16:177-81 (1991).
Yeung et al., Beta-Catenin mediates the establishment and drug resistance of MLL leukemia stem cells, *Cancer Cell.* 18:606-18 (2010).
Yeung et al., Identification and characterization of hematopoietic stem and progenitor cell populations in mouse bone marrow by flow cytometry, *Methods Mol. Biol.* 538:301-15.
Yeung et al., Promyelocytic leukemia nuclear bodies support a late step in DNA double-strand break repair by homologous recombination. *J. Cell Biochem* (2011).
Yip et al., Mixed lineage leukemia protein in normal and leukemic stem cells, *Exp. Biol. Med. (Maywood).* 238:315-23 (2013).
Yokoyama et al., A higher-order complex containing AF4 and ENL family proteins with P-TEFb facilitates oncogenic and physiologic MLL-dependent transcription, *Cancer Cell.* 17:198-212 (2010).
Zeisig et al., Retroviral/Lentiviral transduction and transformation assay, *Methods Mol. Biol.* 538:207-229 (2009).
Zeisig et al., SnapShot: Acute myeloid leukemia, *Cancer Cell.* 22:698 (2012).
Zeleznik-Le et al., 11q23 translocations split the "AT-hook" cruciform DNA-binding region and the transcriptional repression domain from the activation domain of the mixed-lineage leukemia (MLL) gene, *Proc. Natl. Acad. Sci. USA.* 91:10610-4 (1994).

(56) References Cited

OTHER PUBLICATIONS

Zhang et al., Dot1a-AF9 complex mediates histone H3 Lys-79 hypermethylation and repression of ENaCalpha in an aldosterone-sensitive manner, *J. Biol. Chem.* 281:18059-68 (2006).
Zhong et al., A role for PML and the nuclear body in genomic stability, *Oncogene.* 18:7941-7 (1999).

\* cited by examiner

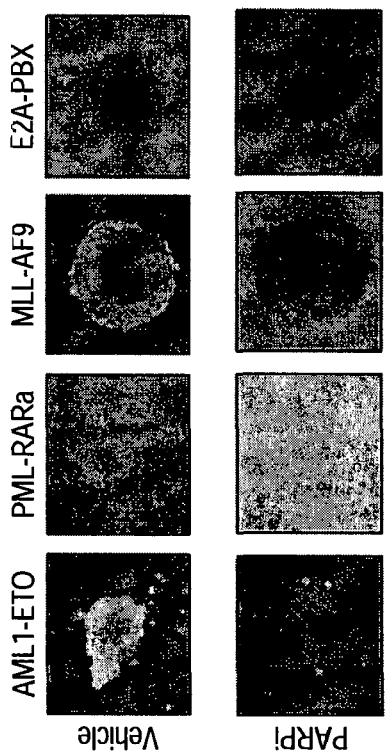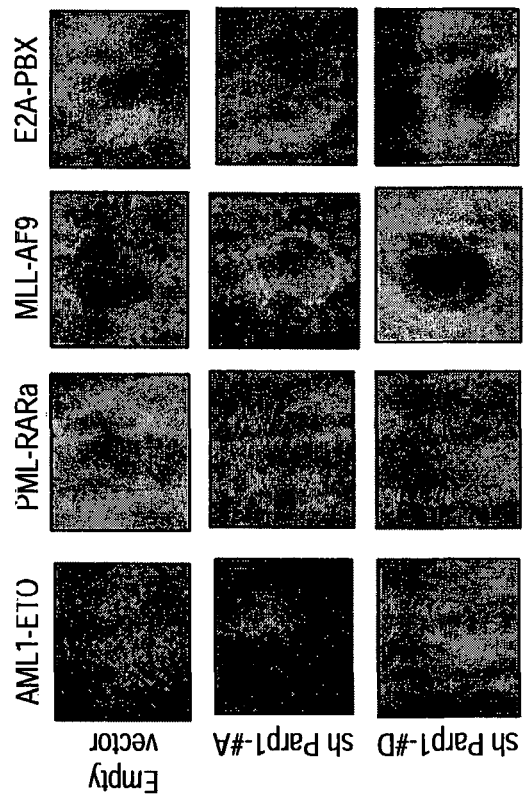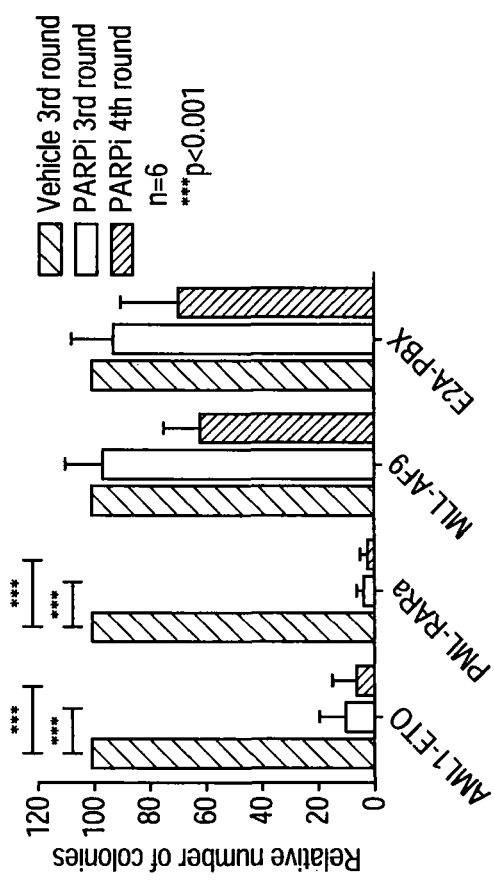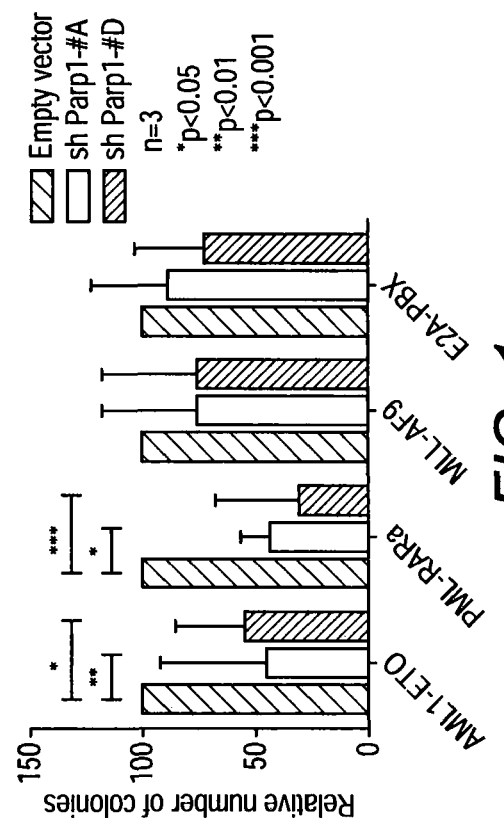

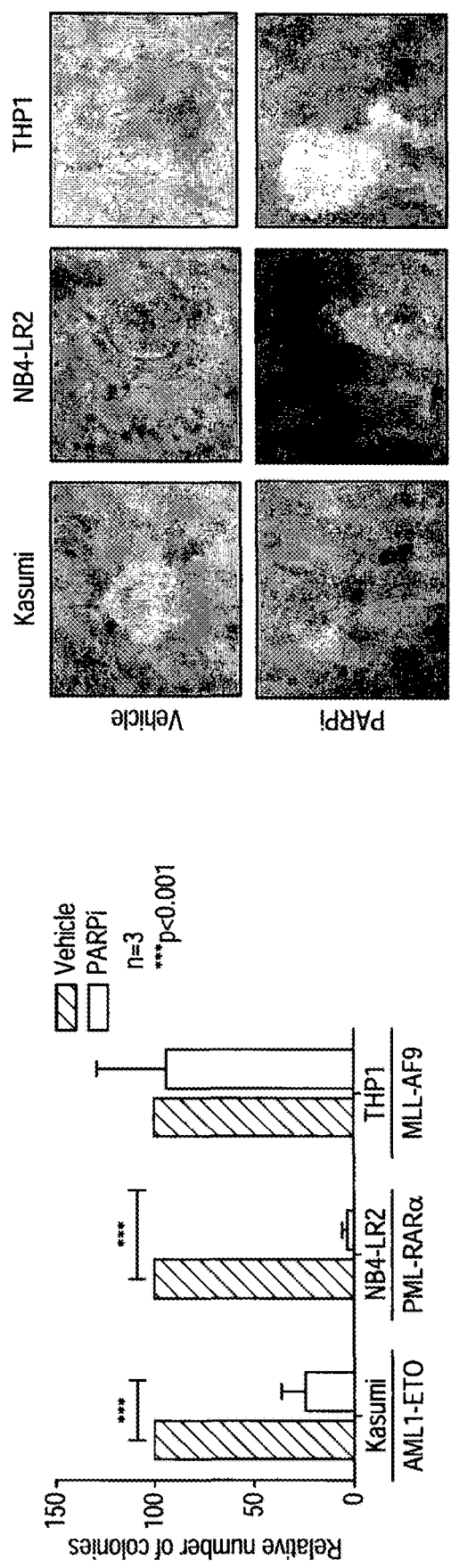
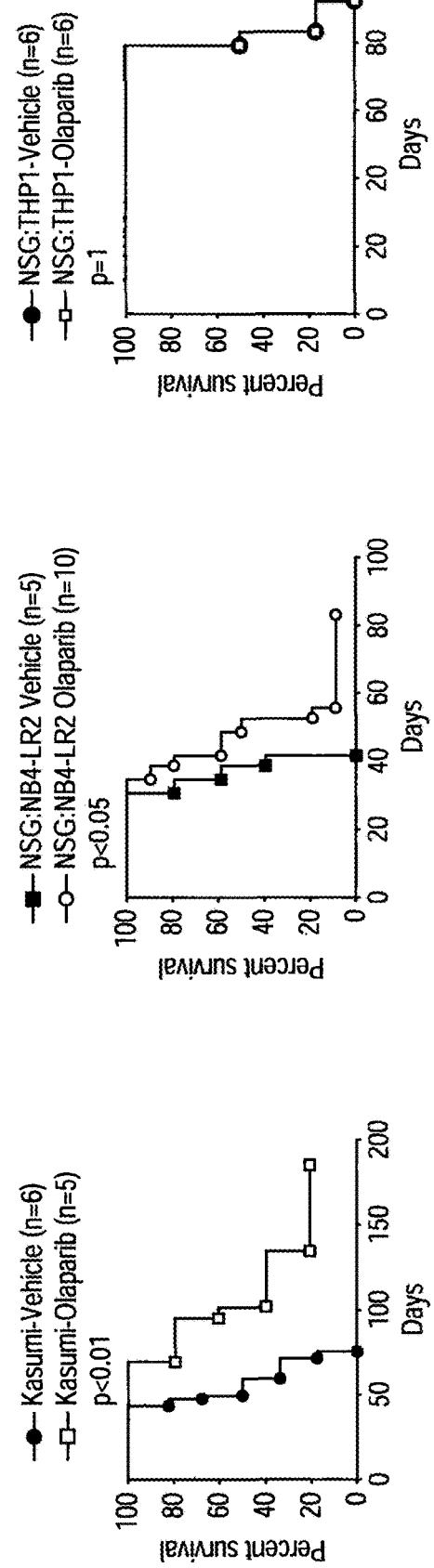
FIG. 1e
FIG. 1f
FIG. 1g
FIG. 1h
FIG. 1i

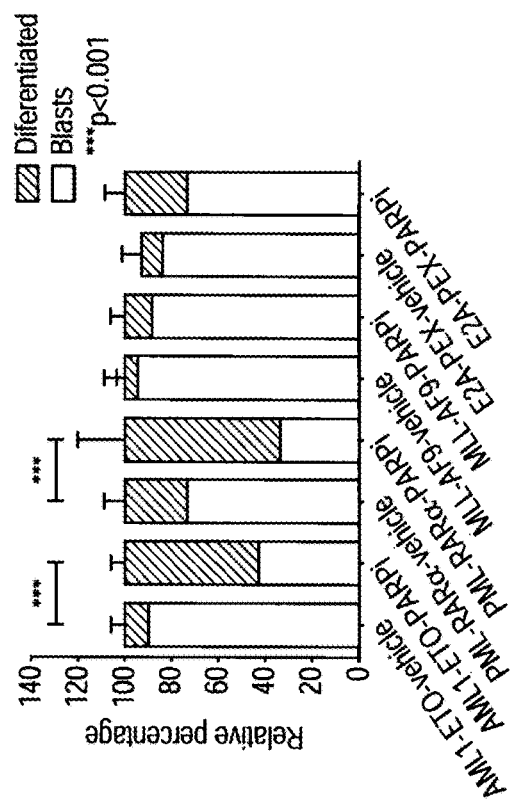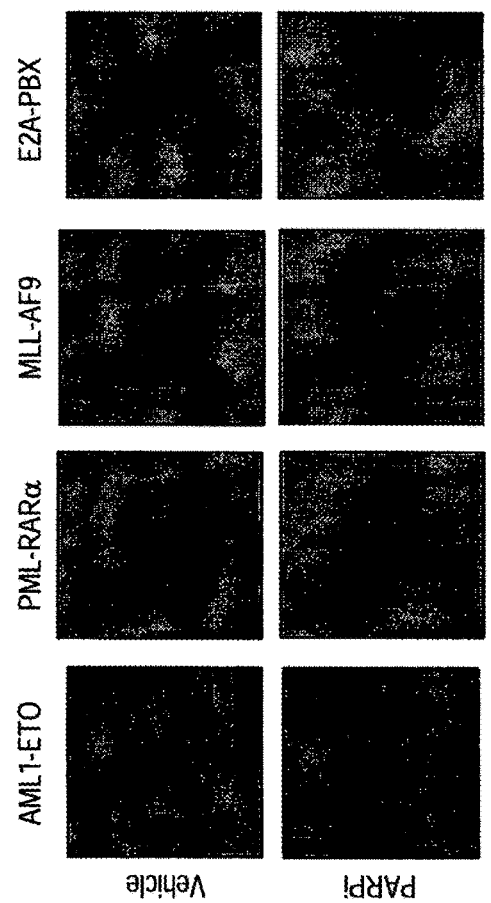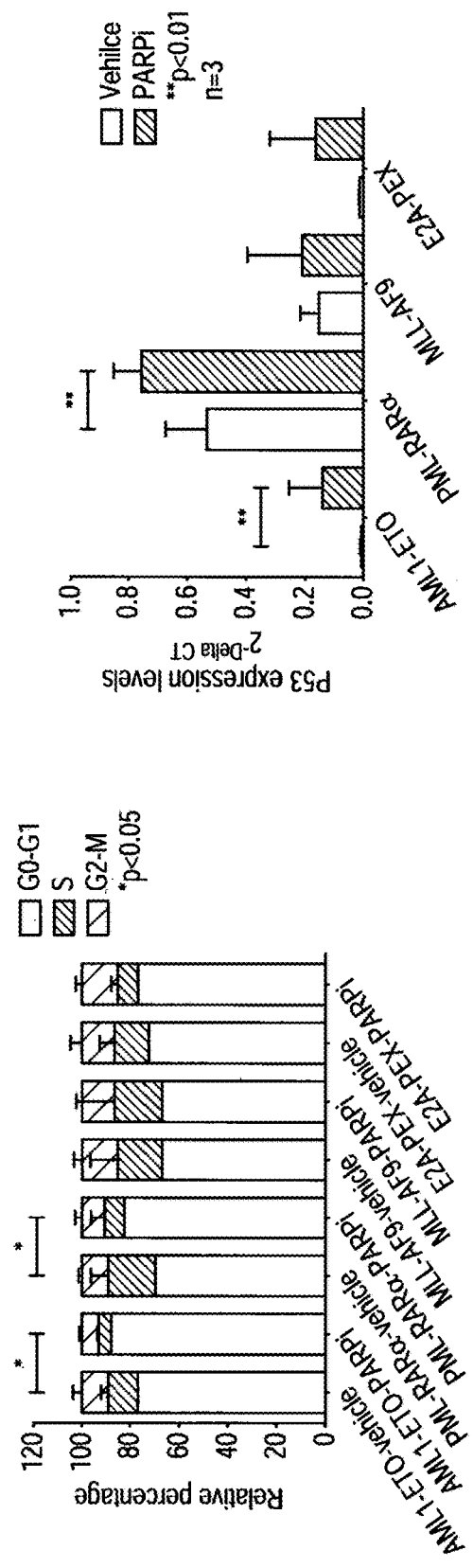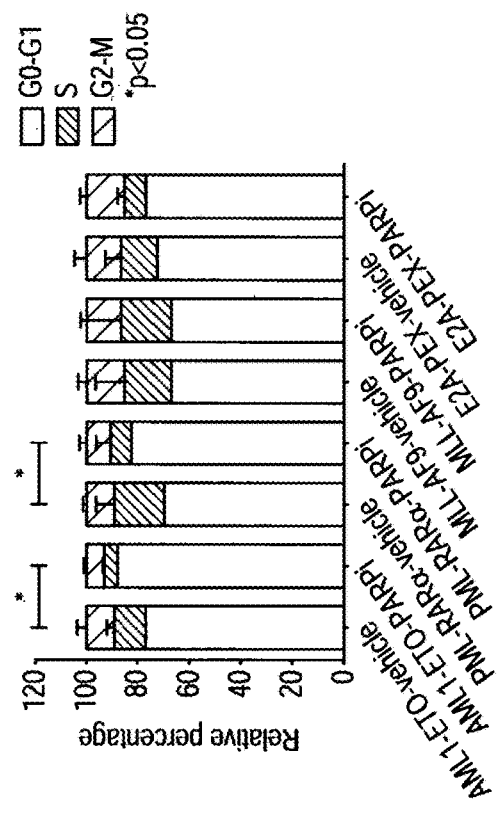
FIG. 2a
FIG. 2b
FIG. 2c
FIG. 2d

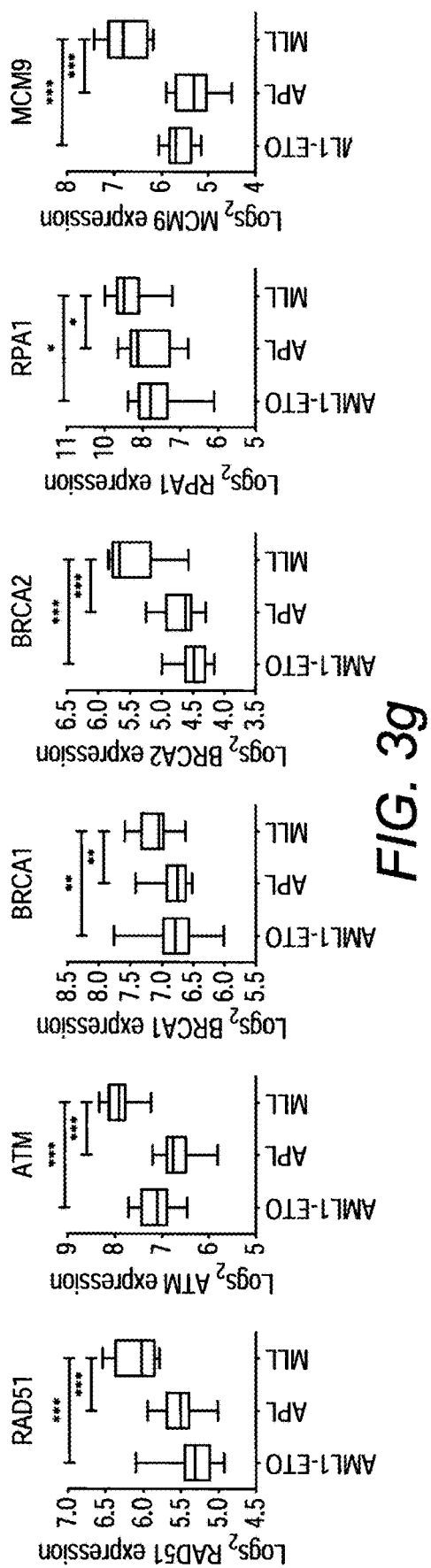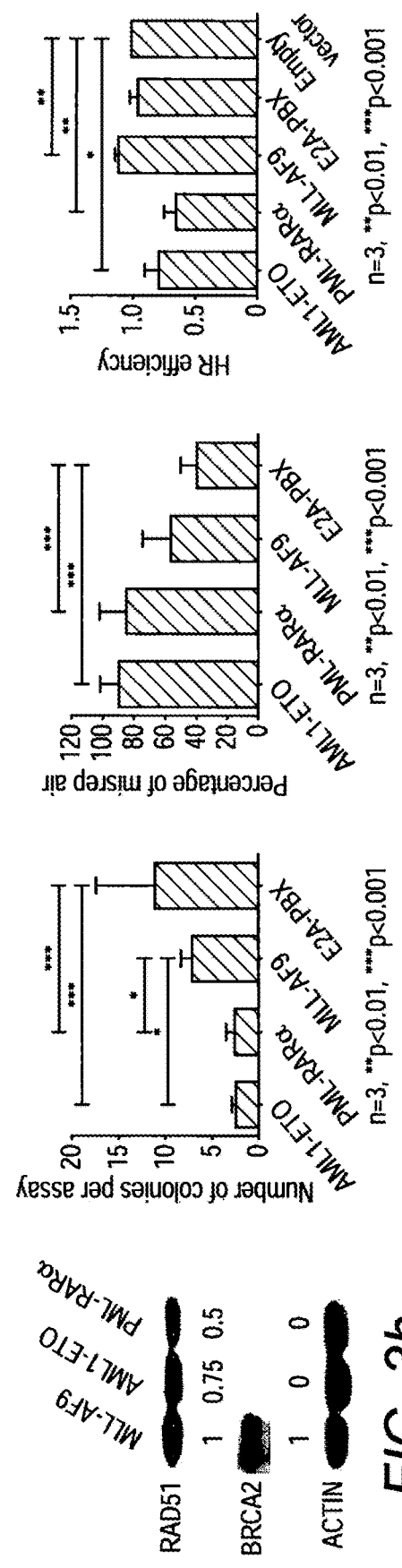
FIG. 3g
FIG. 3h
FIG. 3i
FIG. 3j
FIG. 3k

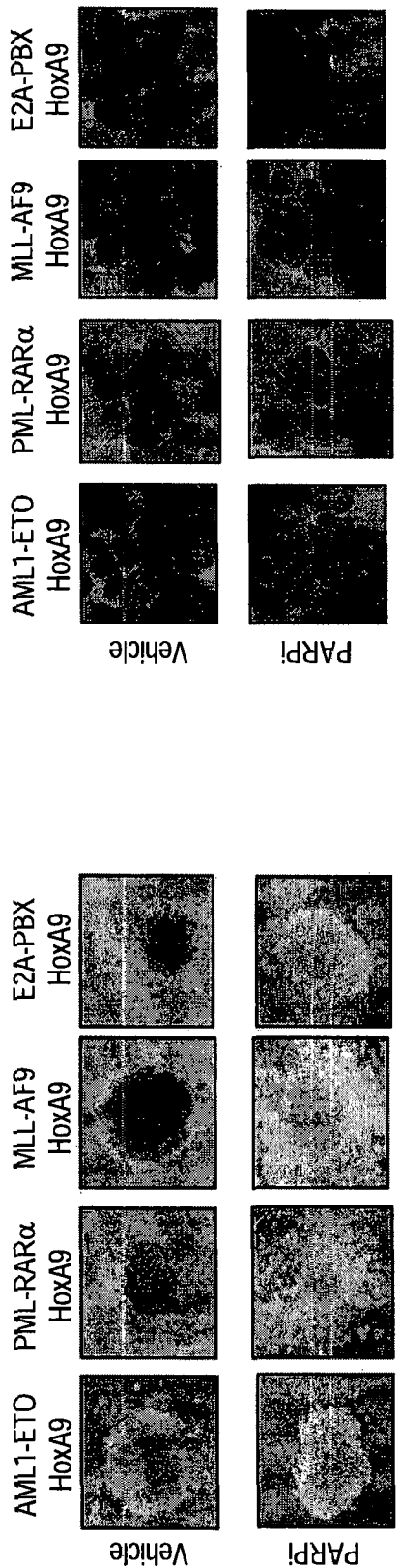
FIG. 4j
FIG. 4i
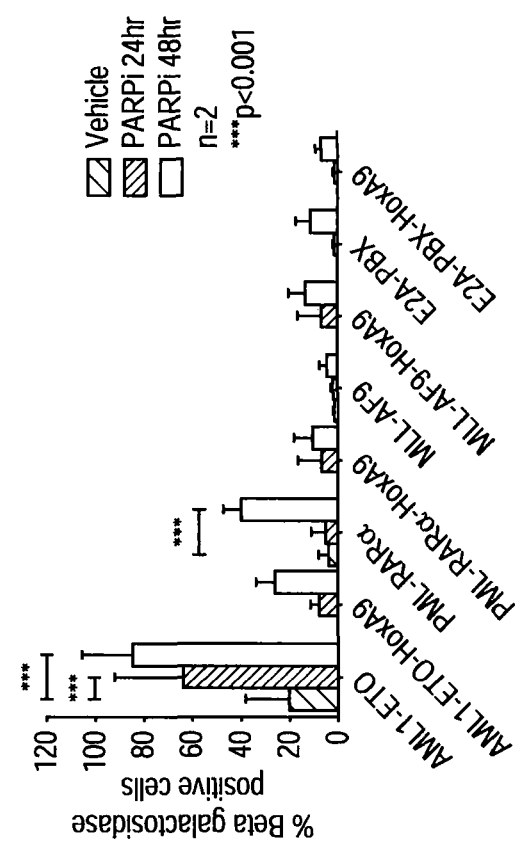
FIG. 4l
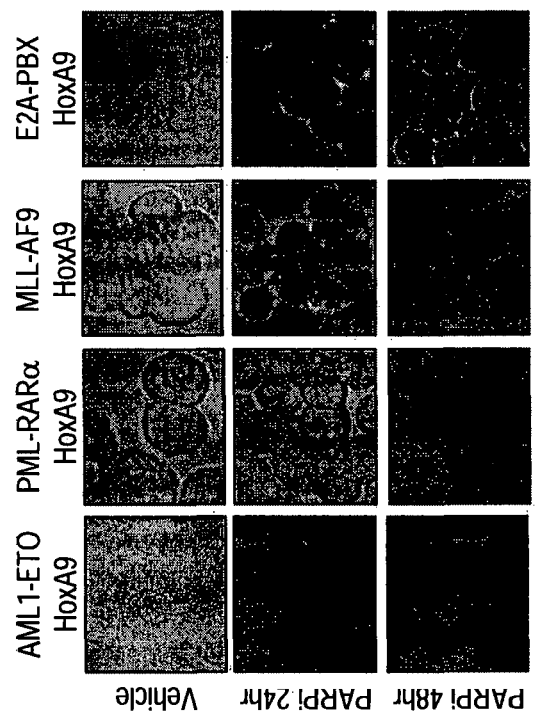
FIG. 4k

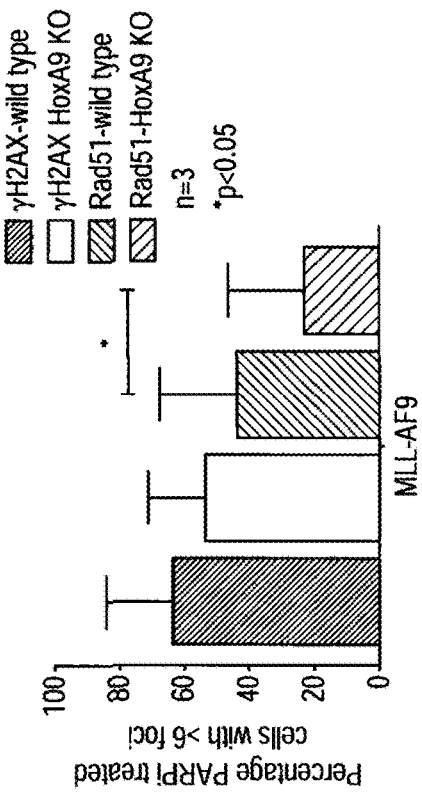
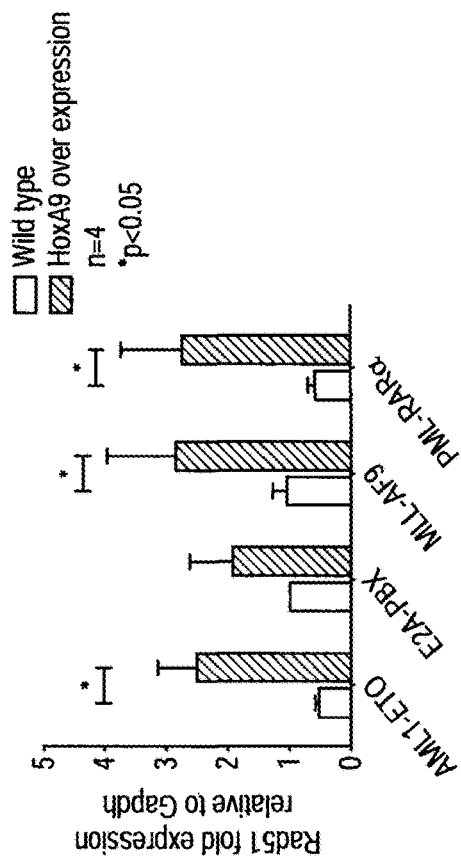
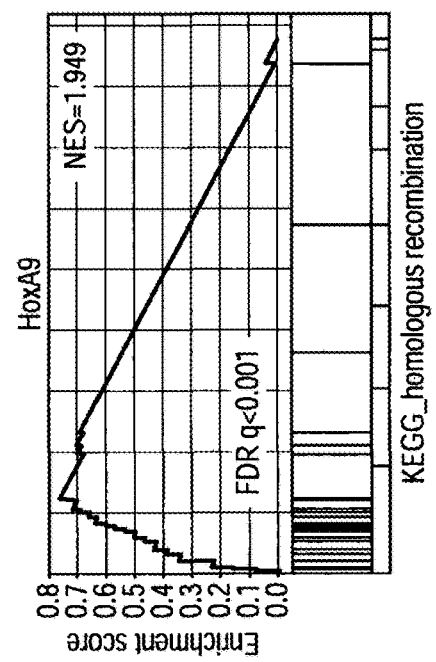
FIG. 5c
FIG. 5d
FIG. 5e
FIG. 5f

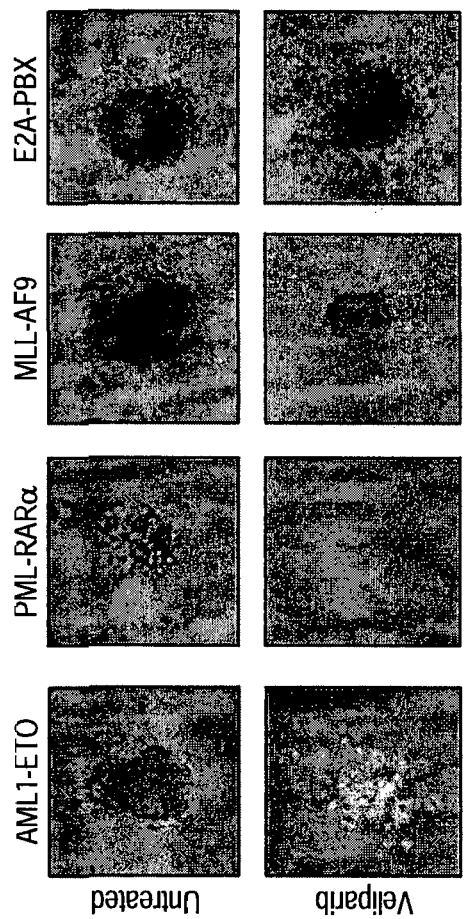
FIG. 7f
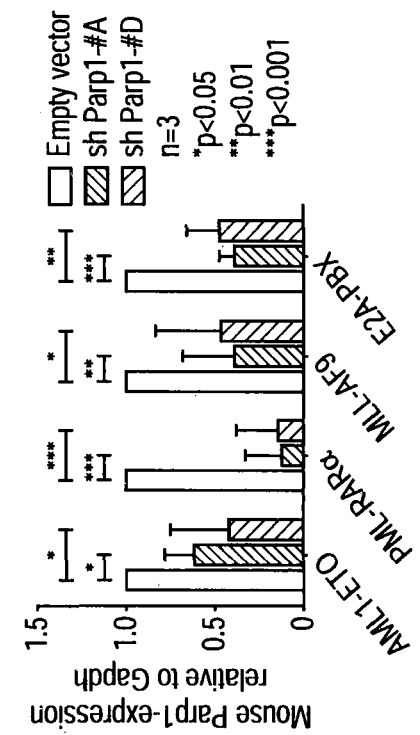
FIG. 7h
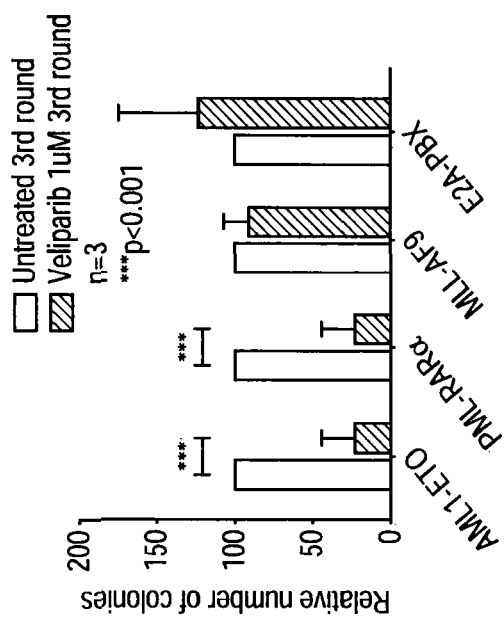
FIG. 7e
FIG. 7g

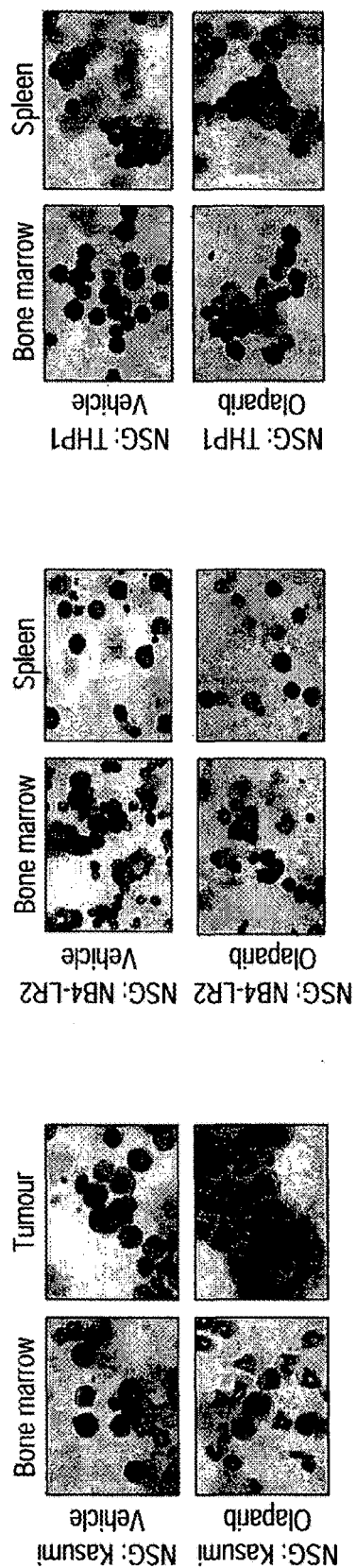
FIG. 7o
FIG. 7n
FIG. 7m
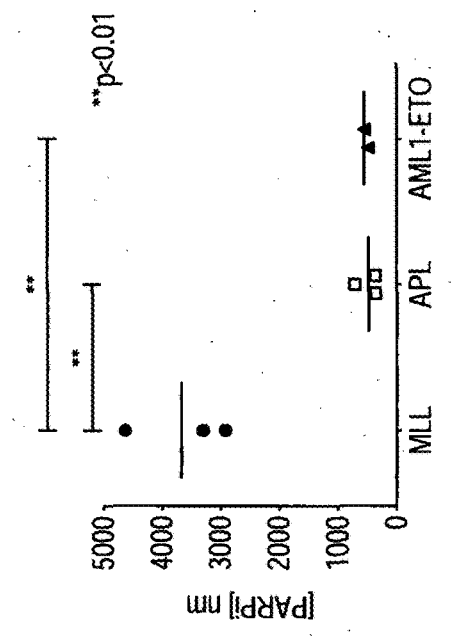
FIG. 7q
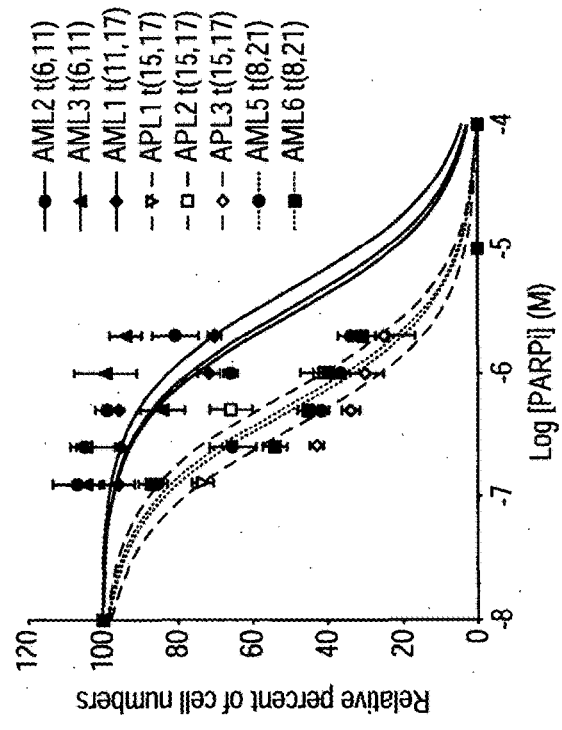
FIG. 7p

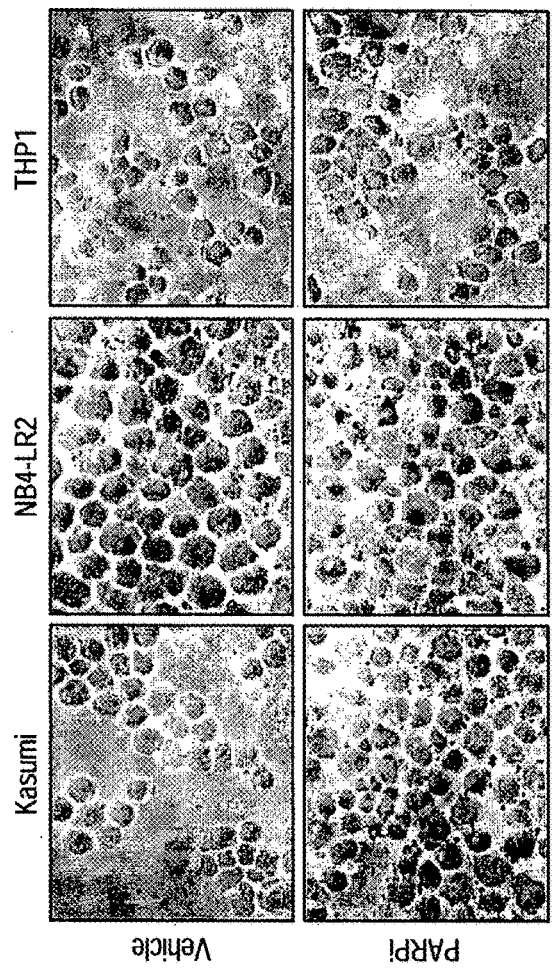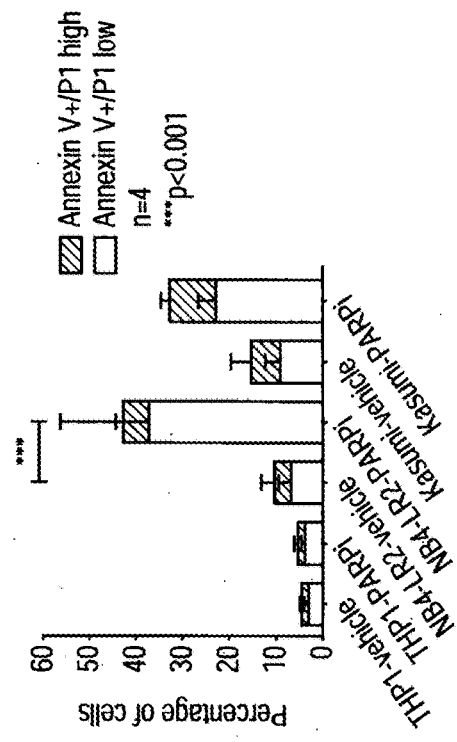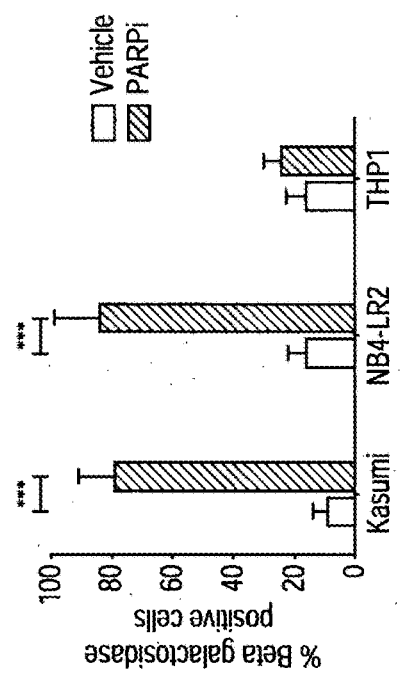
FIG. 8g
FIG. 8h
FIG. 8i

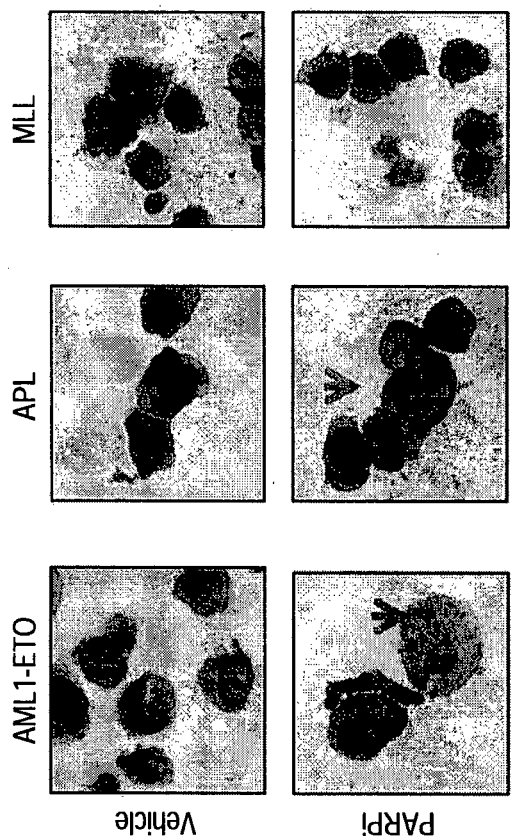
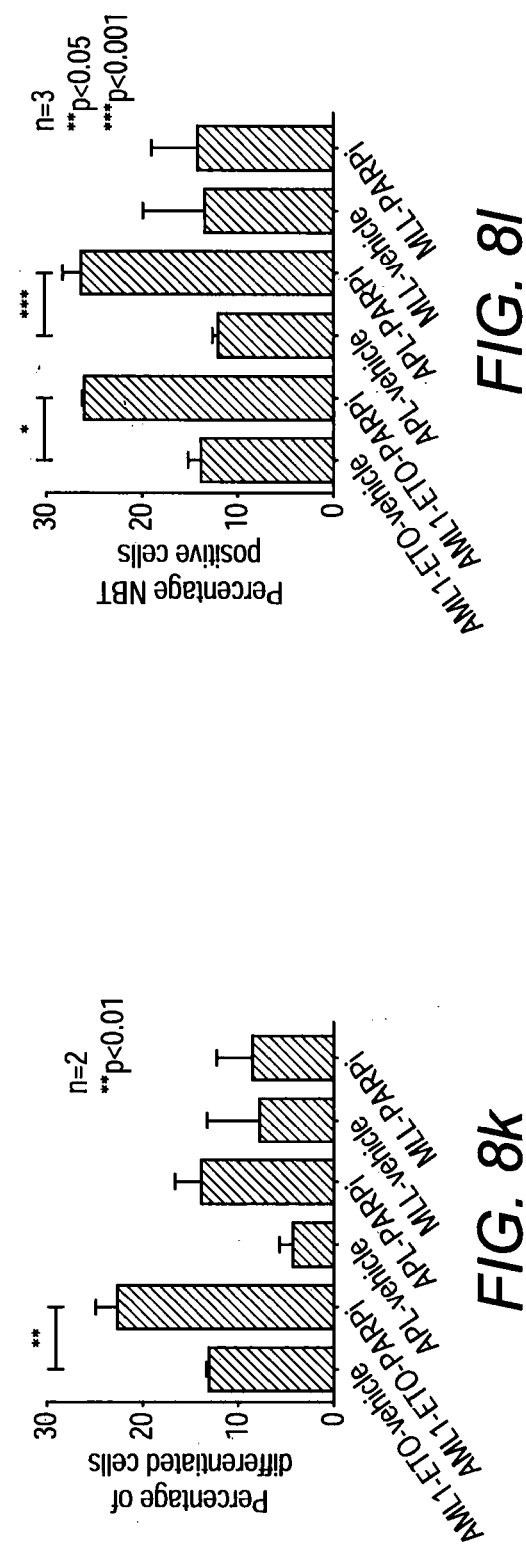
FIG. 8j
FIG. 8k
FIG. 8l

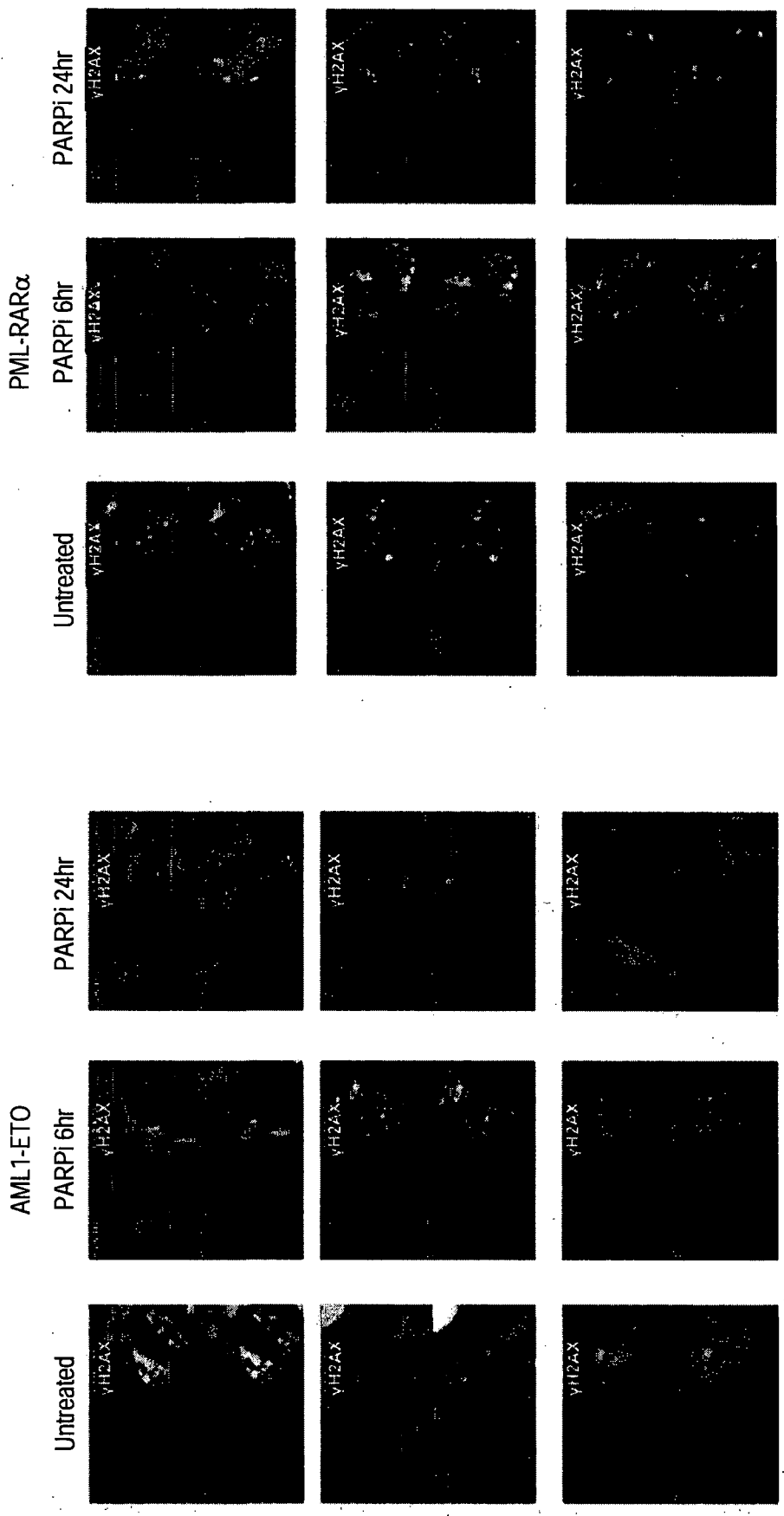

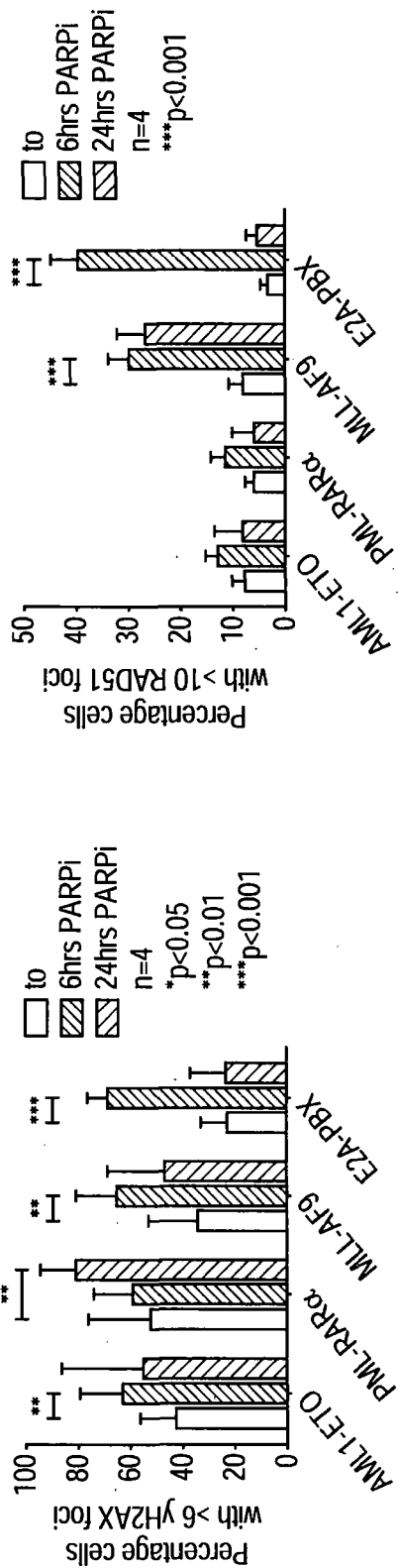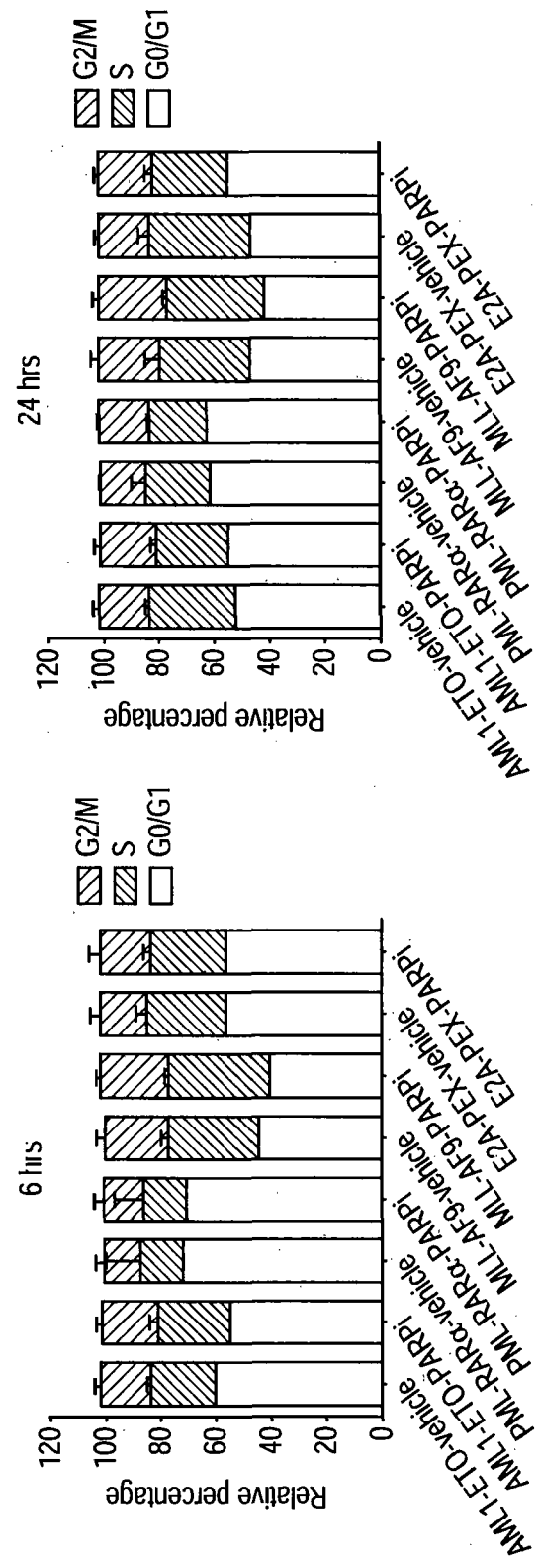
FIG. 9l
FIG. 9k
FIG. 9m

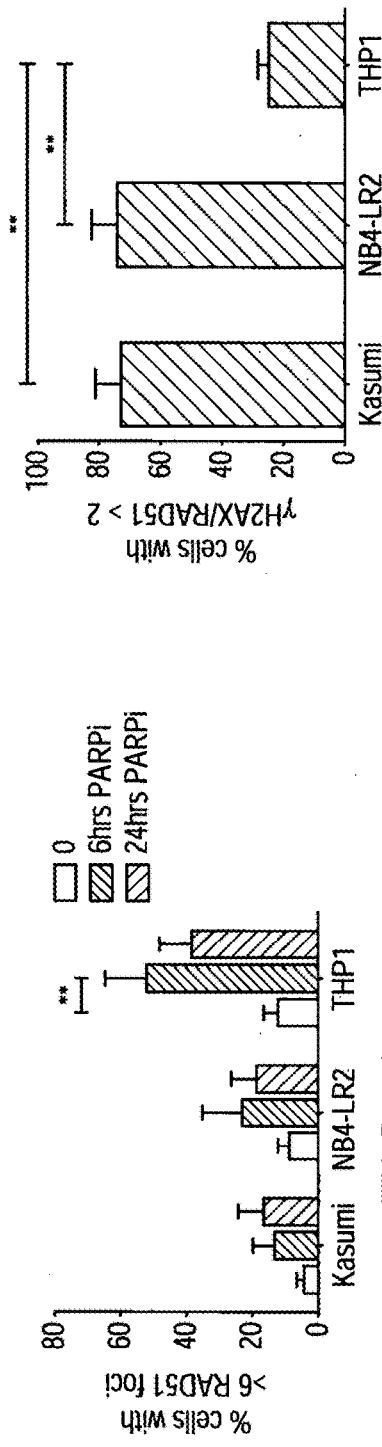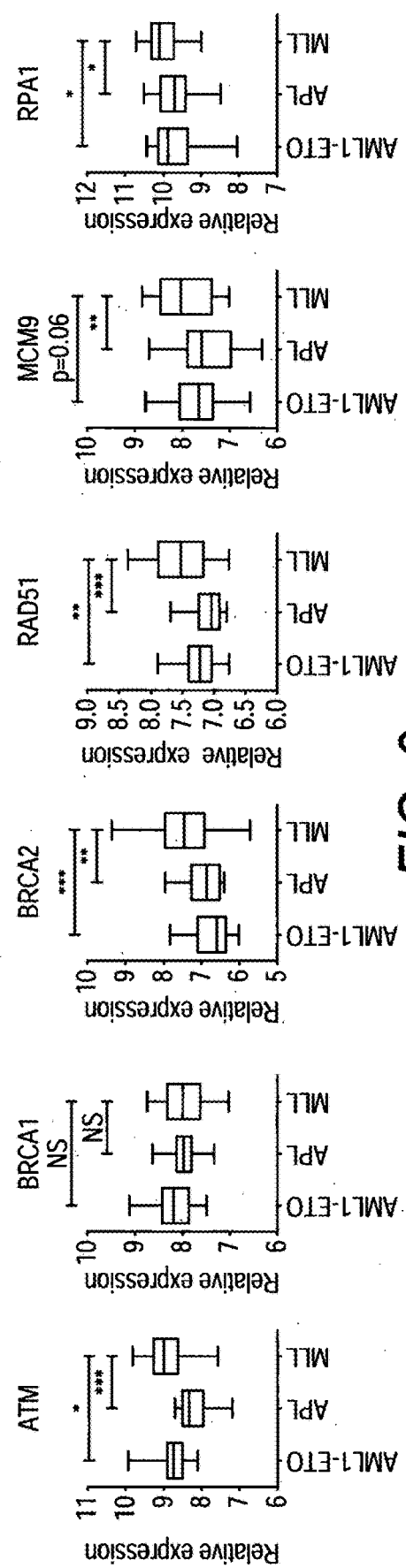
FIG. 9q
FIG. 9r
FIG. 9s

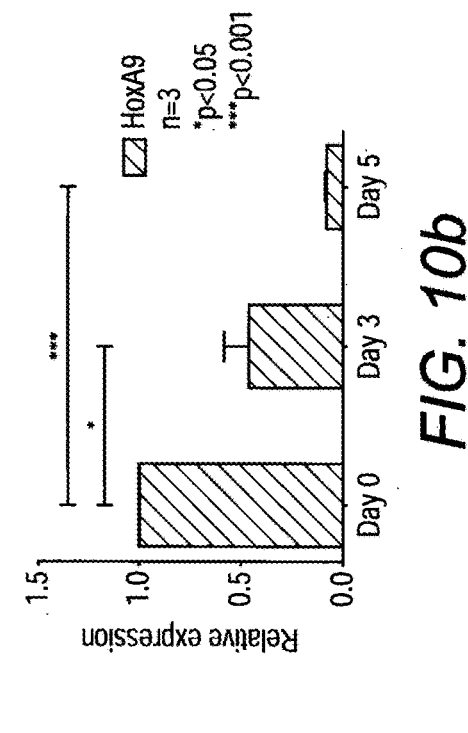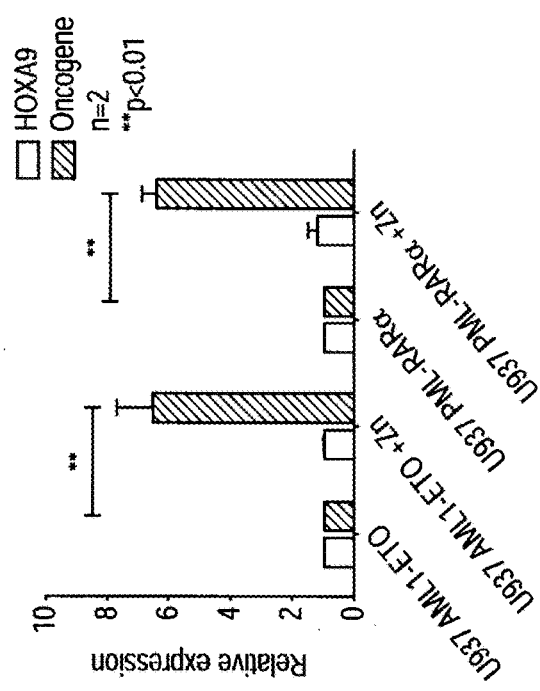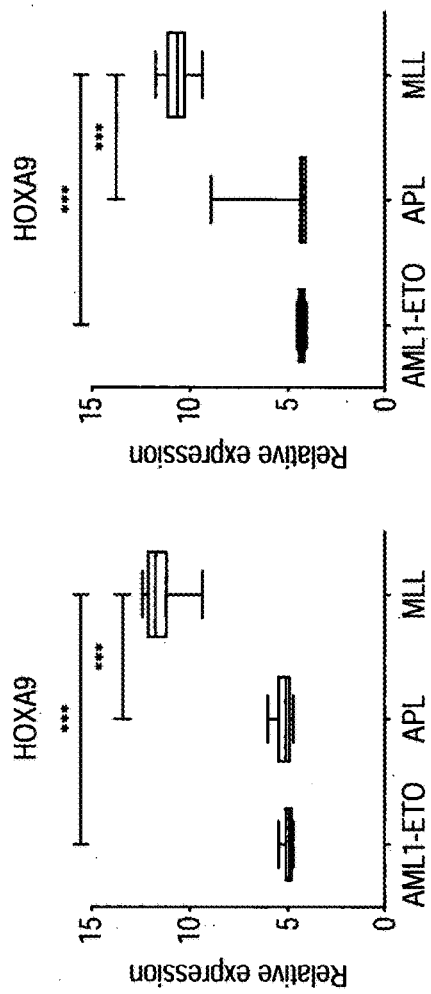
FIG. 10a
FIG. 10b
FIG. 10c

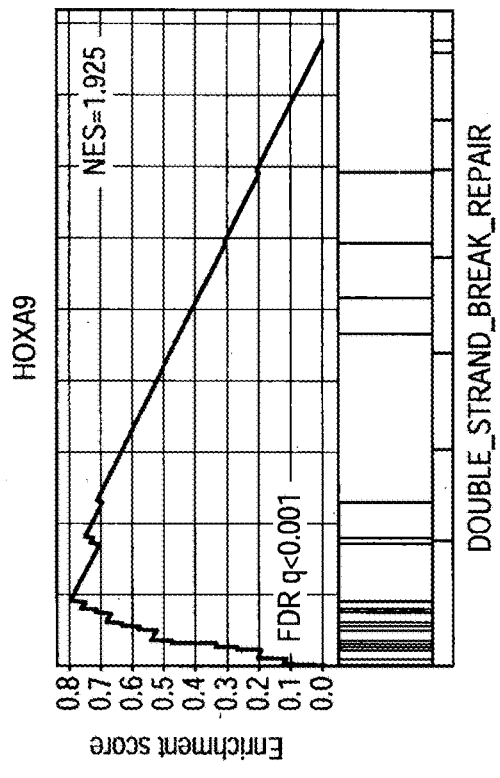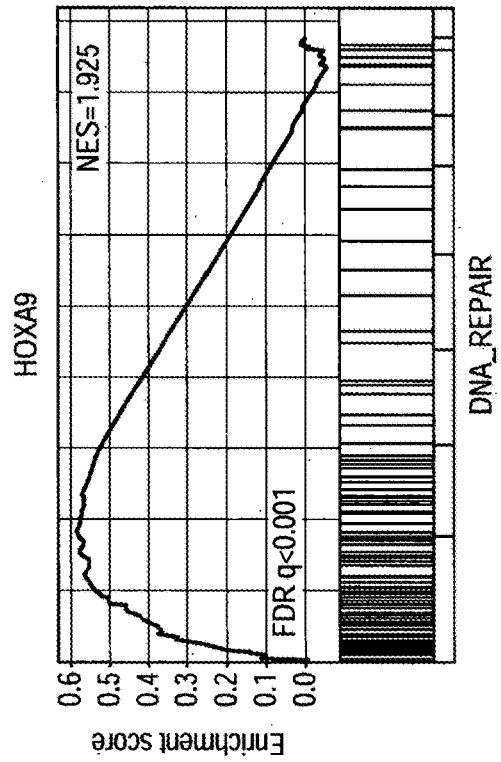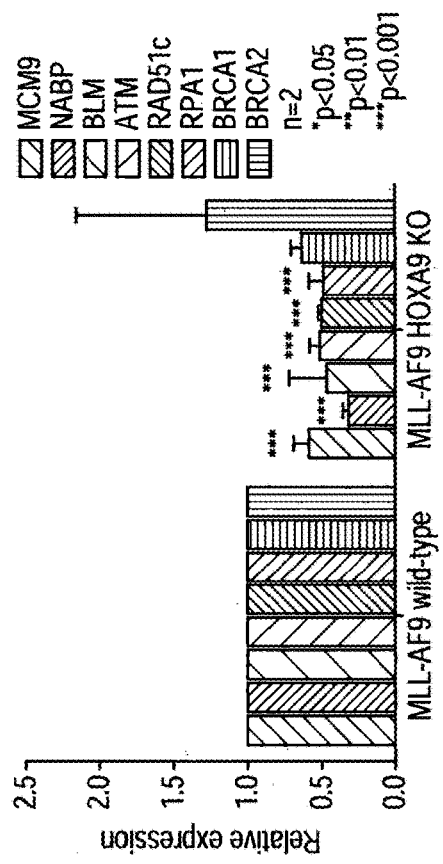
FIG. 11a
FIG. 11b
FIG. 11c

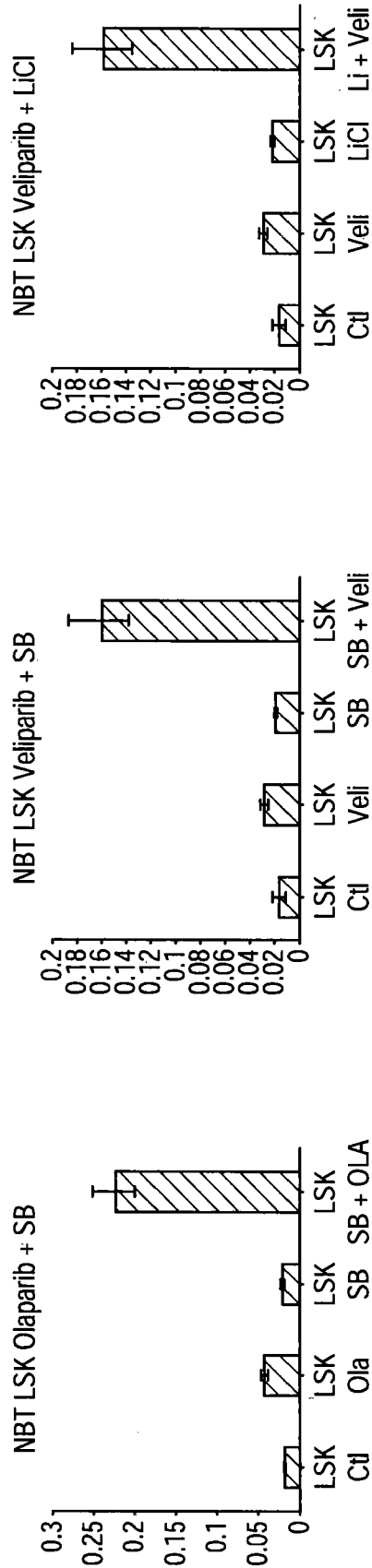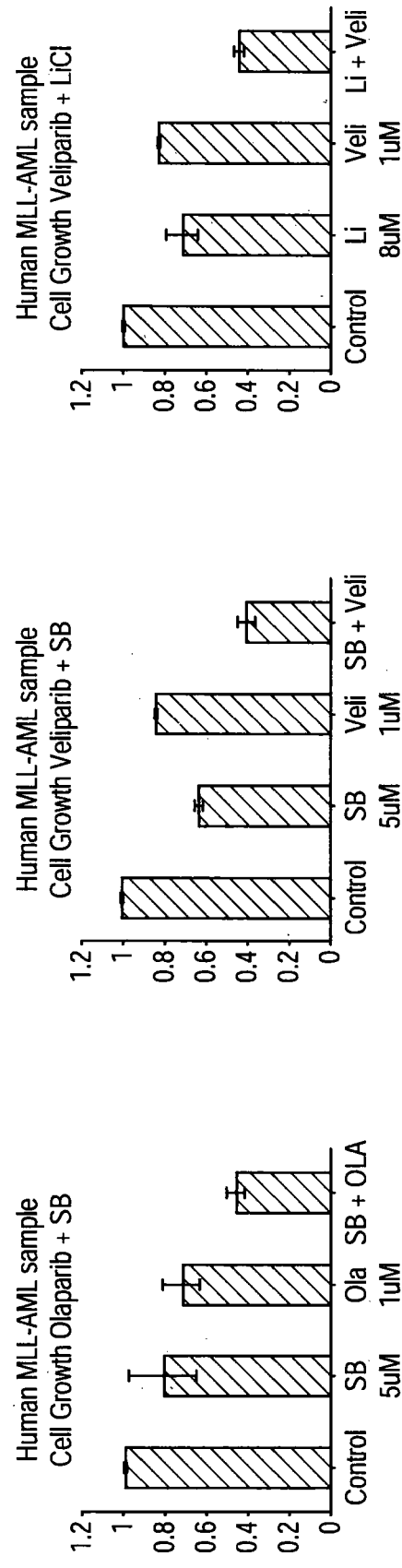

SEQUENCE LISTING

```
<160> NUMBER OF SEQ ID NOS: 3

<210> SEQ ID NO 1
<211> LENGTH: 19
<212> TYPE: DNA
<213> ORGANISM: Mus musculus

<400> SEQUENCE: 1
taaagaagct gacggtgaa                                              19

<210> SEQ ID NO 2
<211> LENGTH: 19
<212> TYPE: DNA
<213> ORGANISM: Mus musculus

<400> SEQUENCE: 2
gccgcctact ctatcctca                                              19

<210> SEQ ID NO 3
<211> LENGTH: 19
<212> TYPE: DNA
<213> ORGANISM: Artificial Sequence
<220> FEATURE:
<223> OTHER INFORMATION: scramble sequence

<400> SEQUENCE: 3
gcgaaagatg ataagctaa                                              19
```

COMBINATION OF AN INHIBITOR OF PARP WITH AN INHIBITOR OF GSK-3 OR DOT1L

FIELD OF THE INVENTION

The present invention relates generally to the field of cancer diagnosis and treatment. In particular, the invention relates to pharmaceutical agents and combinations for the treatment of acute myeloid leukaemia (AML) and sub-types thereof. The invention further relates to improved methods for treating AML involving administration of a pharmaceutical combination to a subject.

BACKGROUND OF THE INVENTION

Since its application in BRCA1/2 mutated cancer in just a decade ago, synthetic lethal approaches induced by Poly-(ADP-ribose)-polymerase (PARP) inhibitors (PARPi) have given renewed enthusiasm to developing anticancer treatments that can specifically target cancer cells but spare the normal[1,2]. While different models have been proposed to explain the molecular mechanisms underlying the synthetic lethality[3,4], they mostly attribute to the critical function of PARP in a variety of DNA repair processes including Base Excision Repair (BER) as a critical sensor of Single Strand Breaks (SSBs)[5,6], Homologous Recombination (HR) as a mediator for restart of stalled replication forks of HR-mediated Double Strand Break (DSB) repair[7-9], and Non-Homologous End-Joining pathway (NHEJ) by preventing the binding of Ku proteins to DNA ends[10]. Specifically, inhibition of BER impairs SSB repair, which results in accumulation of DSB at the replication forks during the S-phase. While it is also noted that an alternative but not mutative exclusive model has also been proposed where PARPi may actually function as poisons that result in PARP trapping[4], DNA repair and survival of PARP inhibited cells seem to be heavily dependent on HR, which are compromised in cancer cells carrying BRCA related mutations[11-17] leading to their unique susceptibility to PARPi treatment.

In spite of the promise in breast and ovarian cancer, clinical application of PARPi has not widely been translated to different cancers as an effective treatment since mutations affecting DNA Damage Response (DDR) genes are not common in other malignancies including acute myeloid leukemia (AML)[18], which is mainly driven by mutated transcription factors such as AML1-ETO, PML-RARα and MLL fusions[19]. Despite the advance in understanding of the genetic basis of the disease, the same chemotherapy treatment developed over half a century ago are still used for all AML patients, the only exception being Acute Promyelocytic Leukemia (APL) carrying PML-RARα[20].

Due to the high general toxicity, chemotherapy can usually only apply to young patients of age under 60, leaving little or no treatment options for the majority of AML patients. In addition, standard chemotherapy only induces long-term complete remission in less than 40% of patients and is mostly ineffective in patients carrying mutations in the Mixed Lineage Leukemia (MLL) gene[20]. WO 2015/040378 discloses that PARP inhibitors are effective in treating subjects expressing the mutant fusion proteins AML1-ETO and PML-RARα, but are ineffective in treating subjects expressing mutant MLL fusion proteins. Therefore there is an urgent need to develop better therapeutic strategies for AML, especially MLL.

SUMMARY OF THE INVENTION

In one aspect, the present invention provides a pharmaceutical combination comprising (a) a poly-(ADP-ribose)-polymerase (PARP) inhibitor and (b) a second agent. Preferably the second agent inhibits signalling via a Hox family member. Preferably the second agent inhibits Hoxa9 signalling.

In one embodiment, the second agent (e.g. an agent that inhibits Hoxa9 signalling) is an inhibitor of glycogen synthase kinase 3 (GSK-3). Preferably the GSK-3 inhibitor comprises lithium, e.g. a lithium salt such lithium carbonate. In another embodiment, the GSK-3 inhibitor is a specific GSK-3 inhibitor, e.g. SB216763.

In another embodiment, the second agent (e.g. an agent that inhibits Hoxa9 signalling) is an inhibitor of disrupter of telomeric silencing 1-like (DOT1L). Preferably the DOT1L inhibitor is EPZ-5676 or EPZ-4777.

In some embodiments, the PARP inhibitor is selected from olaparib, veliparib, CEP-8983 or a prodrug thereof, rucaparib, E7016, BMN-673 and INO-1001, and analogues and derivatives thereof. Preferably the PARP inhibitor is olaparib or veliparib.

In another aspect, the present invention provides a pharmaceutical combination comprising (a) a poly-(ADP-ribose)-polymerase (PARP) inhibitor and (b) a second agent (e.g. an agent that inhibits Hoxa9 signalling, a GSK3 inhibitor or DOT1L inhibitor) for simultaneous, separate or sequential use in the treatment of acute myeloid leukaemia (AML).

In one embodiment, the pharmaceutical combination is for use in the treatment of a subject suffering from mixed lineage leukaemia (MLL) subtype of AML. Preferably the subject has a chromosomal abnormality at 11q23, e.g. resulting in a rearranged MLL gene and/or expression of a MLL fusion protein.

In a further aspect, the present invention provides a method of treating a subject suffering from acute myeloid leukaemia, comprising administering to the subject a therapeutically effective amount of (a) a poly-(ADP-ribose)-polymerase (PARP) inhibitor and (b) a second agent (e.g. an agent that inhibits Hoxa9 signalling, a GSK3 inhibitor or DOT1L inhibitor).

In one embodiment, the second agent (e.g. an agent that inhibits Hoxa9 signalling) is an inhibitor of glycogen synthase kinase 3 (GSK-3). Preferably the GSK-3 inhibitor comprises lithium.

In another embodiment, the second agent (e.g. an agent that inhibits Hoxa9 signalling) is an inhibitor of disrupter of telomeric silencing 1-like (DOT1L). Preferably the inhibitor of DOT1L is EPZ-5676 or EPZ-4777.

In further embodiments, the PARP inhibitor is selected from olaparib, veliparib, CEP-8983 or a prodrug thereof, rucaparib, E7016, BMN-673 and INO-1001, and analogues and derivatives thereof.

In some embodiments, the subject is suffering from mixed lineage leukaemia (MLL). Preferably the subject has a cytogenetic abnormality at chromosome 11q23, e.g. the subject has a rearranged MLL gene and/or expresses an oncogenic MLL fusion protein.

In a further aspect, the present invention provides a method for selecting a therapy for a subject suffering from acute myeloid leukaemia, comprising determining whether a chromosomal abnormality at 11q23 is present in a sample obtained from the subject; wherein if the chromosomal abnormality at 11q23 is present in the sample, a therapy comprising combined administration of (a) a poly-(ADP-ribose)-polymerase (PARP) inhibitor and (b) a second agent (e.g. an agent that inhibits Hoxa9 signalling, a GSK3 inhibitor or DOT1L inhibitor) is selected for the subject.

In one embodiment, the chromosomal abnormality comprises a rearranged MLL gene and/or expression of a MLL fusion protein.

In another embodiment, if a chromosomal abnormality selected from t(8;21) and t(15;17) is detected in the sample, a therapy comprising poly-(ADP-ribose)-polymerase (PARP) inhibitor monotherapy is selected for the subject. Preferably the chromosomal abnormality results in expression of a fusion protein comprising (a) acute myeloid leukemia-1 transcription factor and eight-twenty-one corepressor (AML1-ETO) or promyelocytic leukaemia protein and retinoic acid receptor alpha (PML-RARα).

In a further aspect, the present invention provides use of a pharmaceutical combination comprising (a) a poly-(ADP-ribose)-polymerase (PARP) inhibitor and (b) a second agent (e.g. an agent that inhibits Hoxa9 signalling, a GSK3 inhibitor or DOT1L inhibitor) for the preparation of a medicament for treating acute myeloid leukaemia. Preferably the acute myeloid leukaemia comprises mixed lineage leukaemia.

BRIEF DESCRIPTION OF THE DRAWINGS

FIG. 1: PARPi targets AML1-ETO and PML-RARα leukemic cells in vitro and in vivo.

Figure 2E:
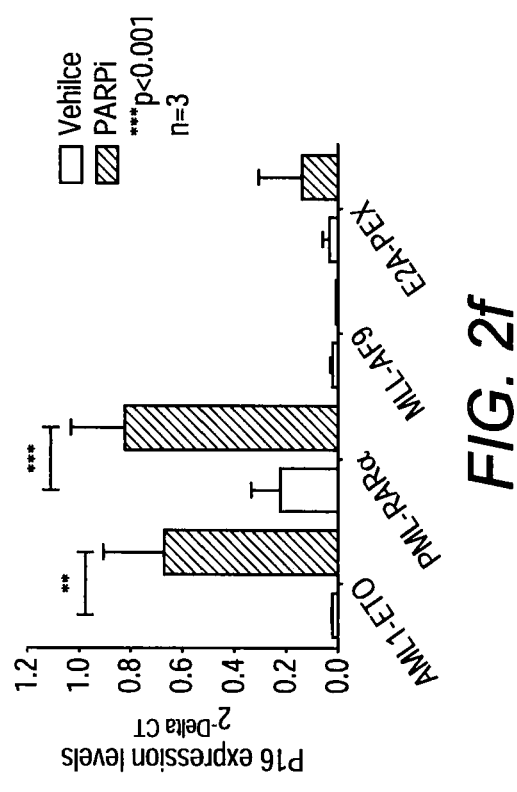
Figure 2F:
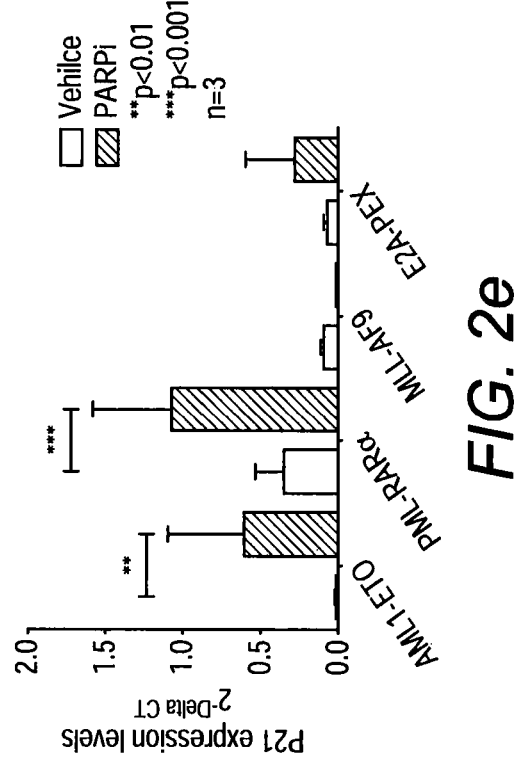

a) Relative number of colonies of leukemic cells surviving to PARPi, Olaparib. The number of colonies was acquired after seven days of Olaparib treatment in each round and data was normalized against the vehicle control. Data represents means of six independent experiments±SD. 1-way ANOVA test was performed between vehicle and Olaparib treated cells for each condition ***$p<0.001$. b) Representative colony morphology with or without Olaparib treatment. Images were acquired using a phase contrast microscope (magnification 40×). c) Relative number of colonies of oncogene-induced leukemic cells transduced either with empty vector or shRNA targeting Parp1. The number of colonies was normalized against empty vector control. Data represents means of at least three independent experiments±SD. 2-way ANOVA test was performed between empty vector and i) sh-Parp1-A and ii) sh-Parp1-D, *$p<0.05$, $p<0.01$, *$p<0.001$. d) Representative colony morphology of leukemic cells transformed by indicated oncoproteins and transduced with empty vector/Parp1 shRNA. Images were acquired using a phase contrast microscopy (magnification 40×). e) Relative number of colonies of human leukemic cell lines Kasumi (AML1-ETO), NB4-LR2 (PML-RARα) and THP1 (MLL-AF9) grown in methylcellulose for 7 days with 5 μM Olaparib. The number of colonies after PARPi treatment was normalized against the untreated control. Data represents means of three independent experiments±SD. 1-way ANOVA test was performed between untreated and Olaparib treated cells for each condition ***$p<0.001$. f) Colony morphology of human leukemic cell lines treated with PARPi (phase contrast microscopy, magnification 40×). Representative pictures are shown. g) Kaplan-Meier survival curve of NSG mice transplanted with Kasumi cell lines (vehicle n=6, Olaparib n=5, pooled from two independent experiments). Log-rank (Mantel-Cox) test was performed between the two curves, $p<0.01$. h) Kaplan-Meier survival curve of NSG mice transplanted with NB4-LR2 cell line (vehicle n=5, Olaparib n=10). Log-rank (Mantel-Cox) test was performed between the two curves, $p<0.05$. i) Kaplan-Meier survival curve of NSG mice transplanted with human THP1 cells (vehicle n=5, Olaparib n=5). Log-rank (Mantel-Cox) test was performed between the two curves, $p=1$.

FIG. 2: PARPi induces differentiation, senescence, and apoptosis of AML1-ETO and PML-RARα leukemic cells a) Giemsa-MacGrunwald staining of leukemic cells showing myeloid differentiation in AML1-ETO and PML-RARα leukemic cells upon treatment with PARPi. b) Quantification of morphologically differentiated cells relating to FIG. 2(a). 1-way ANOVA was performed between vehicle and PARPi treated cells ***$p<0.01$. c) Cell cycle analysis of leukemic cells after 48-72 hrs of continuous PARPi treatment. Relative percentage of cells in G0-G1, S and G2-M phases are shown. Data represents means of three independent experiments±SD. 1-way ANOVA was performed between vehicle and PARPi treated cells *$p<0.05$. d-f) Expression of d) Trp53, e) Cdkn1a/p21 and f) Cdkn2a/p16 in the indicated transformed cells following continuous PARPi treatment. Expression of the target genes was normalized against Gapdh (2-ΔCT). Data represents means of three independent experiments±SD. Unpaired t-test performed between vehicle and PARPi treated cells *$p<0.05$, $p<0.01$, *$p<0.001$. g) Detection of primary transformed cells undergoing senescence after 24 hrs and 48 hrs of PARPi treatment by β-galactosidase staining. Representative pictures are shown (40× magnification). h) Quantification of percentage of β-galactosidase positive cells. Data represents means of three independent experiments±SD. 1-way ANOVA test was performed between vehicle and PARPi treated cells for each condition at each time point, *$p<0.001$. i) Quantification of percentage of Annexin V+/PI+ and Annexin V+/PI− cells upon PARPi treatment at 24 hrs and 48 hrs. Data represents means six independent experiments±SD. 1-way ANOVA test was performed between untreated and PARPi treated cells for each condition at each time point, $p<0.01$.

FIG. 3: AML1-ETO and PML-RARα cells show a defect in HR pathway and accumulate DNA damage in response to PARPi treatment.

a) Immunofluorescence microscopy of γH2AX foci in untreated primary transformed mouse cells with the nuclei shown in blue and γH2AX foci in green (representative cells). b) Quantification of the percentage of cells with more than 6 γH2AX foci±SD in untreated condition. 1-way ANOVA test was performed between 1) AML1-ETO and E2A-PBX, 2) PML-RARα and E2A-PBX, and 3) MLL-AF9 and E2A-PBX (n>3 $p<0.01$, *$p<0.001$). c) Time-course analysis of PARPi induced γH2AX and RAD51 foci by immunofluorescence upon continuous PARPi treatment with the indicated time. The panels show the nuclei in blue, γH2AX foci in green and RAD51 foci in red (representative cells). d) Quantification of percentage of RAD51 positive cells (>6 foci) 0 hr (white bars), 6 hrs (yellow bars) and 24 hrs (red bars) upon PARPi treatment is shown. 1-way ANOVA test was performed between untreated and 1) 6 hr and 2) (n=4 *$p<0.05$ ***$p<0.001$). e) The percentage of cells with γH2AX/RAD51 ratio >2 is shown (n=3*$p<0.05$). f) RT-qPCR data of Rad51, Brca1, Brca2, Atm, Mcm9 and Rpa1 expression in primary transformed mouse cells. Data represents means of four independent experiments±SD. 1-way ANOVA was performed between 1) AML1-ETO and MLL-AF9 and 2) PML-RARα and MLL-AF9; *$p<0.05$, $p<0.01$, *$p<0.001$. g) Box-plots showing relative microarray expression of RAD51, ATM, BRCA1, BRCA2, MCM9 and RPA1 in AML patients carrying the translocation AML1-ETO, PML-RARα (APL) or MLL-fusions. h) Western blot showing the relative expression levels of RAD51, BRAC2 in mouse pre-leukemic cells. Beta ACTIN was used as loading control for quantification to generate the indicated relative signal of the bands. i) Colony forming efficiency as indicative of DSB repair is shown. Repair efficiency is assessed as the total number of bacterial colonies obtained per transformation and expressed as mean±SEM. 1-way ANOVA was performed between indicated samples (n=3) *p<0.05, *p<0.001. j) Percentage of misrepair in panel i). Misrepair is calculated as the fraction of white colonies in total (blue and white) colonies, expressed as mean±SEM. 1-way ANOVA was performed between the indicated samples (n=3) *p<0.001. k) Efficiency of HR-mediated repair of I-SceI-induced DSB in U2OS/DR-GFP. Cells were transfected with I-SceI, dsRFP and indicated oncogenes or vector control. Data represents relative repair efficiency calculated as a percentage of repair efficiency measured in cells transfected with empty vector. All data points represents means of three independent experiments±SD. 1-way ANOVA was performed between indicated samples (n=3) *p<0.05, **p<0.01.

FIG. 4: HOXA9 modulates the sensitivity to PARPi a) Relative colony number of primary transformed cells from wild-type or Hoxa9−/− background surviving to PARPi. The number of colonies was counted after seven days culture in methylcellulose with PARPi and normalized against the wild-type control. Data represents means of at least five independent experiments±SD. 2-way ANOVA test was performed among the data sets: i) wild type vehicle vs Hoxa9−/− vehicle, ii) Hoxa9−/− vehicle vs Hoxa9−/− PARPi p<0.01, *p<0.001. b) Representative colony morphology as in FIG. 4a (Phase contrast magnification 40×). c) Giemsa-MayGrunwald staining of cells generated with Hoxa9−/− mice. d) Detection of senescence by β-galactosidase staining of cells in panel c. e) Quantification of β-galactosidase positive cells in percentage upon 48 hrs PARPi treatment. Data represent means of two independent experiments±SD. Unpaired two-tailed t-test vehicle and PARPi 48 hrs, *p<0.05*p<0.001f-g) Kaplan-Meier survival curves of C57Bl/6 mice transplanted with MLL-AF9 leukemic cells generated in f) wild type (vehicle n=12, Olaparib n=12 pooled from three independent experiments) and g) Hoxa9−/−(vehicle n=14, Olaparib n=11 pooled from three independent experiments) background, respectively. Log-rank (Mantel-Cox) test was performed between the vehicle and the Olaparib group. h) Relative number of colonies of indicated primary transformed cells over-expressing HOXA9 in the presence of PARPi. The number of colonies surviving to 7 days incubation with PARPi was normalized against the vehicle control. Data represents means of three independent experiments±SD. Two-way ANOVA test was performed among the data sets: 1) wild type vehicle vs wild type PARPi, 2) wild type vehicle vs HOXA9-overexpression PARPi *p<0.001. i) Colony morphology (phase contrast microscopy, magnification 40×). Representative pictures are shown. j) Giemsa-MayGrunwald staining of primary transformed cells over-expressing HOXA9. k) Detection of senescent cells by β-galactosidase staining. l) Quantification of percentage of β-galactosidase positive cells upon PARPi treatment for 24 and 48 hrs as in panel k. Data represents means of 2 independent experiments±SD. 1-way ANOVA test was performed among the data sets: 1) vehicle vs PARPi 24 hrs, 2) vehicle vs PARPi 48 hrs, ***p<0.001.

FIG. 5: HOXA9 modulates PARPi sensitivity a) Immunofluorescence microscopy of PARPi induced (6 hours) γH2AX and RAD51 foci in wild type and HOXA9 over-expressing cells. Nuclei are shown in blue, γH2AX foci in green and RAD51 are shown in red (representative cells). b) The percentage of 1) γH2AX positive cells (>6 foci) in wild-type (filled black bars) and HOXA9 over-expressing cells (filled red bars) and 2) RAD51 in wild-type (striped black bars) and HOXA9 over-expressing cells (striped red bars) is shown. Two-way ANOVA test was performed among the data sets: 1) γH2AX in wild-type vs γH2AX in HOXA9 over-expression, 2) RAD51 in wild-type vs RAD51 in HOXA9 over-expression (n=2 p<0.01, *p<0.001). c) Immunofluorescence microscopy of PARPi induced (6 hours) γH2AX and RAD51 foci in MLL-AF9 cells generated in wild type and Hoxa9−/− background. Nuclei are shown in blue, γH2AX foci in green and RAD51 are shown in red (representative cells). d) The percentage of 1) γH2AX positive cells (>6 foci) in wild-type (filled black bars) and Hoxa9−/− cells (filled green bars) and 2) RAD51 in wild-type (striped black bars) and Hoxa9−/− cells (striped green bars) is shown. Two-way ANOVA test was performed among the data sets 1) γH2AX in wild-type vs γH2AX in Hoxa9−/−, 2) RAD51 in wild-type vs RAD51 in Hoxa9−/− (n=3 *p<0.05). e) Gene Set Enrichment Analysis (GSEA). Genes associated with homologous recombination pathway are enriched in the transcriptional profile of mouse myeloblasts over-expressing Hoxa9. NES, normalized enrichment score; FDR, false discovery rate. f) RTq-PCR showing expression levels of Rad51 in primary transformed mouse cells over-expressing HOXA9. (Expression levels relative to Gapdh, reference control E2A-PBX). Data represents means of four experiments±SD. Unpaired two-tailed t-test was performed between wild-type vs HOXA9 over-expression *p<0.05.) g) RT-qPCR data showing expression levels of Rad51 in MLL-AF9 cells generated in wild type and Hoxa9−/− background. Data represents means of two experiments±SD. Unpaired two-tailed t-test was performed between wild-type vs Hoxa9 KO, ***p<0.001) h) Western blot analysis of Rad51 and Brca2 in MLL-AF9 cells generated in wild-type, Hoxa9−/− and β-Catenin−/− background. β-ACTIN was shown as loading control. i) Bar chart shows efficiency of HR-mediated repair of I-SceI-induced DSB in U2OS cells. Cells were transfected with I-SceI, dsRFP and HOXA9 expressing/HOXA9 shRNA plasmids. In the case of HOXA9 over-expression, cells were subjected to 5Gy irradiation 24 hrs after transfection. Data is normalised to empty vector or scrambled shRNA. Data represents means of 3 independent experiments±SD. Unpaired t-test was performed between indicated samples (n=3) *p<0.05, **p<0.01.

FIG. 6: Combined PARPi and GSK3i treatment impairs in vivo survival of MLL leukemia a) Relative number of colonies of pre-leukemic cells surviving to PARPi, LiCl or combined PARPi+LiCl treatment. The number of colonies surviving to seven days incubation with drug treatment was normalized against the untreated control. Data represents means of three independent experiments±SD. 1-way ANOVA was performed among the data sets: 1) vehicle vs PARPi, 2) vehicle vs LiCl, 3) vehicle vs PARPi+LiCl, 4) PARPi vs PARPi+LiCl, 5) LiCl vs LiCl+PARPi*p<0.001. b) RT-qPCR data showing expression levels of c-Myb in response to PARPi, LiCl or PARPi+LiCl treatment. Data normalized against Gapdh levels in untreated MLL-AF9. Data represents means of four independent experiments±SD. 1-way ANOVA test was performed among the data sets as described in FIG. 6a *p<0.001. c) Relative colony number of leukemic cells surviving to PARPi, LiCl or combined PARPi+LiCl treatment. The number of colonies surviving to seven days incubation with drug treatment was normalized against the vehicle control. Data represents means of four independent experiments±SD. 1-way ANOVA was performed among the data sets as described in FIG. 6a *p<0.001. d) RT-qPCR data showing expression levels of c-Myb in response to PARPi, LiCl or PARPi+LiCl treatment. Data is normalized against Gapdh and untreated MLL-AF9. Data represents means of three experiments±SD. 1-way ANOVA test was performed among the data sets as described in FIG. 6b p<0.01. e) Giemsa-MayGrunwald staining of leukemic cells over-expressing HOXA9. f) The percentage of pre-LSC and LSCs undergoing differentiation characterised by morphology (upper panel) and NBT-positive cells (lower panel) following treatment with PARPi, LiCl or in combination for 4 days. 1-way ANOVA was performed among data set as described in FIG. 6a. *p<0.05 ***p<0.001. g) Kaplan-Meier survival curves of C57Bl/6 mice transplanted with MLL-AF9 leukemic cells pre-treated in liquid culture with Olaparib, LiCl or Olaparib+LiCl for three days before transplantation (vehicle n=4, Olaparib n=5, LiCl n=5, Olparaib+LiCl n=10). During of in vivo treatment is indicted in grey. Log-rank (Mantel-Cox) test was performed between the curves representing the vehicle and the treated groups. p<0.001 for comparison between survival curve representing vehicle and survival curve representing Olaparib+LiCl treatment. h-i) Relative proliferation of primary human MLL samples from h) AML1 (t11;17) and i) AML-2 (t6;11) with LiCl (8 mM), PARPi (1 uM Olaparib) or the combined PARPi+LiCl treatment. Cells were counted by trypan blue exclusion 5 days after PARPi treatment. The data show the fold change in cell number relative to day 0. Data represents means of at least two independent experiments±SD. 1-way ANOVA test was performed among the data sets as described in FIG. 6a *p<0.05; p<0.01; *p<0.001. j) Giemsa-MayGrunwald staining of human leukemic cells upon indicated treatments. k) The percentage of primary leukemic cells undergoing differentiation characterised by morphology (left panel) and NBT positive cells (right panel) following treatment with PARPi, LiCl or combination for 5 days. 1-way ANOVA was performed among the data sets as described in FIG. 6a. p<0.01 *p<0.001. 1) Results of in vivo imaging of disease progression of mice transplanted with AML1 primary human leukemic cells carrying luciferase reporter upon treatments. Left panel: Quantification of tumour burden measured as photon per second*10E+03 in NSG mouse 28 days after transplantation with primary human MLL cells. Right: Fold change in tumor burden between Day 28 and Day 21 after the transplant. Low level of tumor burden was detectable at Day 21. 1-way ANOVA was performed between vehicle and treated group. p<0.001. m) Kaplan-Meier survival curves of NSG mice transplanted with AML1 leukemic cells (vehicle n=6, Olaparib n=6, LiCl n=6, Olparaib+LiCl n=6). Duration of in vivo treatment is indicted in grey. Log-rank (Mantel-Cox) test was performed between the curves representing the vehicle and the treated groups. p<0.01 for comparison between survival curve representing vehicle and the survival curve representing Olaparib+LiCl treatment.

FIG. 7 (data related to FIG. 1): PARPi targets AML1-ETO and PML-RARα leukemic cells in vitro and in vivo.

a) Non-linear regression dose response curve of Olaparib treatment in normal mouse bone marrow c-Kit+ cells grown in methylcellulose for 7 days. Data represents means of three independent experiments±SD. The EC50, the half maximal effective concentration, of Olaparib for the cells is indicated. b) Colony morphology of c-Kit+ normal mouse bone marrow cells (Phase contrast microscopy magnification 40×). Representative pictures are shown. c) Absolute colonies number of leukemic cells surviving to Olaparib treatment corresponding to FIG. 1a. Data represents means of six independent experiments±SEM. d) Non-linear regression dose response curve of leukemic cells as indicated grown in methylcellulose for 7 days with escalating doses of PARPi. Data represents mean of three independent experiments are shown. The EC50 of Olaparib for the cells is indicated. e) Relative colonies number of leukemic cells surviving to PARPi, Veliparib. The number of colonies surviving to seven days incubation with Veliparib treatment was normalized against the untreated control. Data represents means of three independent experiments±SD. unpaired two-tailed t-test was performed between vehicle and Veliparib treated cells for each condition *p<0.001. f) Representative morphology of colonies indicated in Supplementary FIG. 1e (phase contrast microscopy, magnification 20×). g) Efficiency of Parp1 Knockdown (KD) in NIH3T3 cells transduced with retroviral vectors expressing shRNA targeting against mouse Parp1. RT-qPCR data showing expression of Parp1 in NIH3T3 transduced with sh-mParp1. Data represents means of two independent experiments±SD. 1-way ANOVA test was performed between empty vector and 1) sh-Parp1-A and 2) sh-Parp1-D *p<0.001. h) RT-qPCR showing Parp1 KD efficiency in primary cells transformed by the indicated fusion proteins. Data represents means of three independent experiments±SD. 1-way ANOVA test was performed between empty vector and 1) sh-Parp1-A and 2) sh-Parp1-D *p<0.05, p<0.01, *p<0.001. i) Absolute colonies numbers from the indicated primary transformed cells after shRNA-mediated Parp1 KD, corresponding to FIG. 1c. Data represents means of more than three independent experiments±SD. j-l) Flow cytometry analysis of bone marrow, spleen and liver harvested from sick mice transplanted with j) Kasumi, k) NB4-LR2 cell and l) THP1 respectively confirming level of engraftment. m-o) Giemsa-MayGrunwald staining of cells harvested from bone marrow, spleen or tumor of sick mice succumbed transplanted with m) Kasumi, n) NB4-LR2 and o) THP1 respectively. Bright field microscopy (40×). Representative pictures are shown. p) Non-linear regression dose response curve of primary AML patient cells to Olaparib. Primary patients cells were treated with PARPi for 5 days. Data represents means of three independent experiments±SD. q) EC50 of MLL, APL and AML-ETO primary patient samples to Olaparib. 1-way ANOVA was performed between 1) MLL and APL patients samples 2) MLL and AML1-ETO patients samples. **p<001.

FIG. 8 (data related to FIG. 2): PARPi induces differentiation, senescence, and apoptosis of AML1-ETO and PML-RARα leukemic cells a) Proliferation of pre-leukemic cells in the presence and absence of PARPi in methylcellulose at indicated time point. b) Giemsa-MacGrunwald staining of primary transformed cells with PARPi treatment at indicated time points. Representative pictures are shown. c) Percentage of differentiated cells counted according to morphology from figures shown in panel (b). Unpaired two-tailed t-test was performed between cells treated with vehicle or PARPi for 2, 4 and 6 days. *p<0.01, *p<0.001. d) Percentage of NBT positive cells. Data represents means of three independent experiments±SD. Unpaired two-tailed t-test was performed between cells treated with vehicle or PARPi for 2, 4 and 6 days. *p<0.001. e) Representative cell cycle profiles related to FIG. 2c. f) Representative FACS profile (Annexin V/PI) of pre-leukemic cells treated with PARPi related to FIG. 2i. g) Detection of senescent cells by β-galactosidase staining in human leukemic cell lines after 72 hrs of PARPi treatment. h) Quantification of percentage of β-galactosidase positive in human leukemic cells following PARPi treatment. Data represents means of two independent experiments±SD. Unpaired t-test was performed between vehicle and PARPi treated cells, *p<0.001. i) Quantification of apoptotic cells in human leukemic cell lines in percentage upon 4 days PARPi treatment. Data represents means of four independent experiments, ±SD. Unpaired two-tailed t-test was performed between vehicle and PARPi *p<0.001. j) Giemsa-Mayrunwald staining of human primary AML cells upon 1 µM Olaparib treatment for 5 days. The red arrow indicates the differentiated cells. k) Quantification of morphologically differentiated cells relating to panel 2j. Data represents means of two independent experiments±SD. Unpaired t-test was performed between cells treated with vehicle and PARPi **p<0.01. l) Percentage of NBT positive cells after PARPi treatment for 5 days. Data represents mean of three independent experiments±SD. Unpaired t-test test was performed between cells treated with vehicle and PARPi *p<0.05, ***p<0.001.

FIG. 9 (data related to FIG. 3): AML1-ETO and PML-RARα cells show a defect in HR pathway and accumulate DNA damage in response to PARPi treatment.

a) Western blot showing endogenous PARP1 co-immunoprecipitates with APLF (positive control) but not the oncofusion proteins in transfected 293T cells. b-e) RT-qPCR showing the effect of Parp1 KD on b) AML1-ETO, c) PML-RARα, d) MLL-AF9 and e) E2A-PBX target genes. Data represents means of two independent experiments±SD. 1-way ANOVA test was performed between 1) Scrambled and shParp1-A; 2) Scrambled and shParp1-D. *p<0.05, **p<0.01. f) The percentage of cells with >10 γH2AX foci±SEM in untreated condition is shown, and exhibits similar results by counting >6 γH2AX foci in FIG. 3b. 1-way ANOVA was performed between: 1) AML1-ETO and E2A-PBX, 2) PML-RARα and E2A-PBX, 3) MLL-AF9 and E2A-PBX, 4) AML1-ETO and MLL-AF9, 5) PML-RARα and MLL-AF9 (n=7, *p<0.05, p<0.01, *p<0.001). g-j) Time-course analysis of PARPi induced γH2AX and RAD51 foci by immunofluorescence microscopy in g) AML1-ETO, h) PML-RARα, i) MLL-AF9 and j) E2A-PBX cells. The panels show the nuclei in blue, γH2AX foci in green and RAD51 foci in red. k). The percentage of γH2AX positive cells (>6 foci) 0 (white bars), 6 (yellow bars) and 24 hrs (red bars) upon PARPi treatment is shown. 1-way ANOVA was performed between untreated and 1) 6 hr and 2) 24 hr (n=4 *p<0.05, *p<0.001). l) The figure shows the percentage of RAD51 positive cells (>10 foci), 0 (white bars), 6 (yellow bars) and 24 hrs (red bars) upon PARPi treatment. 1-way ANOVA test was performed between: 1) untreated and 6 hrs and 2) untreated and 24 hrs post treatment (n=4, *p<0.001). Consistent results were obtained by counting >6 Rad51 foci in FIG. 3d. m) Cell cycle analysis of indicated primary transformed cells treated with vehicle or PARPi for 6 hrs (left) and 24 hrs (right). n) Immunofluorescence microscopy for γH2AX foci in untreated human cells with nuclei in blue (DAPI) and γH2AX foci in green (representative cells). o) The percentage of cells with >6 γH2AX foci±SD in untreated condition. 1-way ANOVA was performed between: 1) Kasumi and THP1 and 2) NB4 and THP1 p<0.01 p) Time-course analysis of PARPi induced γH2AX and RAD51 foci by immunofluorescence microscopy in human leukemic cell lines. The panels show the nuclei in blue, γH2AX foci in green and RAD51 foci in red (representative cells). q) The percentage of RAD51 positive human cells (>6 foci) 0 (white bars), 6 (yellow bars) and 24 hrs (red bars) upon PARPi treatment. 1-way ANOVA test was performed between untreated and 6 hr (n=4 p<0.01). r) The percentage of cells with γH2AX/RAD51 ratio >2, Unpaired t-test was performed with **p<0.01. s) Box-plot showing normalized expression of DNA repair-associated genes in AML patient samples from Verhaak et al., Haematologica 2009. AML1-ETO n=37, APL n=25, MLL n=35). *p<0.05, p<0.01, *p<0.001, NS=Not Significant, p values were calculated using unpaired t-Test.

FIG. 10 (data related to FIG. 4): HOXA9 modulates the sensitivity to PARPi a) RT-qPCR data showing expression of human HOXA9 in U937 cell lines carrying Zinc (Zn)-inducible AML1-ETO or PML-RARα 6 hrs after the induction. Data represents means of two independent experiments±SD. 2-way ANOVA test was performed between untreated and Zinc induced cells (**p<0.01). b) RT-qPCR data showing expression of mouse Hoxa9 in primary transformed cell line expressing inducible MLL-AF9-ER after tamoxifen withdrawal at indicated time points. Data represents means of three independent experiments±SD. 1-way ANOVA test was performed between Day 0 (untreated) and Day 3, Day 0 and Day 5 (*p<0.05, *p<0.001). c) Normalized expression of HOXA9 in AML patient samples from Verhaak et al., Haematologica 2009 (Left) and Valk et al., NEJM 2004 (Right), ***p<0.001, NS=Not Significant, p-values were calculated using unpaired t-test. d) Semi-quantitative PCR showing the genotype of cells generated in wild type and Hoxa9−/− background. e) Absolute colony number of primary transformed cells generated in wild-type or Hoxa9−/− background surviving to PARPi. Data represent means of five independent experiments±SEM, corresponding to data in FIG. 4a. f) Flow cytometry analysis (c-Kit/Gr1 and c-Kit/Mac1) of primary transformed cells before and after PARPi treatment. g) Kaplan-Meier survival curves of C57Bl/6 mice serially transplanted with MLL-AF9 cells generated in Hoxa9−/−(bold black line, n=5) and wild type (bold red line, n=3) background. The leukemic cells harvested from mice succumbed with leukemia (primary recipients) were transplanted in C57Bl/6 recipient mice (secondary transplants, dotted lines, n=9 and n=3). h) Flow cytometry analysis (CD45.1/CD45.2, Gr1/c-Kit, Gr1/Mac1) of bone marrow harvested from mice treated as indicated. wild type (left) and Hoxa9−/−(right). Engrafted cells were labelled by CD45.1. i) Absolute colony number of primary transformed cells over-expressing HOXA9 surviving to PARPi, corresponding to data shown in FIG. 4h. Data represent means of three independent experiments±SEM. j) RT-qPCR data showing expression of Hoxa9 and their respective oncogenes in transformed mouse cells before and after Hoxa9 over-expression. Data represents means of two independent experiments±SD. Unpaired two tailed t-test was performed between wild type vs Hoxa9 over-expression n=4, *p<0.05, p<0.01, *p<0.001.

FIG. 11 (related to FIG. 5): HOXA9 modulates PARPi sensitivity a-b) Gene Sets Enrichment Analysis (GSEA). Gene sets associated with DNA repair (a) and double strand break repair (b) are enriched in the transcriptional profile of mouse myeloblasts over-expressing HOXA9. c) RT-qPCR of DDR genes in MLL-AF9 wild type and MLL-AF9 Hoxa9 KO cells. Gene expressions in MLL-AF9 wild-type were normalized to 1. Data represents means of two independent experiments±SD. 1-way ANOVA test was performed between untreated and PARPi treated cells (***p<0.001).

Figure 6B:
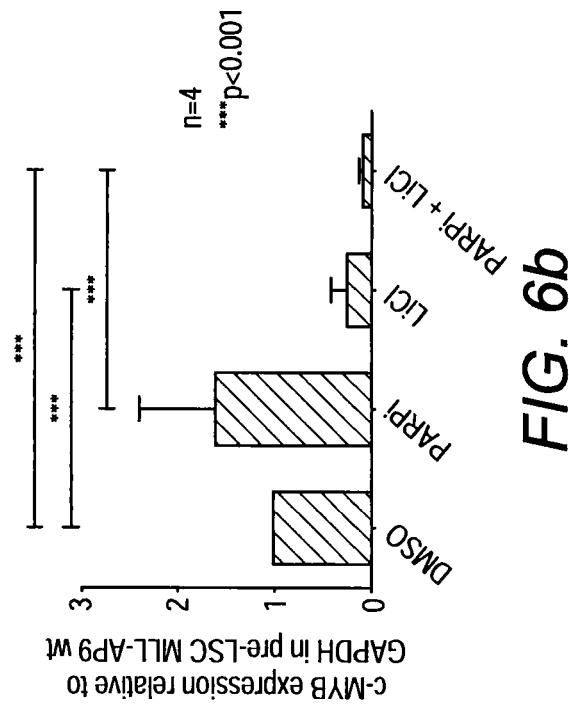
Figure 6D:
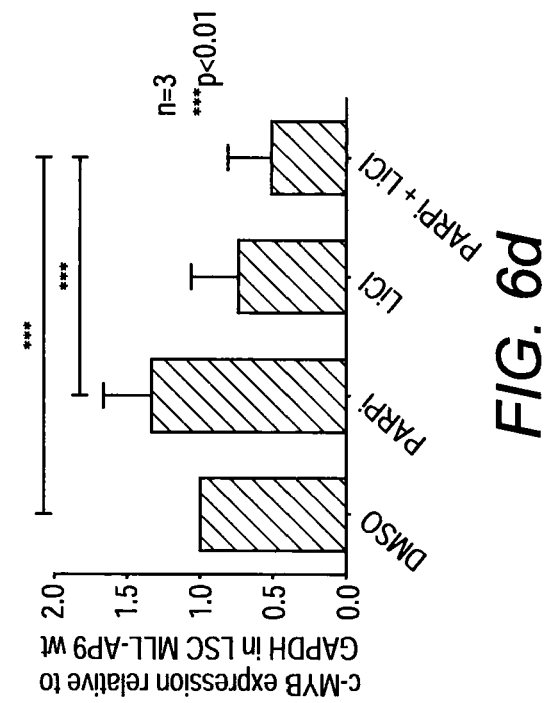
Figure 6A:
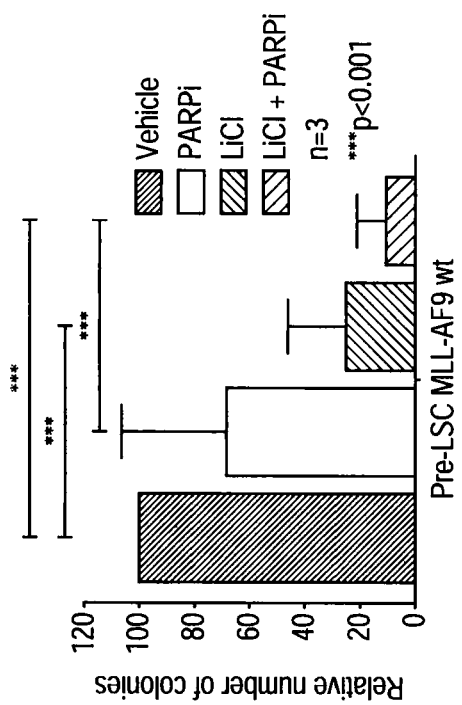

FIG. 12 (data related to FIG. 6): Combined PARPi and GSK3i treatment impairs in vivo survival of MLL leukemia a) Non-linear regression dose response curve of GSK3i (LiCl) in c-Kit+ normal mouse bone marrow cells grown in methylcellulose. Colony number was acquired after 7 days of culture. Data represents means of three independent experiments±SD. EC50 (50% of maximal effective concentration) are indicated in the FIG. b-c) Absolute colony number of b) pre-LSC c) LSC surviving to PARPi, LiCl or combined PARPi+LiCl treatment. Relative number of colony is shown in FIGS. 6a and c. Data represents means of three independent experiments±SEM. 1-way ANOVA test. p<0.01, *p<0.001. Data represents means of four independent experiments±SEM. 1-way ANOVA test *p<0.001. d) Flow cytometry analysis (CD45.1/CD45.2, c-kit/Gr1, Gr1/Mac1) of bone marrow harvested from C57Bl6 mice transplanted with CD45.1 positive MLL-AF9 cells. e) Giemsa-MayGrunwald staining of cells harvested from bone marrow of sick animals with indicated treatments. f) Relative proliferation of human leukemic cells THP1 to LiCl, PARPi or combined PARPi+LiCl treatment. Cells were counted on day 5 after treatment by trypan blue exclusion. The data show the fold change in cell number relative to day 0. Data represents means of at least two independent experiments±SD. 1-way ANOVA Test was performed among the data sets: 1) untreated vs PARPi, 2) untreated vs LiCl, 3) untreated vehicle vs PARPi+LiCl, 4) PARPi vs PARPi+LiCl, 5) LiCl vs LiCl+PARPi p<0.01; ***p<0.001. g) Giemsa-MayGrunwald staining of human THP1 cells with indicated treatments. h) Pictures showing the tumor burden of each treatment group that are visualized and quantified in FIG. 6l. i) Flow cytometry analysis (CD45/CD33) of bone marrow harvested from sick NSG mice transplanted with primary AML1 cells undergone indicated treatments. j) Giemsa-MayGrunwald staining of cells harvested from bone marrow of sick mice with indicated treatment.

Figure 13:
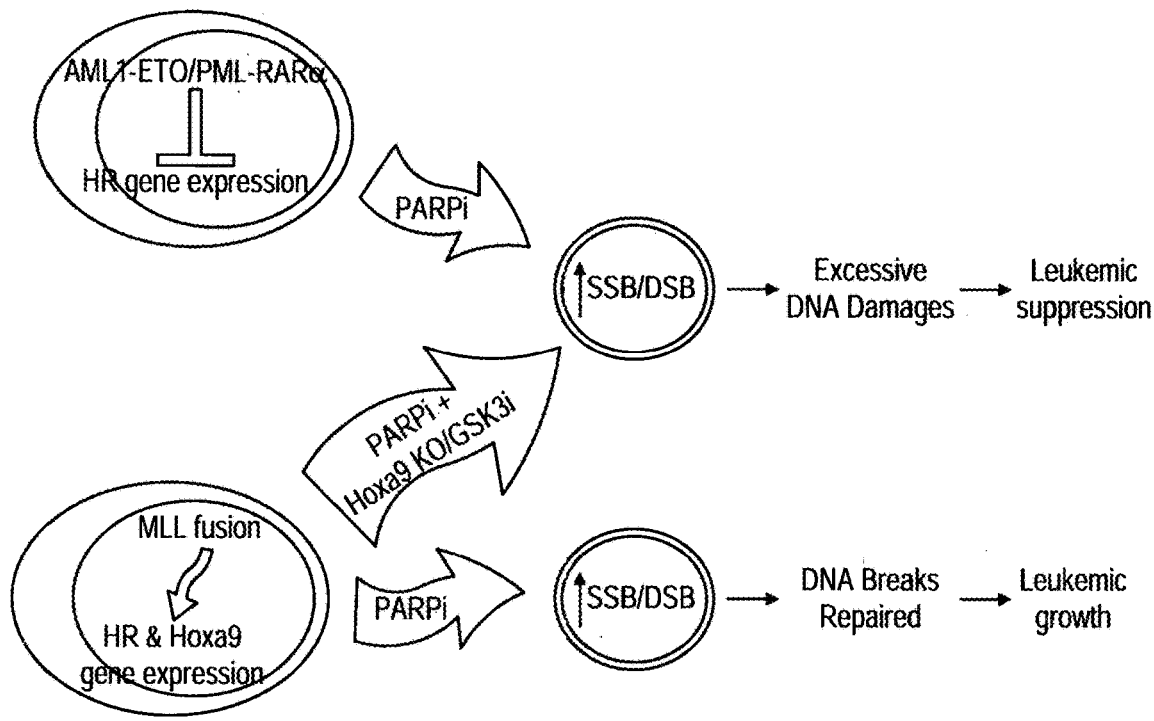

FIG. 13: Proposed models for PARPi treatments in different AML subtypes driven by oncogenic transcription factors.

AML1-ETO and PML-RARα suppress the expression of DDR gene and HR efficiency, which make them sensitive to PARPi treatment. In contrast, leukemia driven by MLL-fusion expressing a high level of HR genes including HOXA9 is refractory to PARPi. Inactivation of HOXA9 by genetic mean or GSK3i can re-sensitize MLL leukemia to PARPi, and suppresses disease development.

Figure 14:
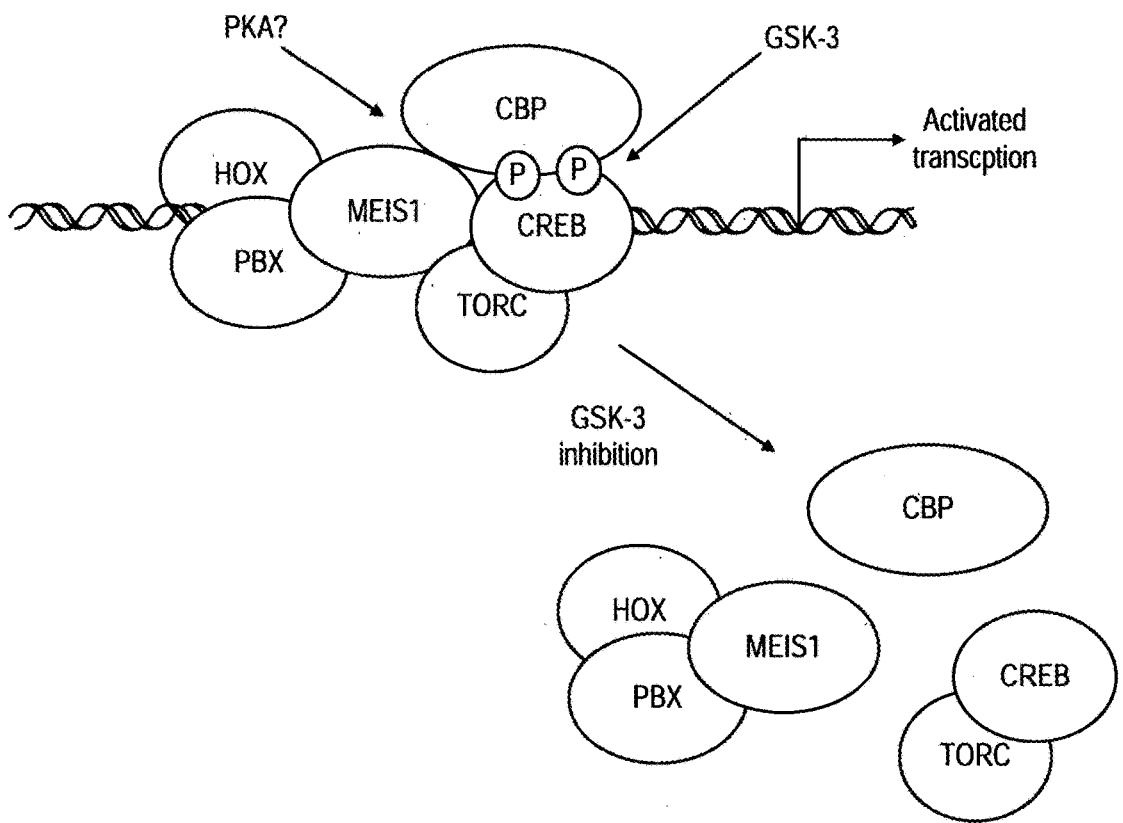
Figure 15A:
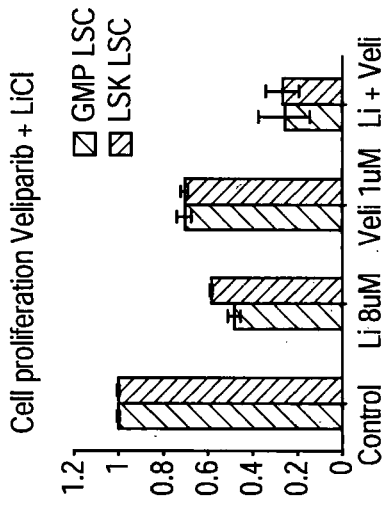
Figure 15B:
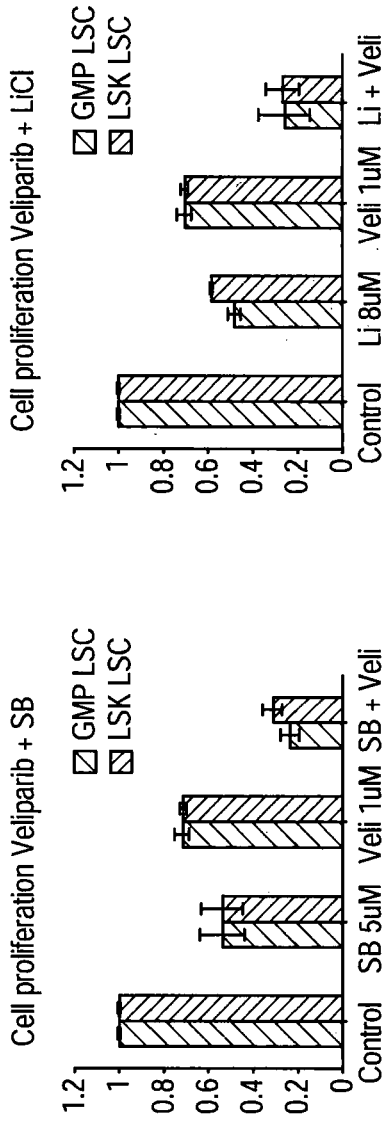
Figure 15C:
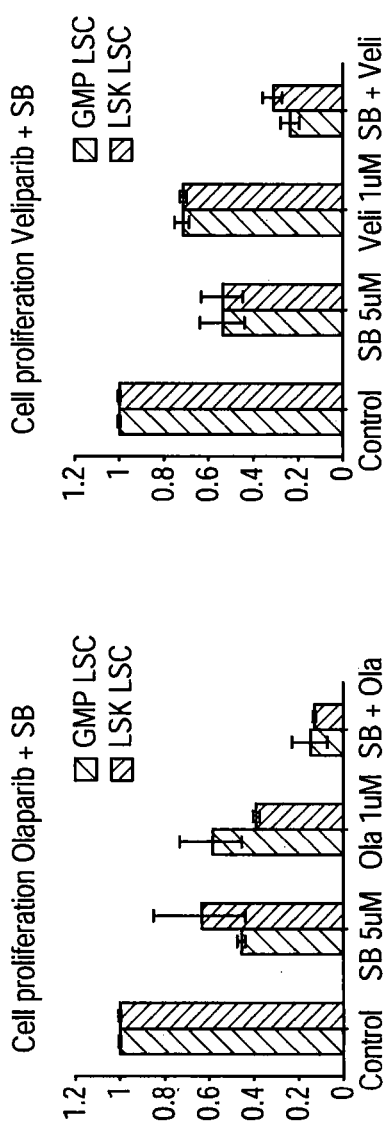
Figure 15D:
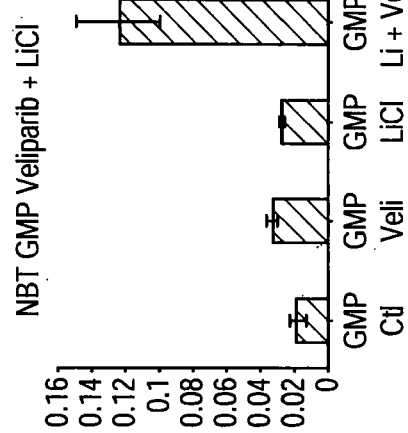
Figure 15E:
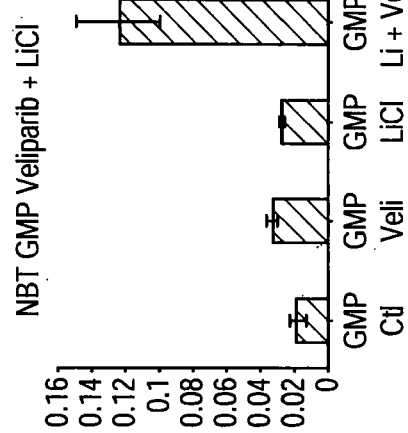
Figure 15F:
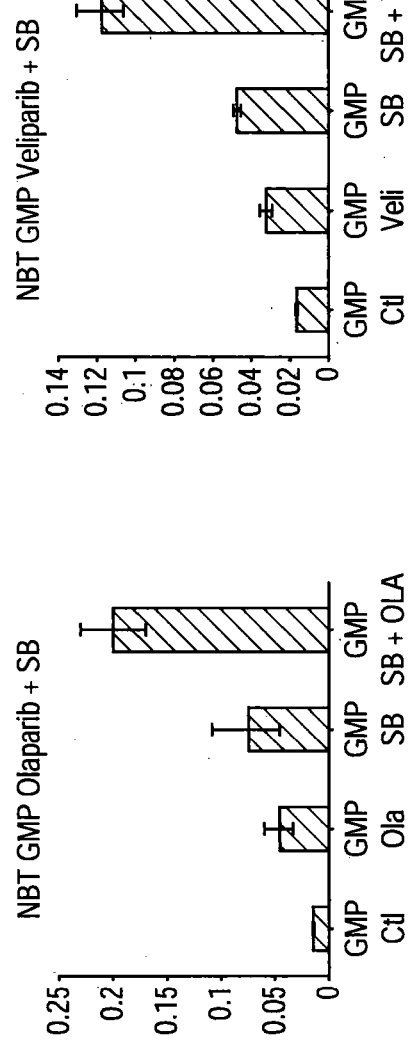
Figure 15O:
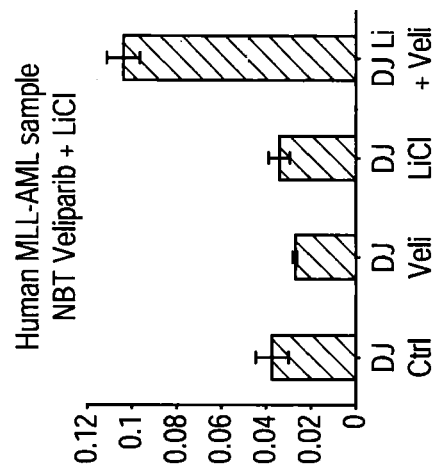
Figure 15N:
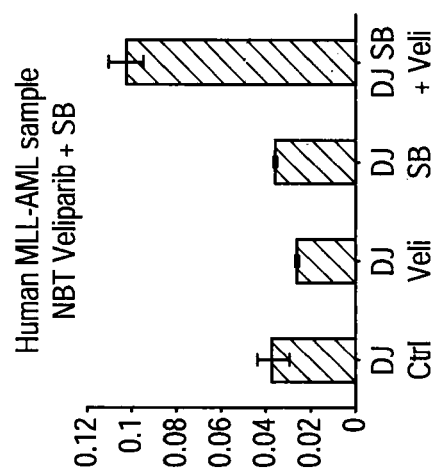
Figure 15M:
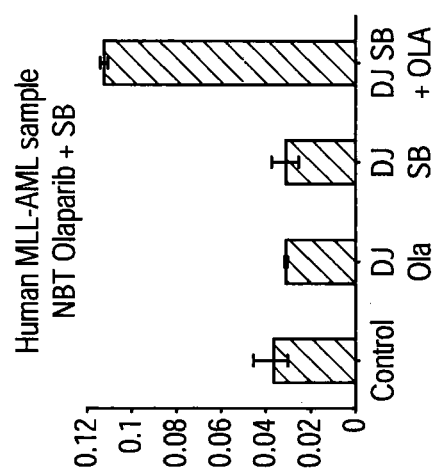
Figure 16A:
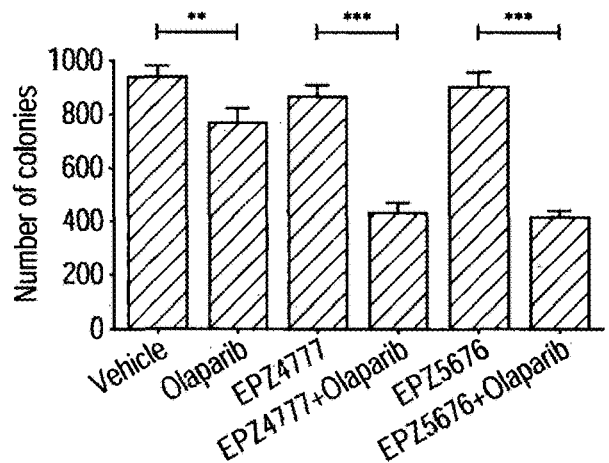
Figure 16B:
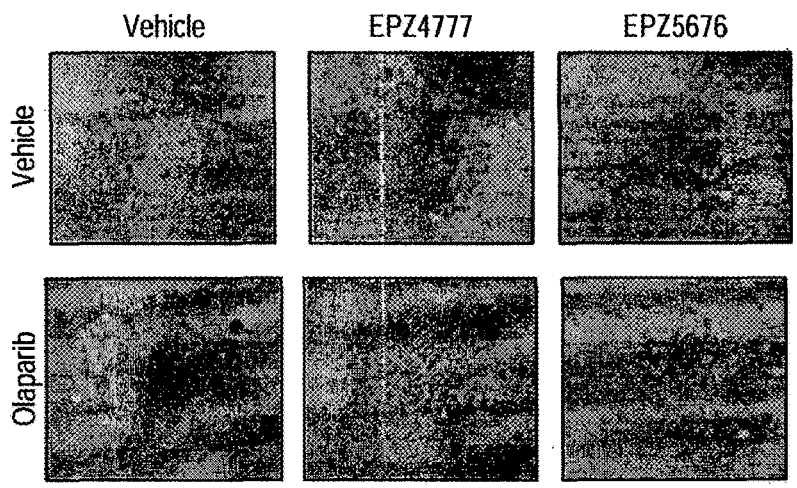
Figure 16C:
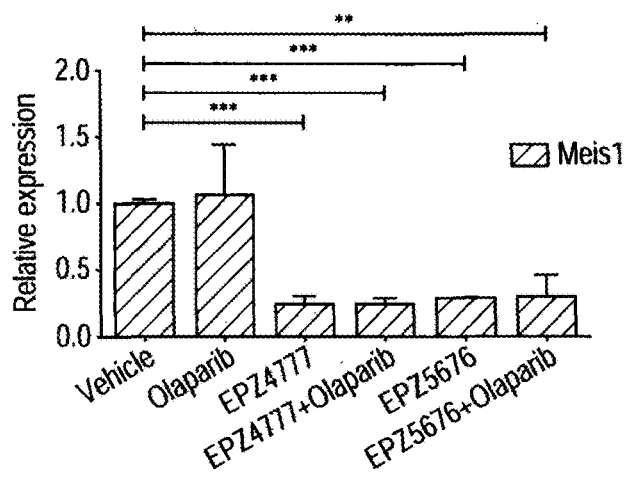
Figure 16D:
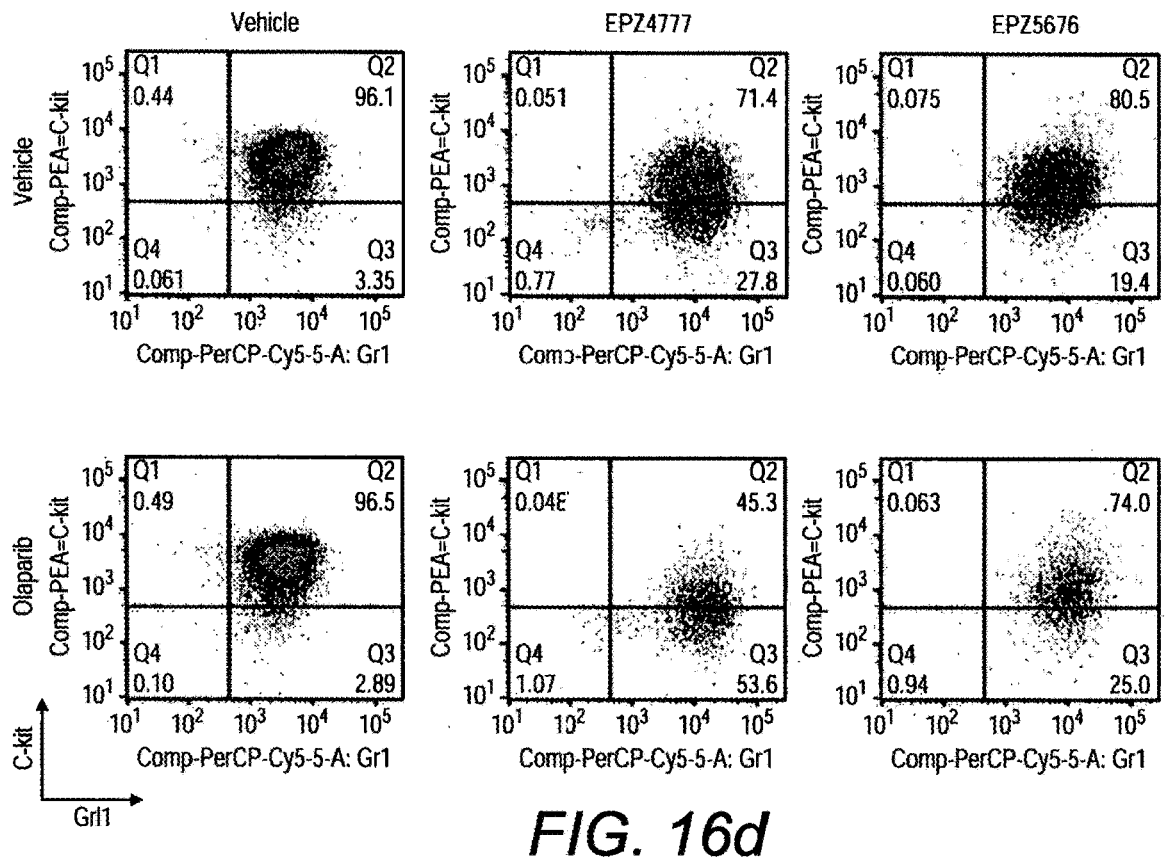
Figure 16E:
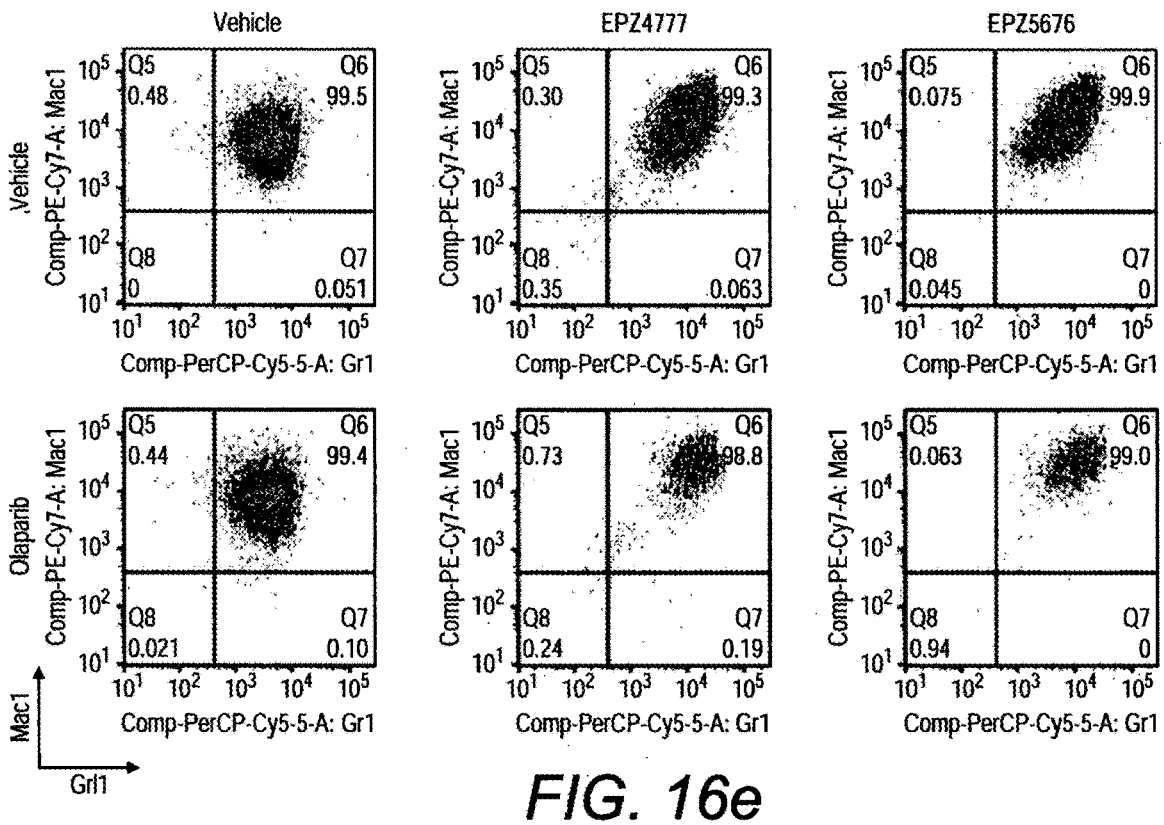

FIG. 14: Downstream Hoxa9 signalling pathway. Figure shows proteins involved in the activation of transcription in complex with Hoxa9 protein. PBX: pre-B-cell leukemia homeobox transcription factor; TORC (transducer of regulated CREB activity); CREB (cAMP response element-binding protein); CBP (CREB-binding protein); GSK-3 (glycogen synthase kinase-3).

FIG. 15: Specific GSK3i, SB216763, and LiCl syngergize with PARPi (olaparib and veliparib) to suppress MLL leukemic cell growth. Inhibition of mouse MLL leukemic cell growth by A) SB216763 and Olaparib; B) SB216763 and Veliparib; C) Veliparib and LiCl on GMP progenitor or LSK stem cell-derived leukemic stem cells (LSC). Induction of leukemic cell differentiation by D) Olaparib and SB216763; E) Veliparib and SB216763; F) Veliparb and LiCl on GMP-derived LSC. Induction of leukemic cell differentiation by G) Olaparib and SB216763; H) Veliparib and SB216763; I) Veliparb and LiCl on LSK-derived LSC. Inhibition of primary human MLL leukemic cells by J) SB216763 and Olaparib; K) SB216763 and Veliparib; L) Veliparib and LiCl. Induction of leukemic cell differentiation by M) Olaparib and SB216763; N) Veliparib and SB216763; O) Veliparb and LiCl on primary human MLL leukemic cells.

FIG. 16: Inhibition of Dot1L synergies with PARPi to suppress MLL leukemic cells. A) Two independent DOT1L inhibitors, EPZ4777 and EPZ5676, can synergize with PARPi, olaparib in suppressing clonogenic potentials of primary cells transformed by MLL-AF9. B) Typical colony morphology of vehicle, DOT1L inhibitors, PARPi, or their combination treated cells. MLL leukemic cells treated with DOT1L and PARP inhibitors formed significantly smaller and diffuse colonies. C) Measurement of expression of MLL downstream target, Meis1 by RT-qPCR upon DOT1L or/and PARPi treatment in MLL transformed cells. DOT1L inhibitors suppress expression of Meis1, which is required for Hoxa9 transcription functions. D-E) Immunophenotypic analysis of MLL leukemic cells showed significant differentiation upon DOT1L and PARPi combination treatment. FACS plots depict the expression of D) c-kit and Gr-1; E) Mac1 and Gr-1 in MLL leukemic cells upon the indicated treatments.

Figure 17:
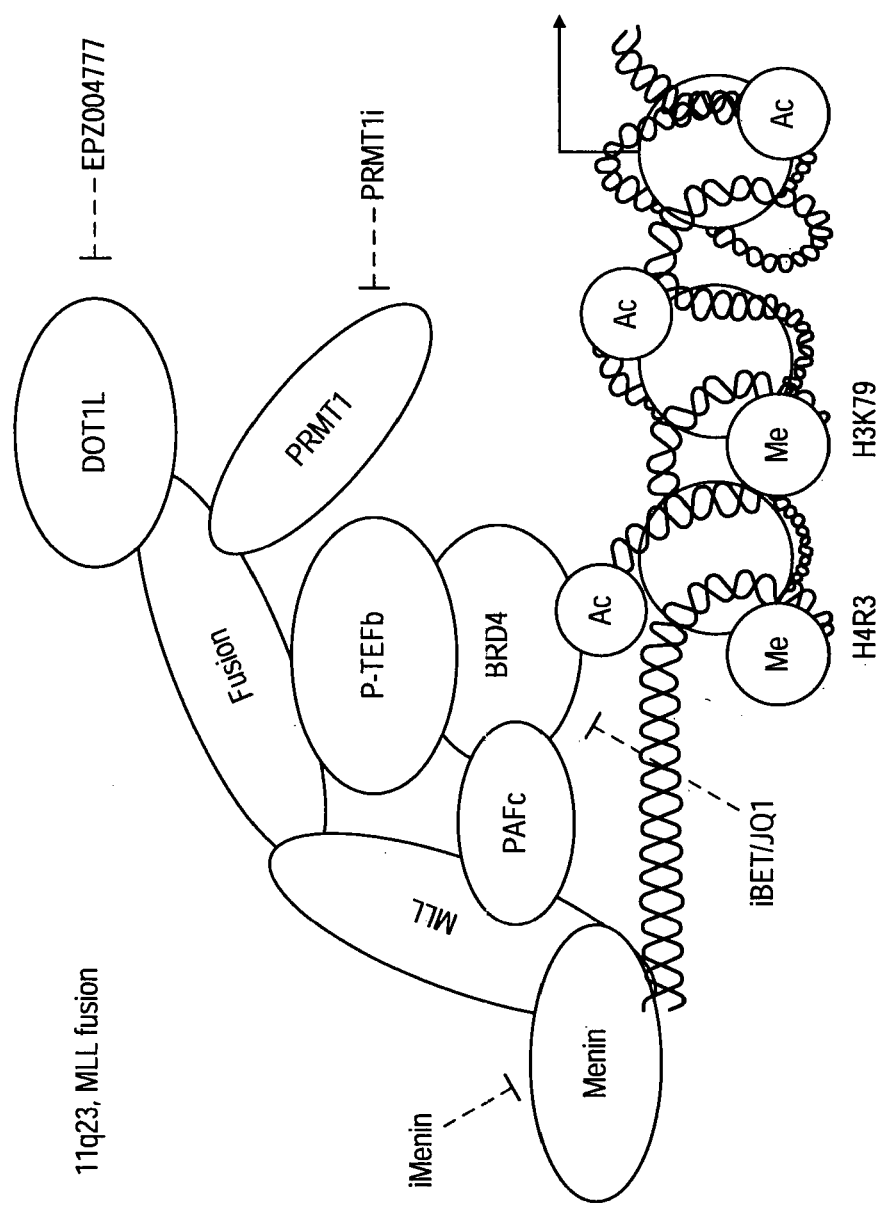

FIG. 17: Upstream Hoxa9 signalling pathway. Figure shows proteins involved in the activation of transcription of the Hoxa9 gene. DOT1L: disrupter of telomeric silencing 1-like; MLL: mixed lineage leukemia; PRMT1: protein arginine N-methyltransferase 1; P-TEFb: positive transcription elongation factor b; BRD4: bromodomain-containing protein 4; PAFc: polymerase-associated factor complex.

Figure 18A:
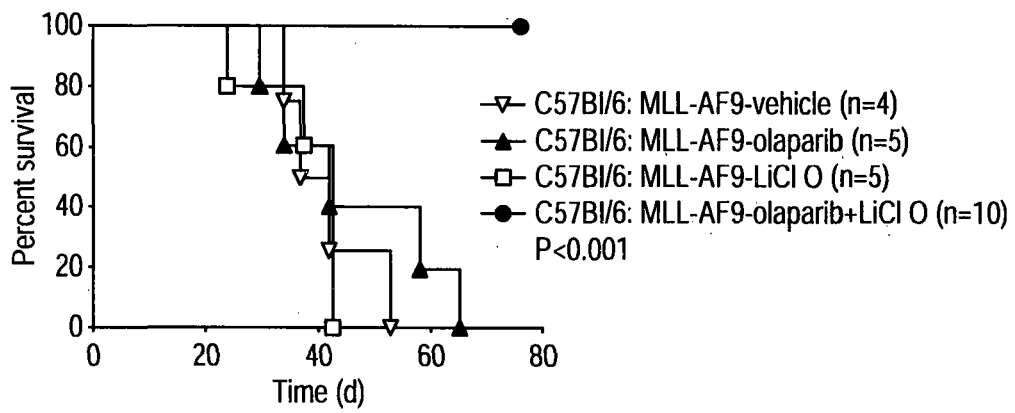
Figure 18B:
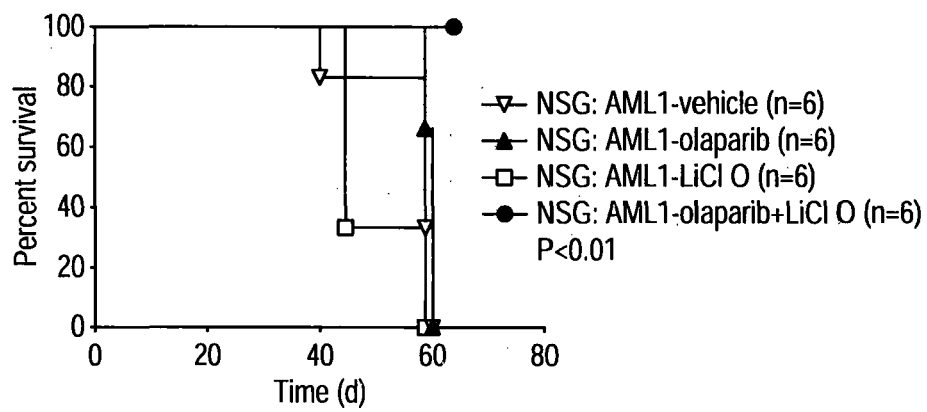
Figure 18C:
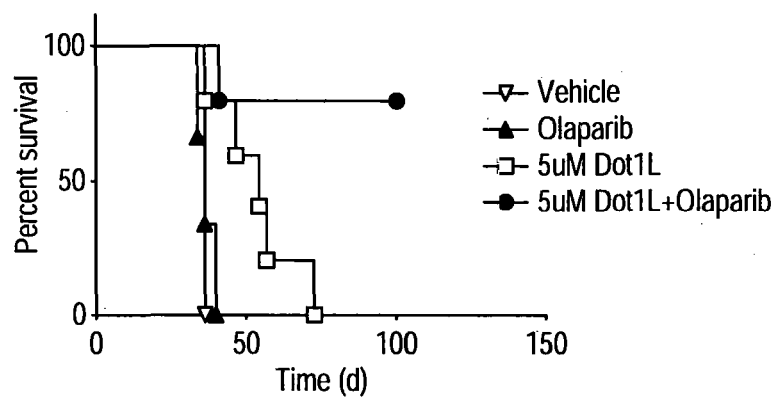

FIG. 18: Survival analysis of mice transplanted with MLL leukemic cells under PARPi combination treatments. A) Survival of C57BL6 syngeneic mice transplanted with MLL-AF9 mouse leukemic cells under treatment with vehicle, PARPi (Olaparib), GSK3i (Li2CO3) or the combination. B) Survival of NSG mice transplanted with primary human leukemic cells with MLL gene rearrangement (AML1) under treatment with vehicle, PARPi (Olaparib), GSK3i (Li2CO3) or the combination. C) Survival of C57BL6 syngeneic mice transplanted with MLL-AF9 mouse leukemic cells under treatment with vehicle, PARPi (Olaparib), DOT1Li (EPZ drug) or the combination.

DETAILED DESCRIPTION OF THE INVENTION

Embodiments of the present invention are based on the finding that AML leukaemia in subjects expressing mutated MLL transcription factors can be sensitised to treatment with PARP inhibitors by inhibition of Hoxa9 signalling, e.g. via inhibition of GSK3 or DOT1L. Accordingly the present invention relates in one aspect to combined treatments for MLL leukemia comprising co-administration of PARP inhibitors (PARPi) and GSK3 inhibitors (GSK3i), DOT1L inhibitors (DOT1Li) or other Hoxa9 inhibitors.

Poly-(Adp-Ribose)-Polymerase Inhibitors

PARP1 is a nuclear protein that senses single and double strand DNA breaks (SSB and DSB) catalyzing the addition of poly ADP ribose to itself, histones, topoisomerase I, DNA protein kinase (DNA-PK), XRCC1 and other proteins involved in DNA repair (Brightwell and Shall 1971, Biochem. J. 125(3):67P; Krishnakumar and Kraus 2010, Mol. Cell. 39(1):8-24). When PARP-1 is inhibited, it can be trapped on the SSB intermediate, preventing the ligation step and inducing accumulation of SSB that then collapse replication forks in DSB (Bryant, Schultz et al. 2005, Nature 434(7035):913-917); Farmer, McCabe et al. 2005, Nature 434(7035):917-921); Helleday, Petermann et al. 2008, Mol Oncol. 5(4):387-393). Seventeen PARP proteins have been identified so far, but not all of them are enzymatically active (Rouleau, Patel et al. 2010, Nat Rev Cancer 10(4):293-301).

In general, the PARP inhibitor may be any agent that can inhibit the activity of PARP, for example, any one or more of PARP 1-17. Preferably the agent is a small molecule inhibitor. In one embodiment, the PARP inhibitor inhibits the activity of PARP1 and/or PARP2. PARP inhibitors may be selected from compounds having PARP inhibitory activity and one of the following general structures: nicotinamides, such as 5-methyl nicotinamide and O-(2-hydroxy-3-piperidino-propyl)-3-carboxylic acid amidoxime, and analogues and derivatives thereof; benzamides, including 3-substituted benzamides such as 3-aminobenzamide, 3-hydroxybenzamide 3-nitrosobenzamide, 3-methoxybenzamide and 3-chloroprocainamide, and 4-aminobenzamide, 1,5-di[(3-carbamoylphenyl)aminocarbonyloxy]pentane, and analogues and derivatives thereof; isoquinolinones and dihydroisoquinolinones, including 2H-isoquinolin-1-ones, 3H-quinazolin-4-ones, 5-substituted dihydroisoquinolinones such as 5-hydroxy dihydroisoquinolinone, 5-methyl dihydroisoquinolinone, and 5-hydroxy isoquinolinone, 5-amino isoquinolin-1-one, 5-dihydroxyisoquinolinone, 3,4 dihydroisoquinolin-1(2H)-ones such as 3,4 dihydro-5-methoxy-isoquinolin-1(2H)-one and 3, 4 dihydro-5-methyl-1(2H)isoquinolinone, isoquinolin-1(2H)-ones, 4,5-dihydroimidazo[4,5,1-ij]quinolin-6-ones, 1,6-naphthyridine-5(6H)-ones, 1,8-naphthalimides such as 4-amino-1,8-naphthalimide, isoquinolinone, 3,4-dihydro-5-[4-1(1-piperidinyl)butoxy]-1(2H)-isoquinolinone, 2,3-dihydrobenzo[de]isoquinolin-1-one, 1-11b-dihydro-[2H]benzopyrano[4,3,2-de]isoquinolin-3-one, and tetracyclic lactams, including benzpyranoisoquinolinones such as benzopyrano[4,3,2-de]isoquinolinone, and analogues and derivatives thereof; benzimidazoles and indoles, including benzoxazole-4-carboxamides, benzimidazole-4-carboxamides, such as 2-substituted benzoxazole 4-carboxamides and 2-substituted benzimidazole 4-carboxamides such as 2-aryl benzimidazole 4-carboxamides and 2-cycloalkylbenzimidazole-4-carboxamides including 2-(4-hydroxphenyl)benzimidazole 4-carboxamide, quinoxalinecarboxamides, imidazopyridinecarboxamides, 2-phenylindoles, 2-substituted benzoxazoles, such as 2-phenyl benzoxazole and 2-(3-methoxyphenyl)benzoxazole, 2-substituted benzimidazoles, such as 2-phenyl benzimidazole and 2-(3-methoxyphenyl) benzimidazole, 1,3,4,5 tetrahydro-azepino[5,4,3-cd]indol-6-one, azepinoindoles and azepinoindolones such as 1,5 dihydro-azepino[4,5,6-cd]indolin-6-one and dihydrodiazapinoindolinone, 3-substituted dihydrodiazapinoindolinones such as 3-(4-trifluoromethylphenyl)-dihydrodiazapinoindolinone, tetrahydrodiazapinoindolinone and 5,6-dihydroimidazo[4,5,1-j,k][1,4]benzodiazopin-7(4H)-one, 2-phenyl-5,6-dihydro-imidazo [4,5,1-jk][1,4]benzodiazepin-7(4H)-one and 2,3, dihydro-isoindol-1-one, and analogues and derivatives thereof; phthalazin-1(2H)-ones and quinazolinones, such as 4-hydroxyquinazoline, phthalazinone, 5-methoxy-4-methyl-1(2) phthalazinones, 4-substituted phthalazinones, 4-(1-piperazinyl)-1(2H)-phthalazinone, tetracyclic benzopyrano[4,3,2-de]phthalazinones and tetracyclic indeno[1,2,3-de]phthalazinones and 2-substituted quinazolines, such as 8-hydroxy-2-methylquinazolin-4-(3H)one, tricyclic phthalazinones and 2-aminophthalhydrazide, and analogues and derivatives thereof; isoindolinones and analogues and derivatives thereof; phenanthridines and phenanthridinones, such as 5[H]phenanthridin-6-one, substituted 5[H]phenanthridin-6-ones, especially 2-, 3-substituted 5[H]phenanthridin-6-ones and sulfonamide/carbamide derivatives of 6(5H)phenanthridinones, thieno[2,3-c]isoquinolones such as 9-amino thieno[2,3-c]isoquinolone and 9-hydroxythieno[2,3-c]isoquinolone, 9-methoxythieno[2,3-c]isoquinolone, and N-(6-oxo-5,6-dihydrophenanthridin-2-yl)-2-(N,N-dimethylamino)acetamide, substituted 4,9-dihydrocyclopenta[lmn]phenanthridine-5-ones, and analogues and derivatives thereof; benzopyrones such as 1,2-benzopyrone 6-nitrosobenzopyrone, 6-nitroso 1,2-benzopyrone, and 5-iodo-6-aminobenzopyrone, and analogues and derivatives thereof; unsaturated hydroximic acid derivatives such as O-(3-piperidino-2-hydroxy-1-propyl)nicotinic amidoxime, and analogues and derivatives thereof; and pyridazines, including fused pyridazines and analogues and derivatives thereof.

Early generation PARPi had little specificity for individual PARPs and very high IC50 (half-maximal inhibitory concentration), driving significant off target effects. In contrast, olaparib is an oral competitive PARPi targeting the nicotinamide binding pocket of PARPI and PARP2 (Wahlberg, Karlberg et al. 2012, Nat Biotechnol 30(3):283-288). Developed by Kudos Pharmaceuticals and later by Astra Zeneca, its improved chemical structure increases its specificity and affinity to PARPI and PARP2.

Olaparib is one of the first PARPi to enter clinical trials and it has already been tested in phase I and phase II trials including breast, prostate and ovarian cancer patients carrying mutations in BRCA1 or BRCA2 genes, showing anti-tumour effect and side effects of grade 1 or 2 (Fong, Boss et al. 2009, N Engl J Med 361(2):123-134; Tutt, Robson et al. 2010, Lancet 376(9737):235-244). Tested in a phase II clinical trial in an untargeted population of ovarian cancer, Olaparib failed to show overall survival benefit compared to chemotherapy. Based on these results, in 2011 AstraZeneca decided not to, as previously planned, pursue a phase III clinical trial in hereditary BRCA1 and BRCA2 associated breast cancer, a controversial decision considering that these patients are the strongest candidates for PARPi. The results of the clinical trial in untargeted populations of ovarian cancer highlighted the importance of identifying patients carrying specific mutations who may benefit from the treatment. More recently, on April 2013 Astrazeneca announced a new Phase III trial of Olaparib for patients with BRCA mutated ovarian cancer, which is due in the end of the year. Olaparib and other PARPi are continuing to advance through clinical trials (see a complete list below), showing promising results in targeted populations of patients with "BRCAness phenotype" (Turner, Tutt et al. 2004, Lancet 376(9737):235-244).

Astra Zeneca: Olaparib (AZD2281) currently in phase I/II as single agent or combination with chemotherapy in various cancer types including breast, ovarian and colorectal cancers. Currently recruiting ovarian cancer patients carrying BRCA mutation for a phase III.

Abbott: Veliparib (ABT-888) currently in phase I/II in combination with chemotherapy or radiation in various metastatic or unresectable solid tumours including breast, ovarian and colorectal cancer, glioblastoma and melanoma or non-Hodgkin lymphoma; phase II for metastatic melanoma and breast cancer; currently recruiting prostate cancer patients carrying BRCA mutation for a phase III.

Cephalon: CEP-9722 currently in phase I/II in combination with temozolomide in advanced solid tumors and lymphoma. In phase III for non-small cell lung cancer.

Clovis Oncology: Rucaparib (AG014699, PF-01367338) currently in phase I/II in BRCA ½ mutant cancers and solid tumors; phase III for metastatic ovarian and breast cancer.

Eisai: E7016 currently in phase I in combination with temozolomide in advanced solid tumours.

BioMarin Pharmaceutical: BMIM-673 currently in phase I in solid tumours and advanced haematological cancer.

Inotek: INO-1001 currently in phase I in combination with temozolomide in melanoma.

Sanofi-Aventis: Iniparib (BSI-201) currently in phase III in combination with gemcitabine and carbpoplatin in breast and lung cancers; phase I/II: single agent or in combination with chemotherapy in various cancer types including glioma and ovarian cancers; Failed phase III clinical trial for triple negative breast cancer.

Tesaro Inc.: K4827 currently in phase I in advanced solid tumours or haematological disorders.

Accordingly, in embodiments of the present invention a PARP inhibitor such as one of those described above may be used. Preferably the PARP inhibitor shows inhibition of at least PARP1, e.g. with an IC50 of 100 µM or below, 10 µM or below, 1 µM or below, 100 nM or below, 10 nM or below, or 1 nM or below. Typically PARP inhibitors induce double strand breaks in DNA and cell death in cells in which homologous recombination is inactive (for instance due to mutations in DNA repair genes). Thus PARP inhibitors can be identified using corresponding cellular assays, including as described in the examples below. In embodiments of the present invention, the PARP inhibitor is preferably selected from olaparib (AZD2281, 4-[[3-[(4-cyclopropylcarbonyl)piperazin-4-yl]carbonyl)-4-fluorophenyl]methyl(2H)-phthalazin-1-one), veliparib (ABT-888, 2-((R)-2-methylpyrrolidin-2-yl)-1H-benzimidazole-4-carboxamide), CEP-9722 (a prodrug which is converted to 11-methoxy-4,5,6,7-tetrahydro-1H-cyclopenta[a]pyrrolo[3,4-c]carbazole-1,3(2H)-dione (CEP-8983)), rucaparib (AG014699, 8-Fluoro-2-{4-[(methylamino)methyl]phenyl}-1,3,4,5-tetrahydro-6H-azepino[5,4,3-cd]indol-6-one), E7016 (10-((4-Hydroxypiperidin-1-yl)methyl)chromeno[4,3,2-de]phthalazin-3(2H)-one), BMN-673 ((8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one), and INO-1001 (4-phenoxy-3-pyrrolidin-1-yl-5-sulfamoyl-benzoic acid), and analogues and derivatives thereof. Preferably the PARP inhibitor is olaparib or veliparib, more preferably olaparib.

Further suitable PARP inhibitors and assays for determining PARP inhibition are disclosed in, for example, U.S. Pat. No. 7,041,675, WO07/041357, WO2003/057699 U.S. Pat. No. 06,444,676; US 2006/0229289; US 2006/0063926; WO2006/033006; WO2006/033007; WO03/051879; WO2004/108723; WO2006/066172; WO2006/078503; US2007/0032489; WO2005/023246; WO2005/097750; WO2005/123687; WO2005/097750; U.S. Pat. Nos. 7,087,637; 6,903,101; WO2007/0011962; US 2007/0015814; WO2006/135873; US2007/0072912; WO2006/065392; WO2005/012305; WO2005/012305; EP412848; EP453210; EP454831; EP879820; EP879820; WO030805; WO03/007959; U.S. Pat. No. 6,989,388; US2006/0094746; EP1212328; WO2006/078711; U.S. Pat. Nos. 6,426,415; 6,514,983; EP1212328; US2004/0254372; US2005/0148575; US2006/0003987; U.S. Pat. No. 06,635,642; WO2001/16137; WO2004/105700; WO03/057145; WO2006/078711; WO2002/044157; US2005/6924284; WO2005/112935; US2004/6828319; WO2005/054201; WO2005/054209; WO2005/054210; WO2005/058843; WO2006/003146; WO2006/003147; WO2006/003148; WO2006/003150; WO2006/003146; WO2006/003147; US2007/0072842; U.S. Pat. No. 05,587,384; US2006/0094743; WO2002/094790; WO2004/048339; EP1582520; US2006/0004028; WO2005/108400; U.S. Pat. No. 6,964,960; WO2005/0080096; WO2006/137510; US2007/0072841; WO2004/087713; WO2006/046035; WO2006/008119; WO2006/008118; WO2006/042638; US2006/0229289; US2006/0229351; WO2005/023800; WO1991/007404; WO2000/042025; WO2004/096779; U.S. Pat. No. 06,426,415; WO02/068407; U.S. Pat. No. 06,476,048; WO2001/090077; WO2001/085687; WO2001/085686; WO2001/079184; WO2001/057038; WO2001/023390; WO01/021615; WO2001/016136; WO2001/012199; WO95/024379; WO2002/36576; WO2004/080976; Banasik et al. J. Biol. Chem., 267:3, 1569-75 (1992); Banasik et al. Molec. Cell. Biochem. 138:185-97 (1994); Cosi (2002) Expert Opin. Ther. Patents 12 (7); Southan & Szabo (2003) Curr Med Chem 10 321-340; Annals of Oncology 22 (Supplement 1): i53-i59, 2011; Curr Opin Drug Discov Devel. 2010 September; 13(5):577-86; Mol Cancer Ther (August 2007) 6:2290; and references therein.

Hox (e.g. Hoxa9) Inhibitors

In embodiments of the present invention, the PARPi is combined with a second agent which may be a Hox inhibitor, e.g. a Hoxa9 inhibitor. By "Hoxa9 inhibitor" it is meant an agent that inhibits signalling via the Hoxa9 pathway, e.g. an agent that targets, decreases or inhibits Hoxa9 activity and/or that targets, decreases, inhibits or degrades a protein that promotes Hoxa9 activity and/or expression. Thus the agent may bind directly to Hoxa9 or may inhibit Hoxa9 indirectly by binding to another protein that promotes Hoxa9 activity and/or expression. The agent may also inhibit an interaction between components of the Hoxa9 pathway, thereby reducing or preventing Hoxa9 signalling. Inhibitors of other Hox family proteins are also within the meaning of the term "Hox inhibitor".

Hoxa9 is part of the Hox family of transcription factors, which are characterized by a conserved 60 amino acid homeobox DNA-binding domain. Mutations of the HOX genes have been linked to defects of limb and genital development (Utsch et al. Hum. Genet. 2002; 110(5):488-494). In addition, HoxA9 is critical to murine granulopoiesis, and dysregulated HOXA9 expression is implicated in more than 70% of human AML. Its expression is enriched in human $CD34^+CD38^-$ stem cells compared with normal $CD34^-$ cells (Kawagoe et al., Leukemia 1999; 13(5):687-698). Consistent with its role in leukemogenesis, HoxA9-knockout mice demonstrate the most severe phenotype of all the Hox knockout models, with multilineage hematopoietic differentiation defects (Izon et al. Blood 1998; 92(2):383-393), as well as defects in HSC repopulation and proliferation (Lawrence et al. Blood 2005; 106(12):3988-3994). Additionally, the ABD HOXA genes, HoxA7-HoxA10, are overexpressed in mice with expression of a partial tandem duplication of the mixed-lineage leukemia (MLL) allele (MLL PTD), which has been described in AML (Dorrance et al, J Clin Invest 2006; 116(10):2707-2716). This overexpression is also correlated with increased histone acetylation in HOX gene promoters, suggesting a unique role of epigenetic modification in the regulation of HOX genes. Consistently, downregulation of HOXA9 has been shown to be critical for survival in leukemia with MLL rearrangement (Ayton and Cleary, Genes and Development 2003; 17: 2298-307; Faber et al. Blood 2009; 113(11):2375-2385) although other studies have fielded conflicting results (Kumar et al., Blood 2004; 103: 1823-28; So et al., Blood 2004; 103:3092-99).

Components of the Hoxa9 pathway are described, for example, in Li et al., J Clin Invest 2013; 123(10):4195-4207 and Wang et al., Cancer Cell 2010; 17(6):597-608 and shown in FIGS. 14 and 17. FIG. 14 shows (downstream) proteins that, in complex with Hoxa9 protein, are involved in the activation of transcription of genes that promote leukemic cell survival, whereas FIG. 17 shows (upstream) proteins involved in the activation of transcription of mRNA encoding Hoxa9. The Hoxa9 inhibitor may target one or more of the pathway components described therein, e.g. downstream proteins such as PBX (pre-B-cell leukemia homeobox transcription factor), MEIS1, TORC (transducer of regulated CREB activity), CREB (cAMP response element-binding protein), CBP (CREB-binding protein) or GSK-3 (glycogen synthase kinase-3), or upstream proteins such as disrupter of telomeric silencing 1-like (DOT1L), menin, MLL (mixed lineage leukemia), protein arginine N-methyltransferase 1 (PRMT1), positive transcription elongation factor b (P-TEFb), bromodomain-containing protein 4 (BRD4), polymerase-associated factor complex (PAFc) or SALL-4 (spalt-like transcription factor 4), and/or one or more interactions of these components. Thus in various embodiments, the Hoxa9 inhibitor may be an inhibitor of PBX, MEIS1, TORC, CREB, CBP, GSK-3, DOT1L, menin, MLL, PRMT1, P-TEFb, BRD4, PAFc or SALL-4 (spalt-like transcription factor 4).

Inhibitors of Hoxa9 (including inhibitors of the above Hoxa9 signalling pathway components) are known or may be identified using known assays and/or as described in the examples below. For example, high throughput inhibitor library screening can be carried out using luciferase/GFP reporter driven by promoter/enhancer of Hoxa (So et al., Cancer Cell 2003, 4: 99-110) or its downstream targets such as c-myb (Hess et al., Blood 2006, 108: 297-304). Preferably the Hoxa9 inhibitor inhibits Hoxa9 and/or a Hoxa9 signalling pathway component with an IC50 of 100 µM or below, 10 µM or below, 1 µM or below, 100 nM or below, 10 nM or below, or 1 nM or below.

In one embodiment, the second agent (e.g. Hoxa9 inhibitor) is an inhibitor of GSK-3. Glycogen synthase kinase 3 (GSK-3) is a serine/threonine kinase for which two isoforms, β and β, have been identified (Woodgett, Trends Biochem. Sci., 16: 177-81 (1991). Both GSK3 isoforms are constitutively active in resting cells. GSK-3 promotes the association of CREB with TORC, CBP and MEIS1, which facilitates transcriptional activation by Hoxa9 (Wang et al., Cancer Cell 2010; 17(6):597-608). Thus inhibition of GSK-3 reduces or prevents signalling via the Hoxa9 pathway.

Suitable GSK-3 inhibitors, methods for their synthesis and assays for GSK inhibition are described in, for example, WO 03/004472, WO 03/055492, WO 03/082853, WO 2004/018455, WO 2004/037791, 06/001754, WO 07/040436, WO 07/040438, WO 07/040439, WO 07/040440, WO08/002244, WO08/002245 and Coghlan et al. Chemistry & Biology 2000, 7(10):793-803. GSK-3 inhibitors are also reviewed in, for example, Cohen et al. Nature Reviews Drug Discovery 2004, 3:479-487; Kramer et al. International Journal of Alzheimer's Disease Volume 2012, Article ID 381029, 32 pages; and Eldar-Finkelman et al., Front Mol Neurosci. 2011; 4:32. In one embodiment, the GSK-3 inhibitor is lithium, e.g. a lithium salt such as lithium carbonate, citrate, chloride, orotate, bromide or chloride. In another embodiment, the GSK-3 inhibitor is 3-(2,4-dichlorophenyl)-4-(1-methyl-1H-indol-3-yl)-1H-pyrrole-2,5-dione (SB216763) or 3-(3-chloro-4-hydroxyphenylamino)-4-(2-nitrophenyl)-1H-pyrrole-2,5-dione (SB-415286), the structures of which are shown as formulae (I) and (II) below:

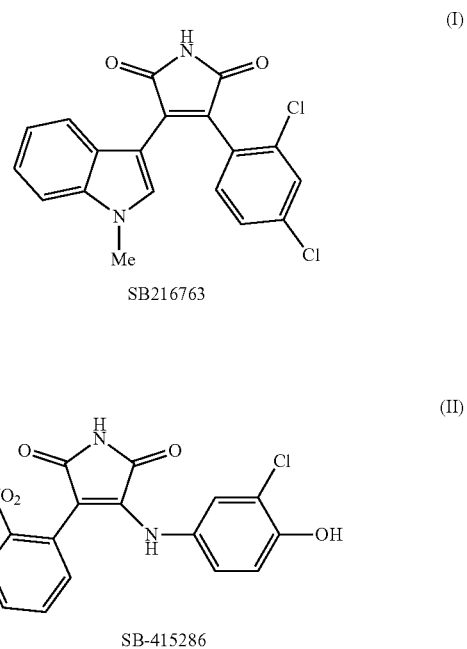

Further GSK3 inhibitors include 6-BIO, hymenialdisine, dibromocantharelline, CT98014, CT98023, CT99021, TWS119, AR-A014418, AZD-1080, kenpaullone, alsterpaullone, cazpaullone, aloisine A, manzamine A, palinurine, tricantine, TDZD-8, NP00111, NP031115, NP031112 (tideglusib), HMK-32 and L803-mts, the chemical structures and synthesis of which are described or referenced in Eldar-Finkelman et al., Front Mol Neurosci. 2011; 4:32.

In another embodiment, the second agent (e.g. Hoxa9 inhibitor) is an inhibitor of DOT1L. Suitable DOT1L inhibitors, methods for their synthesis and DOT1L inhibition assays are described in, for example, WO 2015/134603, WO 2015/073706, WO 2015/017863, WO 2015/013256, WO 2014/152562, WO 2014/127191, WO 2014/039839, WO 2014/035140, WO 2014/026198, WO 2014/100662 and. In some embodiments, the DOT1L inhibitor is (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol (EPZ-5676), which has the following formula (III):

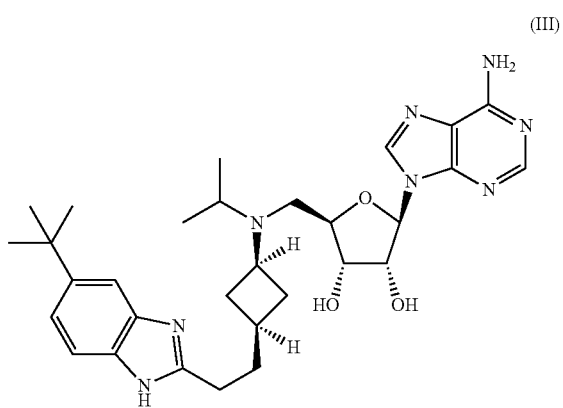 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

In a further embodiment, the DOT1L inhibitor is 1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea (EPZ 4777) having formula (IV):

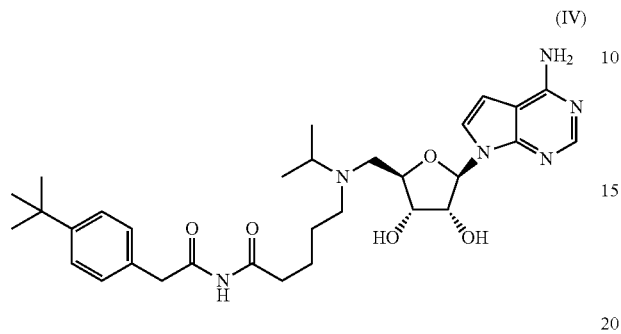

(IV)

Further DOT1L inhibitors and assays for DOT1L inhibition are disclosed in Basavapathruni et al., Chem Biol Drug Des. 2012; 80(6):971-980; Anglin et al., J Med Chem. 2012; 55(18):8066-74; Deng et al., Med. Chem. Commun., 2013, 4:822-826; Daigle S R et al. Cancer Cell. 2011; 20(1):53-65; and Scott et al., Blood 2013, 122:1017-1025.

In another embodiment, the Hoxa9 inhibitor is an inhibitor of menin. Suitable menin inhibitors, methods for their synthesis and menin inhibition assays are described in, for example, WO 2014/200479, WO 2014/164543 and WO 2011/029054. Further menin inhibitors are disclosed in Grembecka et al. Nat Chem Biol. 2012, 8(3):277-284, and Borkin et al. Cancer Cell. 2015, 27(4):589-60. In some embodiments, the menin inhibitor is MI 463, MI 503 or MI 136, the structures of which are shown below in formulae (V), (VI) and (VII) below:

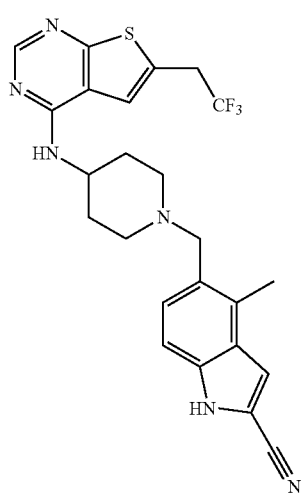

(V)

MI 463

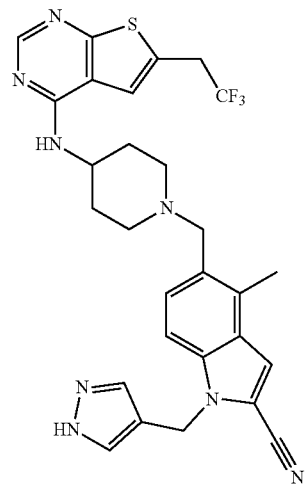

(VI)

MI 503

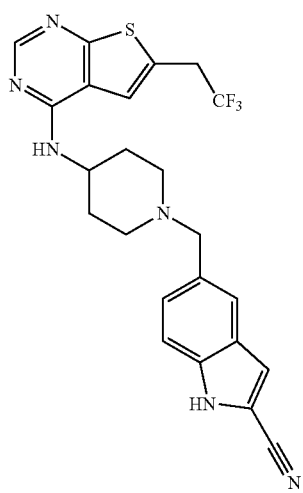

(VII)

MI 136

In further embodiments, expression or activity of a Hox signalling pathway component (e.g. Hoxa9, GSK3 or DOT1L) may be inhibited or reduced using a biological or biotechnological method. For instance, the Hox inhibitor (e.g. Hoxa9 inhibitor, GSK3 inhibitor or DOT1L inhibitor) may comprise a sequence-specific polynucleotide that can interfere with the transcription of one or more endogenous gene(s) encoding a Hox signalling pathway component (e.g. Hoxa9, GSK3 or DOT1L); a sequence-specific polynucleotide that can interfere with the translation of RNA transcripts (for example, a double-stranded RNA, siRNA, or ribozyme); a sequence-specific polypeptide that can interfere with the stability of one or more proteins; a zinc finger protein that bind one or more polynucleotides; or a meganuclease that has activity towards one or more polynucleotides. Gene editing technologies, genetic editing technologies and genome editing technologies are well known in the art. The nucleic acid and amino acid sequences of Hoxa9, other Hox family members and Hox pathway signalling components (e.g. GSK3 and DOT1L) in humans and other mammals are known and are available from publicly accessible databases.

One method of gene editing involves the use of transcription activator-like effector nucleases (TALENs) which induce double-strand breaks which cells can respond to with repair mechanisms. Non-homologous end joining reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. In some embodiments, TALENs may be used to inhibit expression or activity of Hoxa9 or another protein in the Hoxa9 signalling pathway.

Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) proteins to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies such as TALENs. Using the CRISPR/Cas strategy, retargeting the nuclease complex only requires introduction of a new RNA sequence and there is no need to reengineer the specificity of protein transcription factors. Thus in particular embodiments, the Hoxa9 inhibitor may comprise a CRISPR/Cas 9 system targeted to Hoxa9 or a Hoxa9 signalling component, e.g. comprising or encoding a guide RNA targeted to a nucleic acid sequence encoding Hoxa9 or a Hoxa9 signalling component.

Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into a cell and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-24 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

Interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers. In embodiments of the present invention, the Hoxa9 inhibitor may comprise a small interfering RNA (or e.g. an expression vector encoding such an interfering RNA) targeted to Hoxa9 or a Hoxa9 signalling component, e.g. complementary to a nucleic acid sequence (e.g. an RNA transcript) encoding Hoxa9 or a Hoxa9 signalling component.

Pharmaceutical Combination

It has now been surprisingly found that the combination of a PARPi and a second agent (e.g. a GSK3i, DOT1Li or other Hoxa9 inhibitor) possesses beneficial therapeutic properties, which render it particularly useful for the treatment of AML, particularly in the MLL subtype thereof.

Thus in one aspect the present invention provides a pharmaceutical composition comprising a quantity, which is jointly therapeutically effective at treating AML, of a PARPi and a second agent (e.g. a GSK3i, DOT1Li or other Hoxa9 inhibitor). In various embodiments, the PARPi and second agent (e.g. a GSK3i, DOT1Li or other Hoxa9 inhibitor) may be administered together in a single pharmaceutical composition, separately in one combined unit dosage form or in two separate unit dosage forms, or sequentially. The unit dosage form may also be a fixed combination.

The pharmaceutical compositions for separate administration of the PARPi and second agent (e.g. a GSK3i, DOT1Li or other Hoxa9 inhibitor) or for the administration in a fixed combination (i.e., a single galenical composition comprising the PARPi and second agent (e.g. a GSK3i, DOT1Li or other Hoxa9 inhibitor) may be prepared in a manner known in the art. The compositions may be suitable for enteral, such as oral or rectal, topical, and parenteral administration to subjects, including mammals (warm-blooded animals) such as humans, comprising a therapeutically effective amount of at the pharmacologically active agents, e.g., as indicated above, in combination with one or more pharmaceutically acceptable carriers or diluents, especially suitable for enteral or parenteral application. Suitable pharmaceutical compositions contain, e.g., from about 0.1% to about 99.9%, preferably from about 1% to about 60%, of the active ingredient(s).

Pharmaceutical compositions for the combination therapy for enteral or parenteral administration are, e.g., those in unit dosage forms, such as sugar-coated tablets, tablets, capsules or suppositories, ampoules, injectable solutions or injectable suspensions. Topical administration is e.g. to the skin or the eye, e.g. in the form of lotions, gels, ointments or creams, or in a nasal or a suppository form. If not indicated otherwise, these are prepared in a manner known per se, e.g., by means of conventional mixing, granulating, sugar-coating, dissolving or lyophilizing processes. It will be appreciated that the unit content of each active agent contained in an individual dose of each dosage form need not in itself constitute an effective amount since the necessary effective amount can be reached by administration of a plurality of dosage units.

Pharmaceutical compositions may comprise one or more pharmaceutical acceptable carriers or diluents and may be manufactured in conventional manner by mixing one or both active agents with a pharmaceutically acceptable carrier or diluent. Examples of pharmaceutically acceptable diluents include, but are not limited to, lactose, dextrose, mannitol, and/or glycerol, and/or lubricants and/or polyethylene glycol. Examples of pharmaceutically acceptable binders include, but are not limited to, magnesium aluminum silicate, starches, such as corn, wheat or rice starch, gelatin, methylcellulose, sodium carboxymethylcellulose and/or polyvinylpyrrolidone, and, if desired, pharmaceutically acceptable disintegrators include, but are not limited to, starches, agar, alginic acid or a salt thereof, such as sodium alginate, and/or effervescent mixtures, or adsorbents, dyes, flavorings and sweeteners. It is also possible to use the active agents in the form of parenterally administrable compositions or in the form of infusion solutions. The pharmaceutical compositions may be sterilized and/or may comprise excipients, for example preservatives, stabilizers, wetting compounds and/or emulsifiers, solubilisers, salts for regulating the osmotic pressure and/or buffers.

In particular, a therapeutically effective amount of each of the active agents of the combination may be administered simultaneously or sequentially and in any order, and the components may be administered separately or as a fixed combination. For example, in one aspect, disclosed herein is a method comprising: (i) administration of a first agent (e.g. PARPi) in free or pharmaceutically acceptable salt form; and (ii) administration of a second agent (e.g. Hoxa9 inhibitor) in free or pharmaceutically acceptable salt form, simultaneously or sequentially in any order, in jointly therapeutically effective amounts, preferably in synergistically effective amounts, e.g., in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each active agent employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

For purposes of the present invention, a therapeutically effective dose will generally be a total daily dose administered to a host in single or divided doses. The PARPi may, for example, be administered to a host in a daily dosage range of, for example, from about 0.01 to about 1000 mg/kg body weight of the recipient, preferably about 0.1-100 mg/kg body weight of the recipient, more preferably from about 0.1 to 10 mg/kg body weight of the recipient. The Hoxa9 inhibitor may, for example, be administered to a host in a daily dosage range of, for example, from about 0.01 to about 1000 mg/kg body weight of the recipient, preferably about 0.1-100 mg/kg body weight of the recipient, more preferably from about 0.1 to 10 mg/kg body weight of the recipient. Dosage unit compositions may contain such amounts of submultiples thereof to make up the daily dose.

A further benefit is that lower doses of the active ingredients of the combination of the invention can be used, e.g., that the dosages need not only often be smaller but are also applied less frequently, or can be used in order to diminish the incidence of side effects. This is in accordance with the desires and requirements of the patients to be treated.

The combination of the PARPi and second agent (e.g. a GSK3i, DOT1Li or other Hoxa9 inhibitor) can be used alone or combined with at least one other pharmaceutically active compound for use in these pathologies. These active compounds can be combined in the same pharmaceutical preparation or in the form of combined preparations "kit of parts" in the sense that the active agents can be dosed independently or by use of different fixed combinations with distinguished amounts of the active agents, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with the combination of a PARPi and a second agent (e.g. a GSK3i, DOT1Li or other Hoxa9 inhibitor) are cytotoxic chemotherapy drugs, such as anastrozole, doxorubicin hydrochloride, flutamide, dexamethaxone, docetaxel, cisplatin, paclitaxel, etc.

Chemotherapy typically refers to treatment with drugs or chemical compounds that target cancer cells. Chemotherapy may involve administration of a chemotherapeutic compound, which may have a cytotoxic or cytostatic effect, or which may induce a cyto-protective autophagy response in the cell. The chemotherapeutic agent may be an agent that induces apoptosis, such as p53-dependent apoptosis, or that induces cell cycle arrest, including p53-dependent cell cycle arrest, in a cell that is abnormally proliferating or cancerous. Commonly used chemotherapeutic agents include DNA damaging agents and genotoxic agents that can activate p53-dependent apoptosis or p53-dependent cell cycle arrest in a proliferating cell. In particular embodiments, the PARP inhibitor and second agent (e.g. a GSK3i, DOT1Li or other Hoxa9 inhibitor) may be administered to the subject in combination with one or more such chemotherapeutic agents.

Thus in some embodiments the PARPi and second agent (e.g. GSK3i, DOT1Li or other Hoxa9 inhibitor) may be administered together with a chemotherapeutic agent such as cytarabine (ara-C), either alone or in combination with an anthracycline such as daunorubicin or doxorubicin. In another embodiment, the PARPi and second agent (e.g. GSK3i, DOT1Li or other Hoxa9 inhibitor) may be administered together with all-trans-retinoic acid (ATRA or tretinoin), optionally further in combination with chemotherapy (e.g. an anthracycline such as daunorubicin or doxorubicin).

In some embodiments the active agents described herein may be present in the pharmaceutical combination in the form of pharmaceutically acceptable salts. Salts can be present alone or in mixture with free compound. Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

"Pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

In general, the term "combination" as used herein refers to either a fixed combination in one dosage unit form, or a non-fixed combination (or kit of parts) for the combined administration where a PARPi and a Hoxa9 inhibitor may be administered independently at the same time or separately within time intervals, especially where these time intervals allow that the active agents show a cooperative, e.g. synergistic effect. The term "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "fixed combination" means that the active ingredients, e.g. a PARPi and Hoxa9 inhibitor, are both administered to a patient simultaneously in the form of a single entity or dosage. The terms "non-fixed combination" or "kit of parts" mean that the active ingredients are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Acute Myeloid Leukemia

The pharmaceutical combination described herein may be used to treat acute myeloid leukemia (AML), especially mixed lineage leukemia (MLL), in a subject suffering therefrom. Acute myeloid leukemia may also be referred to as acute myelogenous leukemia or acute nonlymphocytic leukemia (ANLL). AML is a cancer of the myeloid line of leukocytes, and is characterized by the rapid growth and accumulation of abnormal leukocytes in the bone marrow. AML is the most common acute leukemia affecting adults, and its incidence increases with age.

About half of the subjects suffering from AML have at least one chromosomal abnormality. In particular, the chromosomal translocations t(8;21) and t(15;17) and abnormal 11q23 are associated with production of the oncogenic fusion proteins AML1-ETO, PML-RARα and MLL-AF9 respectively, and each account for around 5 to 10% of adult and childhood cases of AML. In addition, the chromosomal inversion inv16 and the translocation t(16;16), both resulting in the expression of the oncofusion protein CBFβ-SMMHC, are associated with around 5% of AML cases in both adults and children. The remaining AML patients typically show a normal karyotype in cytogenetic studies, or a complex cytogenetic profile, which usually associates with a poor prognosis.

In embodiments of the present invention, the pharmaceutical combination described herein is preferably used to treat mixed lineage leukemia (MLL). MLL is a sub-type of AML or acute lymphoblastic leukemia (ALL) associated with a rearrangement in the MLL gene and/or abnormal expression or activity of the MLL protein, e.g. the production of the oncogenic fusion proteins MLL-AF9, MLL-AF4, MLL-ENL, MLL-ELL or MLL-AF6, partial tandem duplication of the MLL gene (MLL-PTD) or non-rearranged MLL.

Mixed lineage leukemia (MLL) typically constitutes over 70% of infant leukemias and approximately 10% of adult acute myeloid leukemias (AML) (Hess, J. L. (2004), Trends Mol Med 10, 500-507; Krivtsov, A. V., and Armstrong, S. A. (2007), Nat Rev Cancer 7, 823-833). MLL represents a particularly aggressive form of acute leukemia (which may be of the myeloid, lymphoid or mixed lineages) and patients with this disease generally have poor prognoses; these patients often suffer from early relapse after treatment with current chemotherapies. There is thus a great and present need for new treatment modalities for patients suffering with MLL.

A common hallmark of MLL disease is a chromosomal translocation affecting the MLL gene on chromosome 11q23. Normally, the MLL gene encodes for a SET-domain histone methyltransferase that catalyzes the methylation of lysine 4 of histone H3 (H3K4) at specific gene loci (Milne et al. (2002) Mol Cell 10, 1107-1117; Nakamura et al. (2002), Mol Cell 10, 1119-1128). Gene localization is conferred by specific interactions with recognition elements within MLL, external to the SET-domain (Ayton et al. (2004) Mol Cell Biol 24, 10470-10478; Slany et al., (1998) Mol Cell Biol 18, 122-129; Zeleznik-Le et al. (1994) Proc Natl Acad Sci USA 91, 10610-10614). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany (2009) Haematologica 94, 984-993). These fusion partners are capable of interacting directly, or indirectly, with another histone methyltransferase, DOT1L (Bitoun et al. (2007) Hum Mol Genet 16, 92-106; Mohan et al. (2010) Genes Dev. 24, 574-589; Mueller et al. (2007) Blood 110, 4445-4454; Mueller et al. (2009) PLoS Biol 7, e1000249; Okada et al. (2005) Cell 121, 167-178; Park et al. (2010) Protein J 29, 213-223; Yokoyama et al. (2010) Cancer Cell 17, 198-212; Zhang et al. (2006) J Biol Chem 281, 18059-18068). As a result, translocation products retain gene-specific recognition elements within the remainder of the MLL protein, but also gain the ability to recruit DOT1L, to these locations (Monroe et al. (2010) Exp Hematol. 2010 Sep. 18. [Epub ahead of print] Pubmed PMID: 20854876; Mueller et al., 2007; Mueller et al., 2009; Okada et al., 2005). DOT1L catalyzes the methylation of H3K79, a chromatin modification associated with actively transcribed genes (Feng et al. (2002) Curr Biol 12, 1052-1058; Steger et al. (2008) Mol Cell Biol 28, 2825-2839). The ectopic H3K79 methylation that results from MLL fusion protein recruitment of DOT1L leads to enhanced expression of leukemogenic genes, including HOXA9 and MEIS1 (Guenther et al. (2008) Genes & Development 22, 3403-3408; Krivtsov et al. (2008) Nat Rev Cancer 7, 823-833; Milne et al. (2005) Cancer Res 65, 11367-11374; Monroe et al, 2010; Mueller et al, 2009; Okada et al, 2005; Thiel et al. (2010) Cancer Cell 17, 148-159).

MLL can be characterized by the genetic lesions of the MLL gene. Such genetic lesions include chromosomal rearrangements, such as translocations, deletions, and/or duplications of the MLL gene. MLL has been categorized or characterized as having a chimeric fusion of MLL, partial tandem duplication of the MLL gene (MLL-PTD), or non-rearranged MLL. Chromosomal rearrangements or translocations can be identified by cytogenetic methods known in the art. For example, chromosomal rearrangements resulting in chimeric fusions can be detected by probe-based assays, such as FISH (fluorescence in situ hybridization) or sequence amplification by PCR. Those chromosomal rearrangements that result in partial tandem duplications are often difficult to detect by probe-based assays, and therefore, other DNA sequencing methods known in the art may be used, such as Sanger sequencing, de novo sequencing, shotgun sequencing, or next generation sequencing methods. MLL-PTD can be identified by DNA sequencing. MLL chimeric fusions can be identified by FISH. Diagnosis of MLL can be performed e.g. by detection of rearrangements of the MLL gene. Preferably, MLL that can be treated by the pharmaceutical combination described herein is chimeric fusion of MLL, partial tandem duplication of MLL (MLL-PTD) or nonrearranged MLL.

In further embodiments, the subject may be suffering from a preleukemic blood disorder, e.g. a condition which may develop into AML. Examples of such conditions include myelodysplastic syndrome and myeloproliferative disease.

In some embodiments, the subject is suffering from relapsed AML. A large proportion of AML patients relapse, i.e. one or more clinical signs or symptoms of AML re-appear in the subject after a remission. A remission may be indicated by an alleviation of one or more signs or symptoms of the disease, e.g. a decrease in the number of leukemic myeloblasts or a normalization of other parameters of leukocyte function. Typically a period of remission is induced by an initial phase of therapy, e.g. using one or more standard therapies for AML as described herein.

Detecting Chromosomal Abnormalities

Embodiments of the present invention may involve a step of detecting a chromosomal abnormality at 11q23 in a sample from the subject, especially detecting a rearranged MLL gene. These abnormalities may be detected using, for example, cytogenetic methods such as karyotyping or fluorescent in situ hybridisation or by Reverse Transcription-Polymerase Chain Reaction (RT-PCR).

Karyotyping refers to chromosome analysis, e.g. of metaphase chromosomes which have been banded using trypsin and histological stains, resulting in unique banding patterns on the chromosomes. Various chromosome-banding techniques may be used, including quinacrine banding (Q-banding), Giemsa banding (G-banding), reverse banding (R-banding), constitutive or centromere banding (C-banding) and nucleolar organizing region stains (NOR stains). High-resolution banding may also be used, e.g. to increase the number of observable bands. A sample comprising cells from e.g. bone marrow or blood may be cultured using standard cell culture techniques in order to increase the number of observable leukemic myeloblasts. A mitotic inhibitor such as colchicine may then be added to the culture to halt cell division at mitosis. A hypotonic solution may be used to swell the cells and induce spreading of the chromosomes, as well as lysing red blood cells. The cells are then fixed and the banding pattern analysed under a microscope. Typically the presence of particular chromosomal abnormalities can be determined by the presence of corresponding banding patterns in the nuclei of leukemic myeloblasts from the subject. Alternatively, the chromosomal abnormalities may be detected using fluorescent in situ hybridization (FISH). Fluorescent in situ hybridization utilises a fluorescently labelled polynucleotide probe to hybridize to specific DNA sequences in the chromosomes. FISH may be performed, for example, on bone marrow smears or blood smears as well as uncultured bone marrow aspirates or biopsy samples.

Typically FISH is performed on a microscope slide comprising a blood or bone marrow sample. The DNA probe is allowed to hybridise to complementary sequences present in the sample, after which bound probe is visualised using fluorescence microscopy. In some embodiments a number of leukemic myeloblasts may be analysed to look for the presence of a particular mutation which is specifically bound by the probe. Accordingly, specific chromosomal abnormalities can be detected in the sample from the subject.

More recently a molecular test, the Reverse Transcription-Polymerase Chain Reaction test (RT-PCR) has entered the routine diagnostics of AML and in particular of APL. This test allows to specifically detect the fusion genes associated with leukaemia, e.g. MLL-AF9. After extracting RNA from the blood or bone marrow of the patients, the RNA is retro-transcribed in cDNA which will be then used as template for the PCR reaction. By using oligonucleotide primers specific for certain sequences, typically spanning the breakpoints, regions of interest can be amplified and further analyzed.

The chromosomal abnormality may be detected in any suitable sample obtained from the subject. Typically the sample comprises leukocytes, especially those of the myeloid lineage. In preferred embodiments, the sample is derived from peripheral blood or bone marrow. For instance, the sample may comprise blood cells or bone marrow cells obtained from blood or bone marrow smears. In particular, bone marrow cells may be obtained by bone marrow aspiration or biopsy using known techniques.

Therapeutic Methods and Uses

Once a subject suffering from AML has been identified as suffering from MLL leukemia, the pharmaceutical combination described herein may be administered to the subject in a therapeutically effective amount in order to treat the disease and/or to alleviate the symptoms thereof.

The treatment using the pharmaceutical combination described herein includes prophylactic (preventive) and therapeutic treatment as well as the delay of progression of AML, especially MLL. The term "prophylactic" means the prevention of the onset or recurrence of diseases. The term "delay of progression" as used herein means administration of the combination to patients being in a pre-stage or in an early phase of AML to be treated, in which patients for example a pre-form of AML (e.g. a preleukemic disorder) is diagnosed or which patients are in a condition, e.g. during a medical treatment or a condition resulting from an accident, under which it is likely that a corresponding disease will develop. "Therapeutically effective" as used herein preferably relates to an amount that is therapeutically or in a broader sense also prophylactically effective against the progression of AML.

The subject to be treated may be a human or a non-human animal. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from AML, especially MLL.

To demonstrate that the pharmaceutical combination described herein is particularly suitable for the effective treatment of AML with good therapeutic margin and other advantages, clinical trials can be carried out in a manner known to the skilled person. Suitable clinical studies are, e.g., open label, dose escalation studies in patients with AML, particularly subjects diagnosed with MLL. Such studies prove in particular the synergism of the active ingredients of the combination of the invention. The beneficial effects can be determined directly through the results of these studies which are known as such to a person skilled in the art. Such studies are, in particular, suitable to compare the effects of a monotherapy using the active ingredients and a combination of the invention. Preferably, the dose of e.g. a PARPi is escalated until the Maximum Tolerated Dosage is reached, and e.g. a GSK3i, DOT1Li or other Hoxa9 inhibitor is administered with a fixed dose. Alternatively, the PARPi is administered in a fixed dose and the dose of the second agent (e.g. GSK3i, DOT1Li or other Hoxa9 inhibitor) is escalated. Each patient receives doses of the PARPi either daily or intermittent. The efficacy of the treatment can be determined in such studies, e.g., after 12, 18 or 24 weeks by evaluation of symptom scores every 6 weeks.

The administration of a pharmaceutical combination of the invention results not only in a beneficial effect, e.g., a synergistic therapeutic effect, e.g., with regard to alleviating, delaying progression of or inhibiting the symptoms, but also in further surprising beneficial effects, e.g., fewer side effects, an improved quality of life or a decreased morbidity, compared with a monotherapy applying only one of the individual active agents used in the combination of the invention.

A further benefit is that lower doses of the active ingredients of the combination of the invention can be used, e.g., that the dosages need not only often be smaller but are also applied less frequently, which may diminish the incidence or severity of side effects. This is in accordance with the desires and requirements of the patients to be treated.

Methods for Selecting a Therapy

In a further aspect, the present invention provides a method for selecting a therapy for a patient suffering from AML. The method may comprise a step of performing cytogenetic testing for chromosomal abnormalities as described above. For instance, the method may involve determining whether a chromosomal abnormality is present in a sample obtained from the subject at chromosome 11q23, and optionally at one or more further chromosomal loci known to be associated with further AML subtypes. For instance, in particular embodiments, the cytogenetic testing may comprise determining whether one or more of the following chromosomal abnormalities is present in the subject: t(8;21), t(15;17), t(16;16) and inv(16). Preferably the cytogenetic testing comprises determining whether a chromosomal abnormality resulting in a rearranged MLL gene and/or expression of a MLL fusion protein is present in the subject.

If a chromosomal abnormality at 11q23 is detected in the subject, the method typically involves selecting a therapy comprising administration of the pharmaceutical combination described herein to the subject, i.e. combined administration of (a) a poly-(ADP-ribose)-polymerase (PARP) inhibitor and (b) a second agent (e.g. a GSK3i, DOT1Li or other agent that inhibits Hoxa9 signalling).

On the other hand, if no chromosomal abnormality at 11q23 is present in the subject, an alternative therapy may be selected. For instance, if a chromosomal abnormality at t(8;21) or t(15;17) is detected in the sample, a monotherapy comprising administration of a poly-(ADP-ribose)-polymerase (PARP) inhibitor may be selected for the subject. Thus PARPi monotherapy is typically indicated for subjects who express a mutant fusion protein selected from (a) acute myeloid leukemia-1 transcription factor and eight-twenty-one corepressor (AML1-ETO) and (b) promyelocytic leukaemia protein and retinoic acid receptor alpha (PML-RARα). In this context, by "monotherapy" it is meant that the PARPi is administered without administration of a second agent (e.g. GSK3i, DOT1Li or other Hoxa9 inhibitor), e.g. the PARPi may be administered alone or optionally in combination with standard chemotherapy.

The invention will now be described by way of example only with reference to the following non-limiting embodiments.

EXAMPLES

Since specific transcriptional programs including those involved in DDR are frequently deregulated by various oncogenic transcription factors, we reasoned that transcriptional deregulation might represent an alternative mechanism allowing the targets of differential DDR for effective leukemia treatments[18]. To this end, we performed extensive molecular and functional analyses of the effect of PARP inhibition on some of the most common forms of AML. Here we show that AML driven by AML1-ETO and PML-RARα, which suppress the expression of DDR genes, exhibit a BRCAness phenotype and can be efficiently targeted by PARPi treatment. On the other hand, MLL-driven leukemia is resistant to PARPi but can be sensitized to the treatment by genetic or pharmacological inhibition of its downstream target, Hoxa9, which mediates effective DDR.

Materials and Methods
Retroviral Transduction/Transformation Assay (RTTA)

RTTA was performed on primary murine hematopoietic cells as described[21]. c-Kit positive progenitor cells were isolated from wild type Ly5.1 mouse bone marrow, and cultured overnight in R10 medium [RPMI 1640 containing 10% FCS, 100 U/mL penicillin and 100 μg/mL streptomycin] supplemented with 20 ngml-1 stem cell factor (SCF), 10 ngml-1 interleukin (IL)-3, and 10 ngml-1 IL-6. Transduction using concentrated viral supernatant expressing the oncogene of interest was carried out by centrifugation (spinoculation) at 800 g at 32° C. for 2 hours in the presence of 5 μg ml$^{-1}$ polybrene (Sigma-Aldrich). Cells were subsequently plated in 1% methylcellulose medium (M3231; Stem Cell Technologies) containing 20 ngml$^{-1}$ SCF, 10 ngml$^{-1}$ IL-3, 10 ngml$^{-1}$ IL-6 and 10 ngml$^{-1}$ granulocyte macrophage colony-stimulating factor (GM-CSF) and appropriate selection antibiotic. Colonies were counted after 7 days of culture and replated every 6-7 days at 5×103-1.5×104 cell density. Re-plating was performed weekly to generate primary cell lines for further analysis. After the third or fourth round of plating, cells were cultured in R20/20 medium (RPMI 1640, 20% FCS, 20% WEHI-conditioned medium, 2 mM L-glutamine, 100 U/ml penicillin, and 100 μg/ml streptomycin) supplemented with 20 ngml$^{-1}$ stem cell factor (SCF), 10 ngml$^{-1}$ interleukin (IL)-3, and 10 ngml$^{-1}$ IL-6 to establish cell lines. All recombinant murine cytokines were from PeprotechEC.

Cell Culture

NB4-LR2 and THP1 cell lines (kindly provided by Dr Arthur Zelent and Professor Mel Greaves respectively) were cultured in RPMI (Invitrogen) supplemented with 10% selected FBS (R10), 2 mM L-Glutamine. Kasumi cell line (kindly provided by Dr Olaf Heidenreich) was cultured in RPMI-Hepes modified (Sigma) supplemented with 20% selected FBS and 2 mM L-Glutamine (R20). Cell lines were validated by qPCR for their respective oncogenes. NIH3T3 and GP2 cell line was cultured in DMEM (Invitrogen) supplemented with 10% selected FBS and 2 mM L-Glutamine. Human primary AML cells were cultured in IMEM (Invitrogen) supplemented with 10% PBS, 2 mM L-Glutamine, 10 ng/mL each of human cytokines, IL3, IL6, SCF, FLT3 ligand, and TPO. Cells were kept at 37° C. and 5% $CO_2$. Use of human primary cells was approved by King's College London committee and consents of the patients were obtained.

In Vitro Drug Treatment

Most of the inhibitor studies on mouse cells were carried out by plating 3-5×10$^3$ cells in 1% methylcellulose medium containing 20 ng ml$^{-1}$ SCF, 10 ng ml$^{-1}$ IL-3, 10 ngml$^{-1}$ IL-6 and 10 ng ml$^{-1}$ GM-CSF in the presence of 1 μM Olaparib (LC Laboratories), 1 μM Veliparib (Abbott) or 8 mM Lithium Chloride (LiCl, Sigma) at the concentrations as indicated in the Results section. Colonies were scored 6-7 days after plating. For other in vitro studies, mouse leukemic cells and primary AML cell lines were subjected to continuously Olaparib (1 μM) or LiCl (8 mM) treatment in liquid culture for whole duration as indicated in the figures or figure legends. For human leukemic cell lines, experiments were performed as described above with 5 μM Olaparib.

Flow Cytometric Analysis

Flow cytometry analyses of mouse leukemic cells for both in vitro and in vivo experiments were performed as previously described61 using mouse specific anti-CD11b (Mac-1) (clone M1/70), anti-Gr1 (clone RB6-8C5), anti-c-Kit (clone 2B8), anti-CD45.1 (clone A20) and anti-CD45.2 (clone 104) antibodies from BioLegend. For humanized mouse model, the engrafted human donor cells were analysed using anti-human CD45 (clone H130) and CD33 (clone WM53).

Cell Cycle Analysis

For each assay 1×10$^5$ cells were collected, washed in PBS and fixed in 70% cold ethanol. After re-hydration with PBS and centrifugation at 500 g for five minutes, the cells were incubated with a solution of PBS containing 1% FCS, 40 ug/ml RNAse and 500 ug/ml propidium iodide solution (Sigma-Aldrich) in the dark for 30 minutes at 37° C. Samples were then analyzed at the FACS LSRII (BD Biosciences Pharmingen). DNA peaks were analyzed with FACS Diva.

Annexin V Staining

For each assay 1×10$^5$ cells were collected, washed in PBS and re-suspended in Annexin V binding solution (25 mM Hepes, 140 mM KCl, 2.5 mM $CaCl_2$ pH 7.2). After centrifugation at 500 g for five minutes the cells were incubated with the Annexin V Binding solution containing 0.25 ug/ml mouse anti Annexin V-FITC antibody (Biolegend 640906) and 1 ug/ml propidium iodide in the dark for 30 minutes at 4° C. Samples were then washed in PBS analysed at the FACS LSRII (BD Biosciences Pharmingen) with FACS Diva.

Beta Galactosidase Staining

Cells were cytospun onto a glass slide at 400 g for 5 minutes and then fixed for 10 minutes with 2% formaldehyde/0.2% glutaraldehyde (Sigma Aldrich). Cells were then washed with PBS, and then incubated at 37° C. for at least 2 hours with a staining solution (30 mM Citric Acid/Phosphate buffer, 5 mM $K_4Fe(CN)_6$, 5 mM $K_3Fe(CN)_6$, 150 mM NaCl, 2 mM $MgCl_2$, 1 mg/ml X-Gal) (All reagents from Sigma-Aldrich)62. Cells were counted in at least 5 fields for each slide, for a total of over 100 cells. The percentage of senescent cells was calculated by the percentage of the number of blue cell in the field.

Immunofluorescence Staining of γH2AX and RAD51

Cells were cytospun onto a glass slide at 400 g for 5 minutes and then fixed for 30 minutes in 4% PFA and permeabilized and blocked in 0.8% Tx-100, 10% FBS/1% BSA (Sigma-Aldrich) in PBS for 15 min at room temperature. Mouse anti mouse γH2AX (ser139) (Upstate clone JBW301#05-636) and rabbit anti mouse RAD51 (Santa Cruz Biotecnology H92# sc-8349) were diluted in TBS containing 10% FBS/1% BSA and incubated overnight at 4C. Slides were then washed three times with PBS and subsequently incubated with 1:200 donkey anti mouse DL 488 (Jackson/Stratech 715-485-150) and 1:200 goat anti-rabbit Cy3 (Jackson/Stratech 111-165-144) in TBS containing DAPI 0.2 ug/ml, 10% FBS, 1% BSA for 1 hour at room temperature in the dark. Slides were then washed five times at 10 min each with PBS. Slides were briefly washed in water and air-dried prior to mounting with Mowiol-DABCO and a coverslip. Cells were counted in at least 5 fields for each slide, for a total of over 100 cells per condition.

May-Grunwald-Giemsa Staining

1×10$^5$ cells were cytospun for 5 min at 300 g onto glass slides. Slides were then stained with May-Grunwald solution (Sigma-Aldrich) for 3 min at room temperature. After washing in water, they were incubated for 20 min in Giemsa solution (Sigma-Aldrich) (1:20 in water). Slides were washed again in water before being mounted with Mowiol. Cells were counted in at least 5 fields for each slide, for a total of over 100 cells per condition.

Nitro Blue Tetrazolium (NBT) Reduction Assay

NBT reduction assay were performed to determine myeloid differentiation. 0.1% of NBT (final concentration) was added to the liquid culture or semi-solid methocult and incubated at 37° C. CO$_2$ incubator for 3 hrs and 12 hrs, respectively. Cells were then washed in PBS and the differentiated cells were indicated by the deposition of dark blue insoluble formazan (NBT positive cells) and the percentage of differentiated cells were counted under microscopy. At least 200 cells were counted in most of the cases.

Mouse Parp1 Knockdown

Scramble or mouse Parp1 targeting sequences were cloned into pSuper-Retro-Puro retroviral vector (OligoEngine). The target sequences for mouse Parp-1 gene (NM007415.2) are TAAAgAAGCTGACGGTGAA (targeting the position 2014-2032, sh # A)63, GCCGCCTACTCTATCCTCA (targeting the position 2014-2032, sh # D). The scramble sequence is GCGAAAGATGATAAGCTAA.

Expression of Mouse Parp1 shRNA in NIH3T3 Cell Line 1.6×10$^5$ cells were plated in each well of 6 well-plates mm and allowed to attach for 6 hrs when the cells were infected with 200 μl of concentrated virus expressing i) the empty vector, ii) the scramble or iii) shRNA against mouse Parp1 and 5 ug/ml of polybrene in a final volume of 2 ml. After 24 hours, the medium was replaced fresh one containing 1.5 μg/ml puromycin (Invitrogen) for a 3-days selection. Cells were then collected for RT-qPCR and Western Blot analysis.

Western Blot Analysis

Cells were collected by centrifugation and cell pellet was suspended in lysis buffer (0.02% SDS, 0.5% Triton, 300 mM NaCl, 20 mM Tris-HCl pH 7.5, 1 mM EDTA, 1 mM DTT, 10 mM NaF, 2 mM Na$_3$VO$_4$) containing 1× protease inhibitors (Roche) and incubated on ice for 30 min. Following centrifugation at 16000 g for 15 min at 4° C., the supernatant containing total cell extract was collected and kept at −80° C. Proteins from cell extracts were quantified using OD660 nm Assay (Pierce). 10 μg of cell extracts were loaded on a 12% polyacrylamide gel and then electrophoretically transferred onto a Hybond-PVDF membrane (GE Healthcare). The membrane was incubated for 1 h at room temperature in blocking buffer (TBS-T containing 8% skimmed milk) to block non-specific protein binding and then incubated at 4° C. overnight with the primary antibody, listed in Table S9. Mouse BRCA2 antibody was kindly provided by Dr. Lee. Following four washes with TBS-T, the membrane was incubated for 1 hour with the HPR-conjugated antibody, anti-mouse or anti rabbit (Jackson ImmunoResearch) diluted in blocking buffer. Antibody binding was visualized using the ECL Prime Western blotting detection system (GE Healthcare).

Immunoprecipitation Assay

Cells were lysed as above (with a reduced NaCl concentration to 200 mM). The 500 ug of total cell lysates were incubated with 1 ug anti-FLAG antibody at 4° C. for 12 hrs with rotation. Then protein-A cojugated beads were added to precipitate the protein complex and incubated at 4° C. for 1 hr with rotation. Beads were then washed 5 times with reduced NaCl cell lysis buffer and eluted by 50 ul 2% SDS-Tris buffer.

Real Time Quantitative PCR

RNA was extracted by using a kit from Fermentas and was reverse transcribed using Super-Script III from Invitrogen. qPCR was performed by using SYBR Green or Taqman probes on an ABI 7900HT Fast Real-Time PCR System (Applied Biosystems) using primers listed in Table S10. GAPDH is used a house keeping gene. Relative Expression levels were calculated using the 2-ΔΔCT method.

In Vivo Plasmid End-Joining Assay

In vivo plasmid end-joining assay was performed as described[65]. Briefly a Double Strand Break (DSB) is generated in the LacZ gene sequence of the plasmid PUC18 by EcoRI digestion. Nuclear extracts from pre-leukemic cells carrying the above mentioned oncofusion proteins were obtained by using the Nuclear Extraction Kit (Pierce). 2 μg of PUC18 plasmid was digested with EcoRI (Fermentas), dephosphorylated (Fermentas), separated on agarose gel 1% and extracted using a column based method (Qiagen). 5 μg nuclear extracts were then incubated in NHEJ buffer (50 mM Trietanolammine HCL pH7.5, 60 mM Potassium Acetate, 0.5 mM Magnesium Acetate, 250 uM dNTPs, 10 mM ATP, 5 mM dTT, 500 ug/ml BSA) for 5 min at 37° C. 250 ng of digested-dephosphorylated plasmid were then added to the reaction in 50-100 μl final volume and incubated for 24 hrs at 18° C. Next day, the DNA was purified using a column based method (Qiagen) and 30 ng were used to transform *E. Coli* and plate them on LB-agar plates+160 ug/ml X-Gal (Sigma-Aldrich) and 1 mM IPTG (Sigma-Aldrich). Colonies were counted and plotted as shown in FIG. 3*i/j*. The percentage of misrepair was calculated as the percentage of blue colonies versus total number of colonies.

Homologous Recombination Assay

U2OS cells containing a single copy of the DR-GFP reporter (U2OS-DR) was kindly provided by Dr Maria Jasin. 0.5×10$^6$ U2OS-DR cells were plated into 6-well plate. After 24 hours, cells were co-transfected with I-SceI expression (pCBASce, 1.25 μg), oncogenes of interests (1.25 μg) and RFP constructs (0.2 μg) using Lipofectamine 2000 (Invitrogen) according to the manufacture's protocol. Percentage of GFP-positive cells was measured by flow cytometry three days after transfection and normalized against percentage of RFP for transfection efficiency. Relative HR efficiency was then normalized to empty vector.

In Vivo Experiments

All the experimental procedures were approved by King's College London committee and conform to the UK Home office regulations.

We established humanized models of AML1-ETO and PML-RARα leukemia in sub-lethally irradiated NOD/SCID/IL2Rg−/−(NSG, 1 dose 200 RADs) by transplanting 2×10$^6$ Kasumi (intra-femoral, IF) and 1×10$^5$ NB4-LR2 or 1×10$^5$ THP1 (intravenous, IV) cells. The day after the transplantation, mice were split into two groups and given intra-peritoneal injections of vehicle (10% HBC) or Olaparib (25 mg/kg in 10% HBC) daily for 2-4 weeks. The maximum tolerable dose was calculated by in vivo dose-response experiments. Mice were monitored daily until they developed symptoms of leukemia, when they were culled and bone marrow, spleen and liver harvested and analyzed by FACS. The engraftment of human donor cells was defined as human CD45/CD33 double positive by FACS.

For Hoxa9 KO studies, we intravenously injected 106 MLL-AF9 leukemic cells (wild type or Hoxa9−/− background) together with 2×10$^5$ bone marrow rescue cells into lethally irradiated C57Bl/6 mice (2 doses of irradiation 550 RADS each) for disease development. For drug studies, the control cohort received vehicle (10% 2-Hydroxypropyl-beta-cyclodextrin, HBC, Sigma-Aldrich) and the PARPi treatment group received daily Olaparib 50 mg/kg in 10% HBC for two-four weeks.

For mouse MLL-AF9 LSC in vivo studies involving PARPi and GSK3i, MLL-AF9 LSC were pretreated in R20/20 with 4 mM LiCl or 1 uM Olaparib or combination for 3 days. Equal number 0.2×10$^6$ of live cells were transplanted into sublethally irradiated C57Bl6 mice. Continuous Olaparib and LiCO3 treatment was commenced on the day after irradiation and injection of cells. Mice were given 0.4% lithium carbonate containing diet (Harlan Laboratory) along with Olaparib by IP every other day for 4 weeks. The engraftment of mouse donor cells was defined as CD45.1+/CD45.2− by FACS.

For in vivo experiment with primary AML samples, $10^5$ AML1 cells transduced with firefly luciferase expressing plasmid were transplanted via by IF into the right femur of the NSG mice. Three days after transplantation, mice were supplemented with 0.4% $LiCO_3$ containing diet and treated with Olaparib as described above for alternative day until day 21. After day 21, mice were maintained on 5 days of lithium carbonate diet and alternated with 2 days regular diet and water for 2 additional weeks. From day 21, the tumor burdens of the animals were detected using IVIS Lumina II® (Caliper) with software Living Image® Verion 4.3.1. Briefly, 1000 µl of 30 mg/mL luciferin were injected into the animals by IP. 10 minutes after injection, the animals were maintained in general anaesthesia by isoflurane and put into the IVIS chamber for photography and detection of photon emission (large binning, F=1.2, exposure time: 3 mins). The tumor burden were measured and quantified by the same software as instructed. The animals were culled when the tumor burden was 10e8 photon per second or higher.

Microarray and Bioinformatic Analysis

Expression profiles of AML1-ETO (22 samples, cluster13), APL (18 samples, cluster 12), MLL (11 samples, cluster 16) patients were obtained from GEO accession: GSE115932. The data was supported by performing additional gene expression analysis on independent set of published microarray dataset from GSE6891 containing AML1-ETO (37 samples), APL (25 samples), and MLL (35 samples) leukemia samples. All intensity values was adjusted, normalized and summarized in log 2 scale using Bioconductor Affy66 (background correction: rma; normalization: quantiles; summarization: median polish). The differential expression analysis of AML1-ETO and APL against MLL were performed using Bioconductor Limma. The p-values were calculated by paired two-tailed t-Test. The selected genes' expression of AML-ETO, APL and MLL were plotted in box-whisker plot using Prism5 software. Gene set enrichment analysis (GSEA) was performed as described[67] using published datasets [44,45].

Statistical Analysis

All the experimental results were analyzed using unpaired two-tailed Student's t-Test, 1-way or 2-way ANOVA, as indicated in figure legends. Groups that are statistically compared shared a similar variance as shown in the figures. p-values lower than 0.05 were considered statistically significant. The log-rank test was used to compare survival curves.

Results

Pharmacological Inhibition of PARP Selectively Suppresses AML1-ETO and PML-RARα Mediated Leukemia To explore the therapeutic potentials of targeting PARP in acute leukemia, we investigated the effect of Olaparib, one of the most commonly used clinical PARPi, on clonogenic growth of primary murine hematopoietic cells transformed by the most common leukemia associated transcription factors (LATFs) including AML1-ETO, PML-RARα, MLL-AF9 and E2A-PBX using the retroviral transduction/transformation assay (RTTA), which has been successfully employed to model the corresponding human diseases[21-24]. While a dose-response titration assay identified the in vitro maximal tolerable dose at a concentration of up to 1 uM Olaparib that exhibited undetectable/minimal effects on normal primary bone marrow cells (FIG. 7a-b), the same treatment had striking impacts on primary cells transformed. PARPi significantly suppressed colony forming ability of cells transformed by AML1-ETO or PML-RARα (by about 90% p<0.001), although it had little impact on MLL-AF9 or E2A-PBX transformed cells (FIG. 1a-b and FIG. 7c-d). To confirm the specificity of the drug, we also reported very similar and selective leukemia suppressive effects using a different PARPi, Veliparib (FIG. 7e-f), providing an independent validation of the potential therapeutic application of PARPi on these leukemias. In order to further demonstrate PARP1 as the major molecular target for the observed phenotype, two independently validated shRNAs targeting mouse Parp1 (FIG. 7g-h) were used to replace PARPi in the RTTA. Consistent with the chemical inhibitor studies, both Parp1-shRNAs significantly suppressed the colony forming ability of cells transformed by AML1-ETO or PML-RARα (45-70%), but only had a modest impact on E2A-PBX and MLL-AF9 transformed cells (FIG. 1c-d and FIG. 7i), indicating a specific requirement of PARP in leukemic cells transformed by AML1-ETO or PML-RARα.

To investigate if PARPi could exert similar inhibitory effects on the corresponding human leukemias, we used patient-derived leukemic cell lines carrying AML1-ETO (Kasumi), mutated PML-RARα that is resistant to standard ATRA treatment (NB4-LR2)24, or MLL-AF9 (THP1) for the inhibitor studies. Analogous to the observation in the mouse primary transformed cells, PARPi treatment reduced the colony forming ability of Kasumi and NB4-LR2 but did not affect THP1 cells (FIG. 1e-f). To further demonstrate the potential in vivo efficacy, Kasumi, NB4-LR2 and THP1 cells were xeno-transplanted into immuno-compromised mice and subjected to the PARPi treatment. In spite of being used as a monotherapy, Olaparib treatment significantly delayed the disease onset driven by AML1-ETO from median survival of 55 days to 102 days (FIG. 1g, FIG. 7j, 7m, and Table S1), providing proof-of-principle evidence for the application of PARPi in AML1-ETO leukemia. Strikingly, Olaparib as a single agent could also effectively suppress disease onset induced by ATRA-resistant APL cells (FIG. 1h, FIG. 7k, 7n, and Table S2), highlighting its potential use for treatment-resistant APL25. In contrast, PARPi treatment had no effect on the survival of xenograft model transplanted with human THP1 cells carrying MLL-AF9 (FIG. 1i, FIG. 7l, 7o, and Table S3). To further substantiate these findings, we also observed very similar differential in vitro PARPi responses using primary AML patient samples carrying the corresponding translocation fusions, in which both AML1-ETO and PML-RARα (but not MLL fusion) primary human leukemia cells were highly sensitive to PARPi (FIG. 7p-q). Together, these results reveal the potential therapeutic utility of PARPi in different subtypes of leukemia driven by specific LATFs.

PARPi Treatment Induces Differentiation and Senescence

Figure 2G:
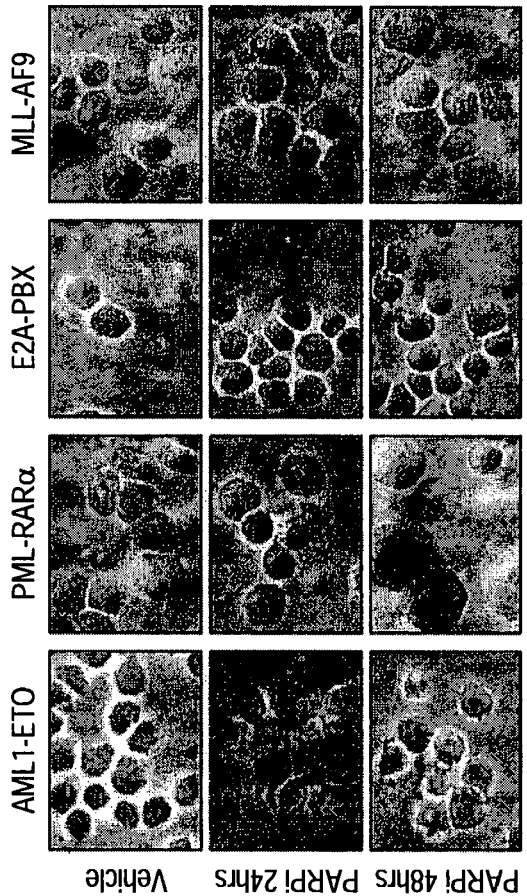
Figure 2I:
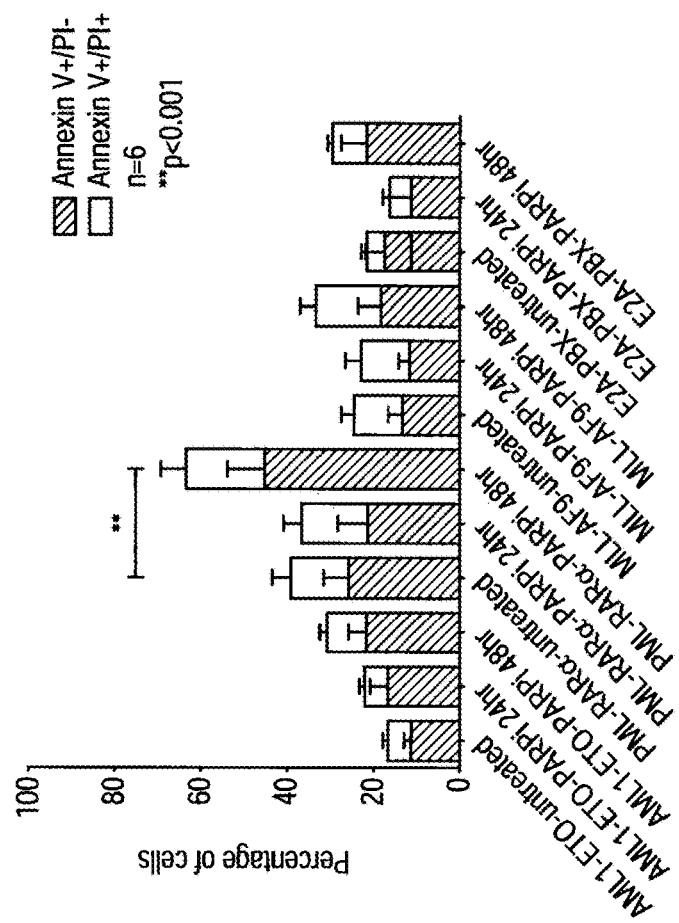
Figure 2H:
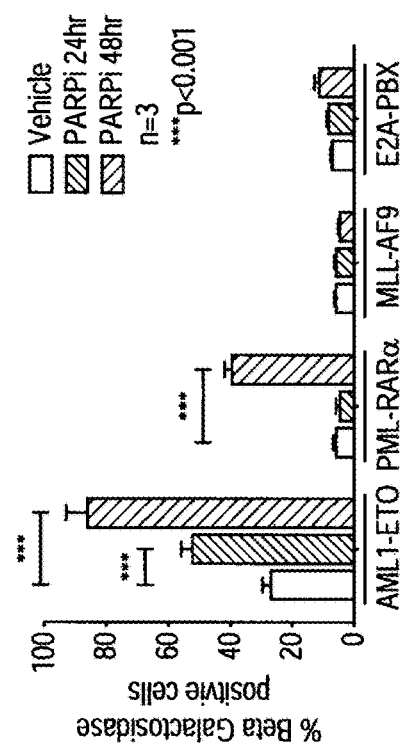
Figure 8A:
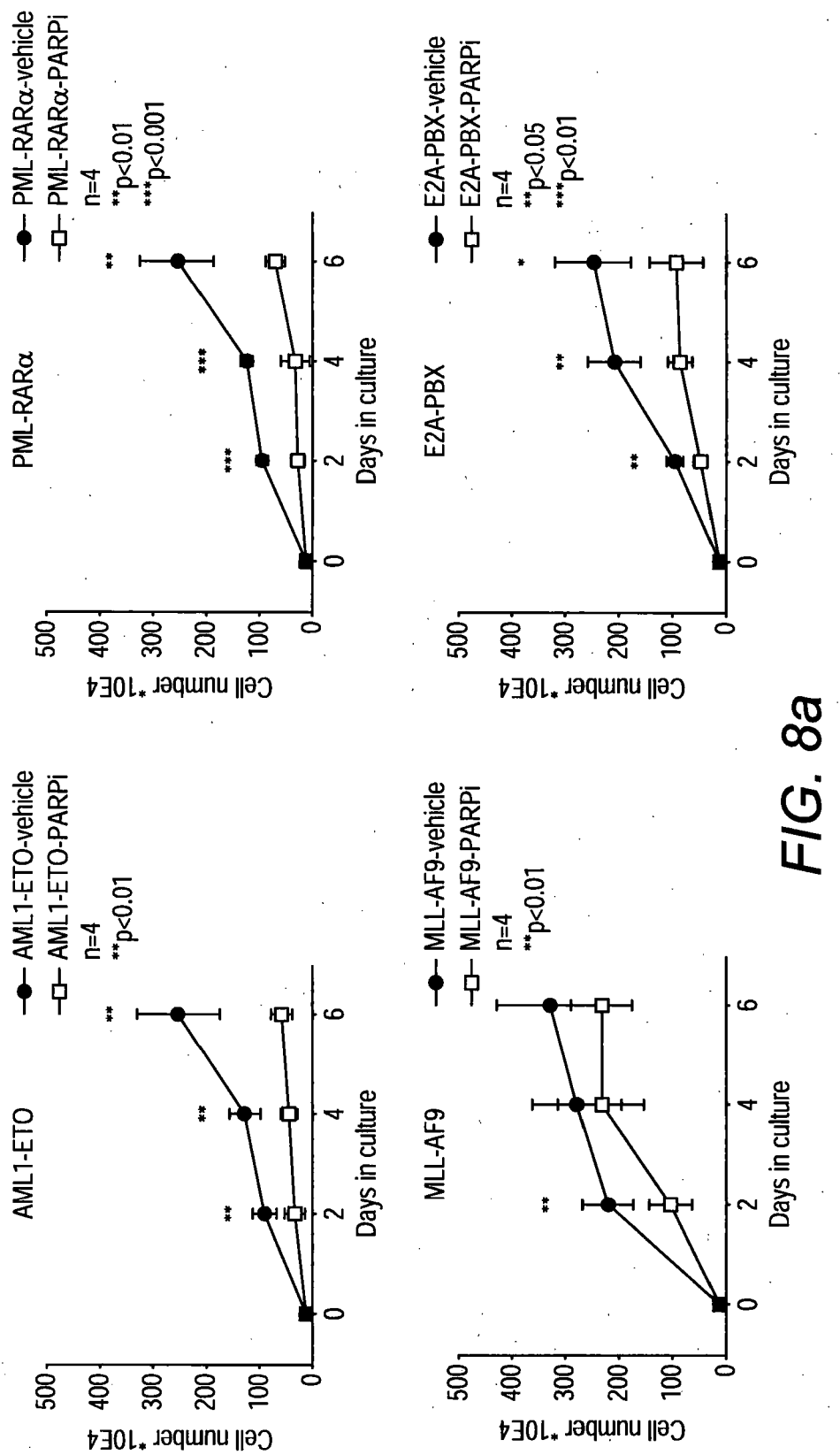
Figure 8B:
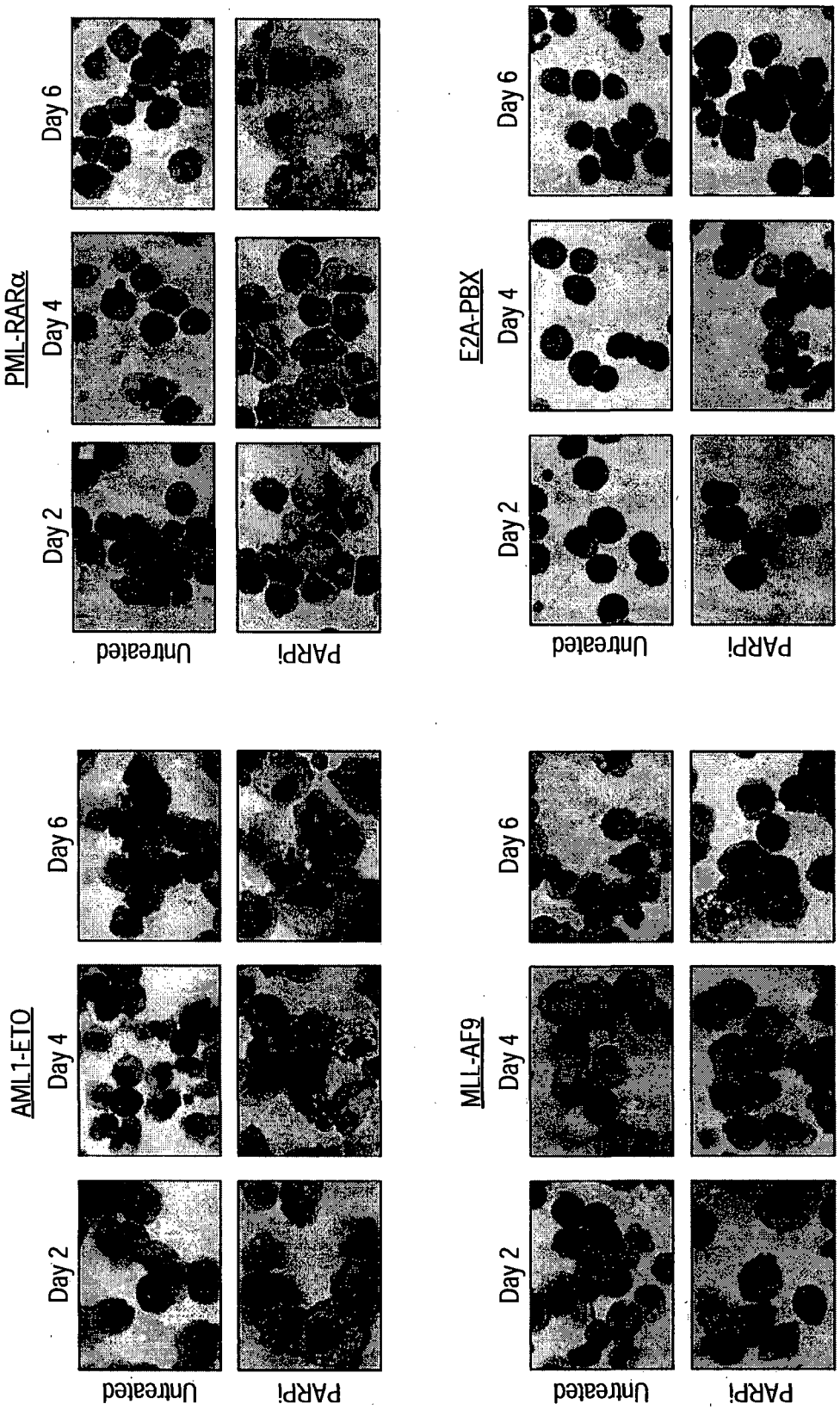
Figure 8C:
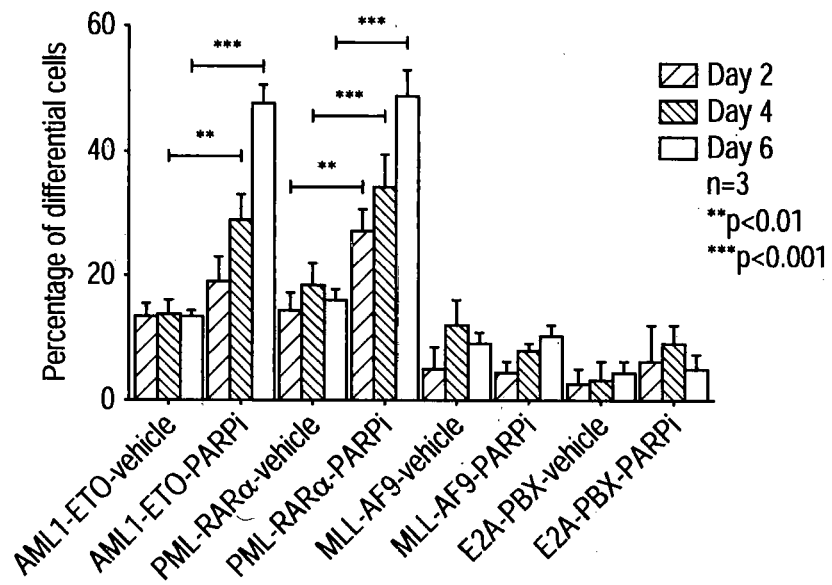
Figure 8D:
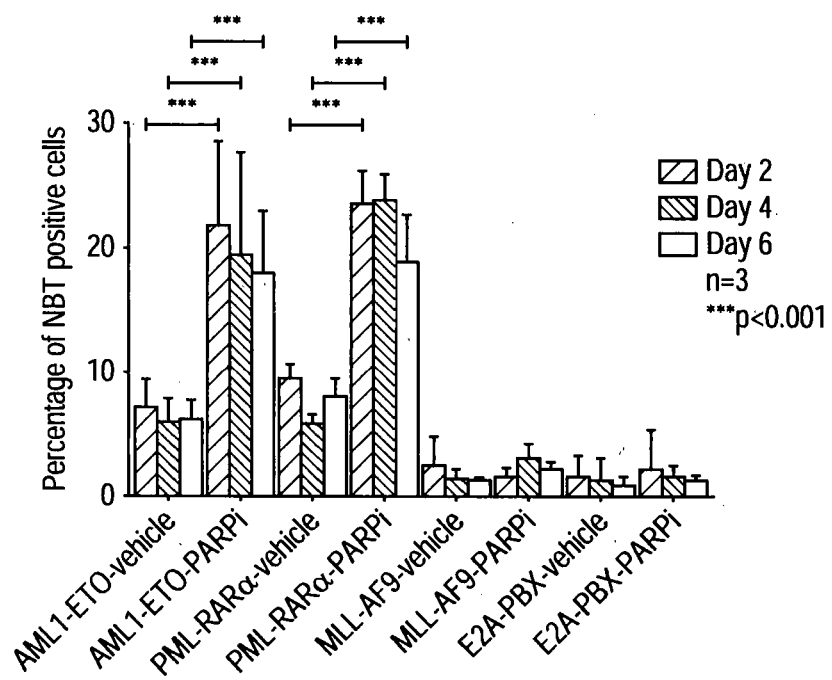
Figure 8E:
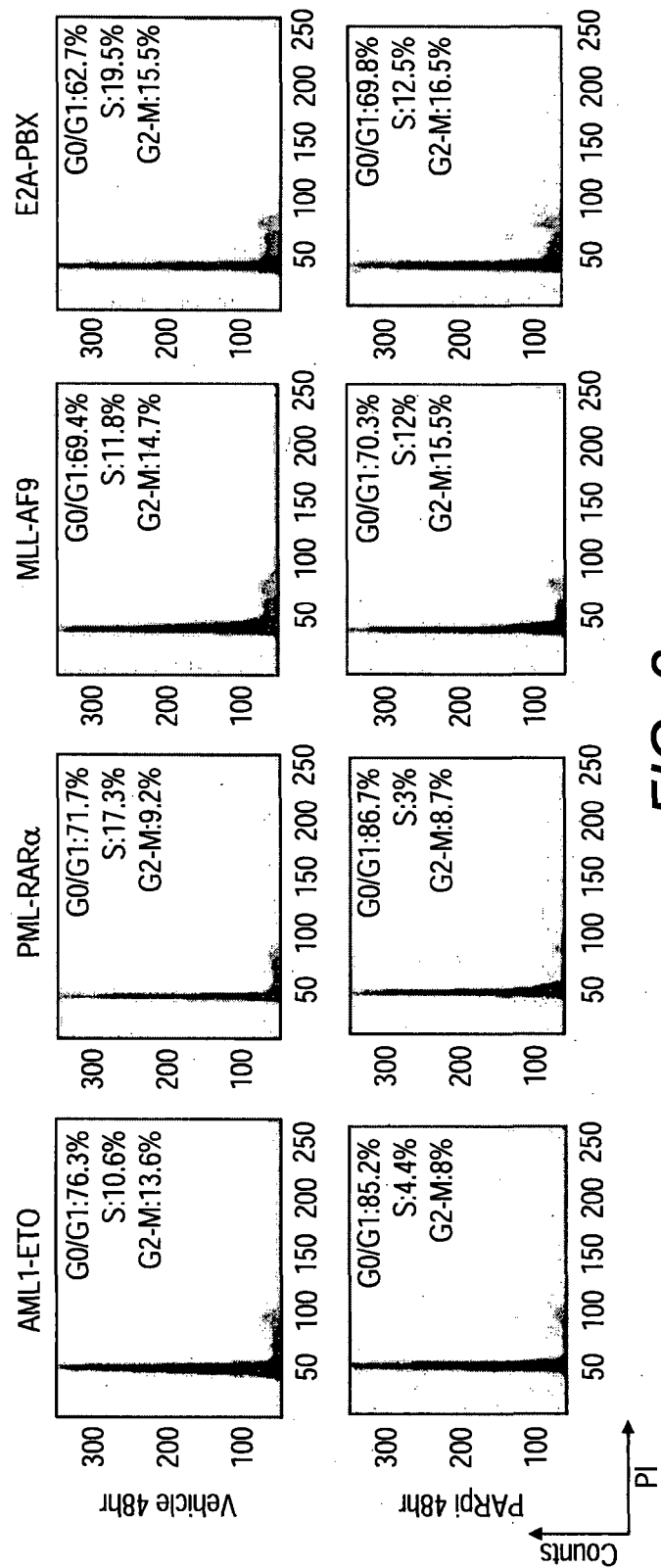
Figure 8F:
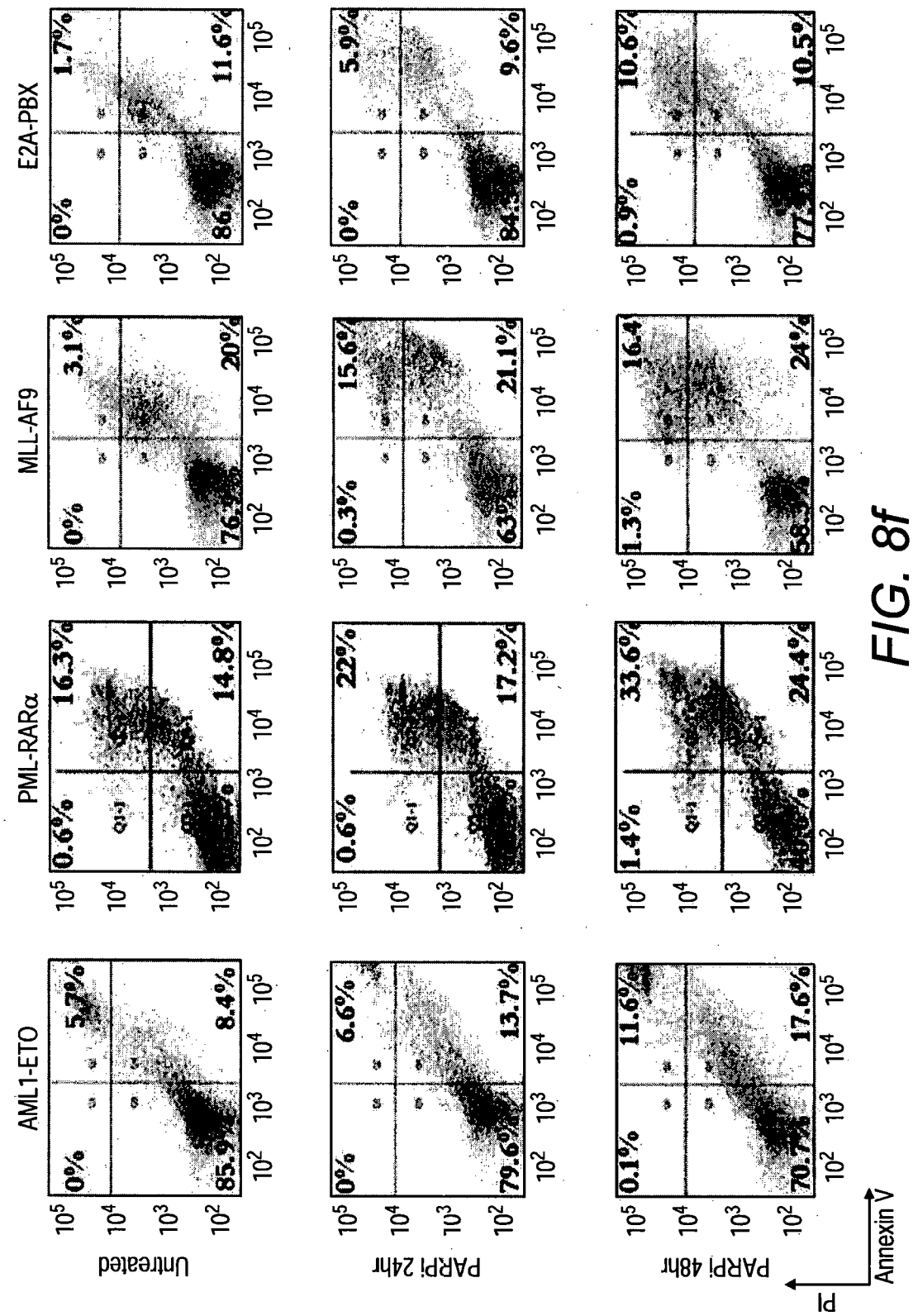

We next investigated the cellular processes being affected by PARPi in primary transformed cells that might explain the inhibitory effect. PARPi treatment on AML1-ETO and PML-RARα transformed cells in clonogenic assay resulted in their morphological differentiation into monocytic/granulocytic lineages (FIG. 2a-b). These results were consistent with the time course measurement of growth and differentiation by both morphology and NBT reduction assays, showing that PARPi could slow cell growth in general but significantly increased the percentage of differentiation only in AML1-ETO and PML-RARα cells (FIG. 8a-d). These findings corroborate with recent observations of leukemic differentiation induced by excessive DNA damage[26], suggesting that differential DDR may underlie the contrasting PARPi responses. PARPi treatment was also accompanied by cell cycle G1 arrest (FIG. 2c and FIG. 8e), up-regulation of p53 and p21 (FIG. 2d-e). Consistently, we also detected an increase of p16 expression in AML1-ETO and PML-RARα transformed cells (FIG. 2f), which underwent significant senescence upon PARPi treatment (FIG. 2g-h). PARPi also induced apoptosis of PML-RARα transformed cells (FIG. 2i and FIG. 8f). In contrast, none of these effects were observed in E2A-PBX or MLL-AF9 transformed cells in spite of a small upward trend in differentiation and apoptosis noted in these primary transformed mouse cells upon PARPi treatment (FIG. 2a-i). To further extend our findings to the corresponding human leukemias, similar assays were performed on the human leukemia cell lines and primary human patient samples carrying the translocation fusions. In accord with the results in the mouse models, PARPi could effectively induce senescence and apoptosis in Kasumi and NB4-LR2 but not THP1 (FIG. 8g-i); and increased differentiation of primary AML cells carrying AML1-ETO and PML-RARα but not MLL fusions (FIG. 8j-l). These results consistently suggest a specific requirement of PARP function in the leukemic cells transformed by AML1-ETO and PML-RARα.

AML1-ETO and PML-RARα Transformed Cells Show Inherent DDR Defects

Figure 3A:
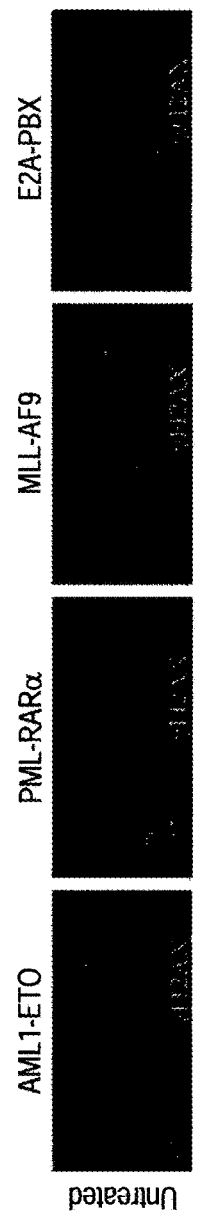
Figure 3B:
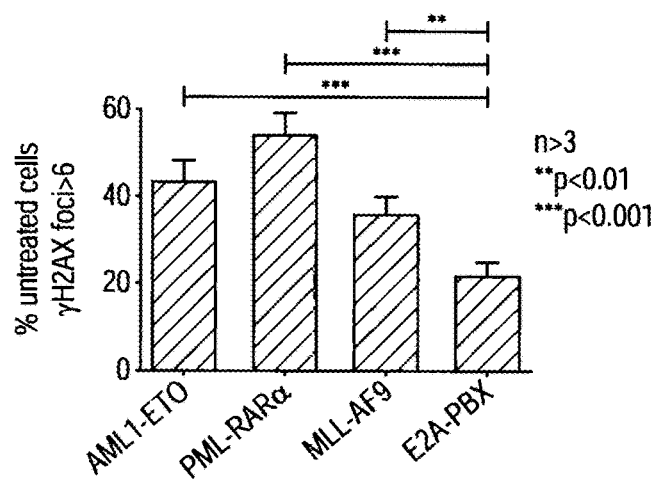
Figure 3C:
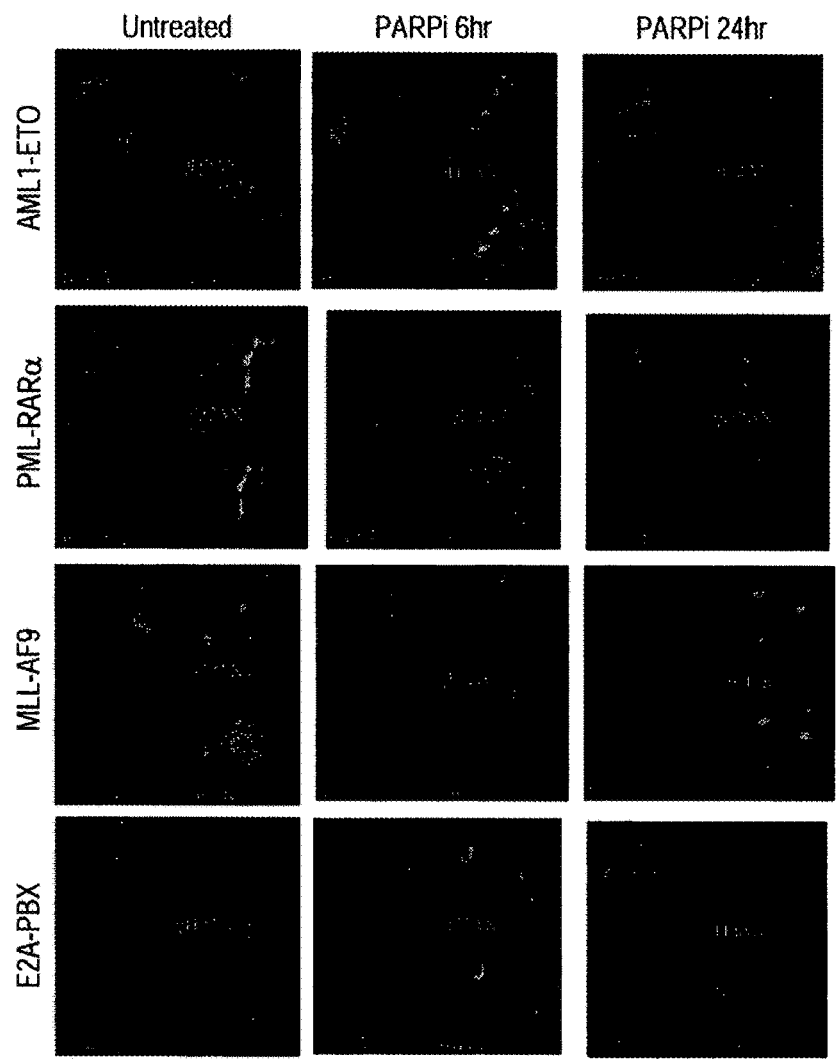
Figure 3D:
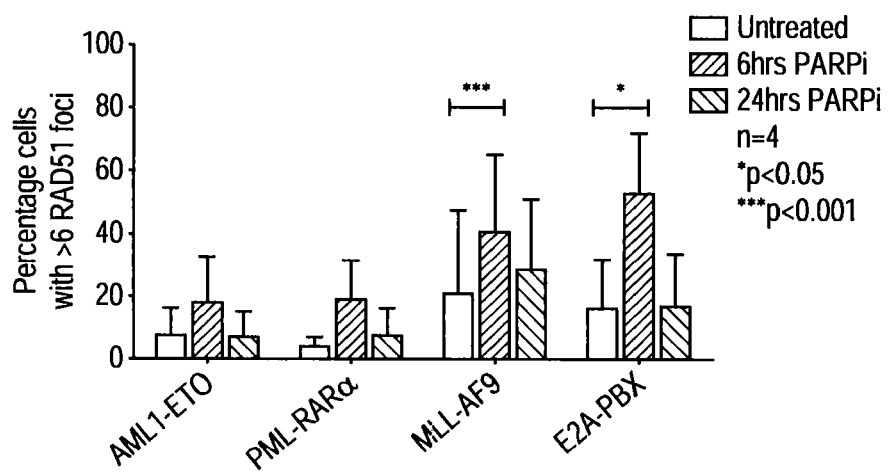
Figure 3E:
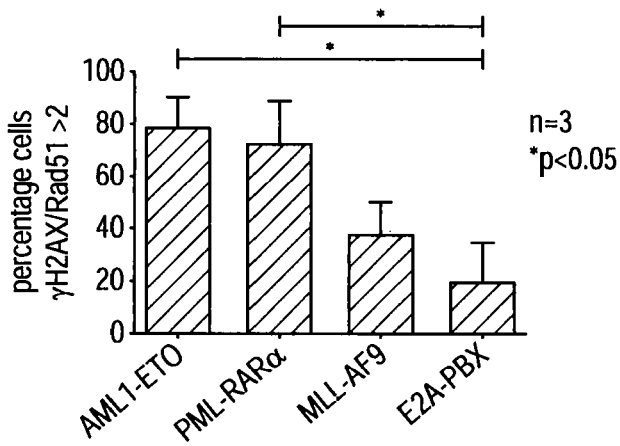
Figure 9C:
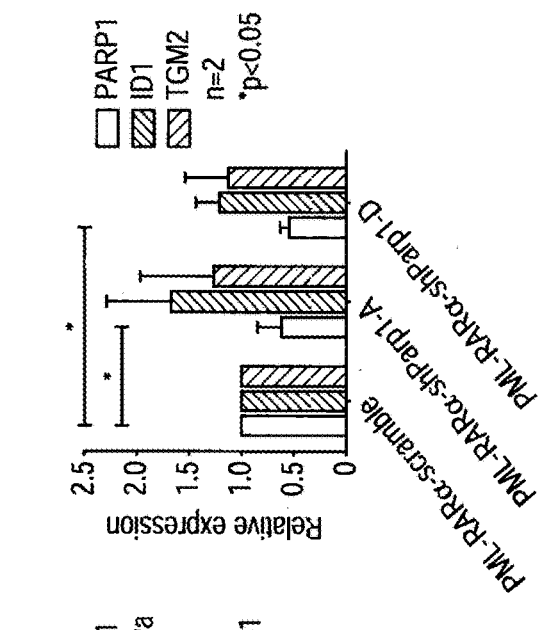
Figure 9B:
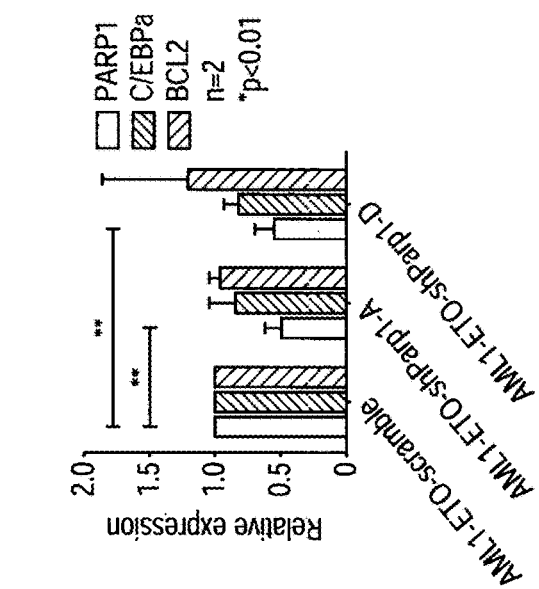
Figure 9A:
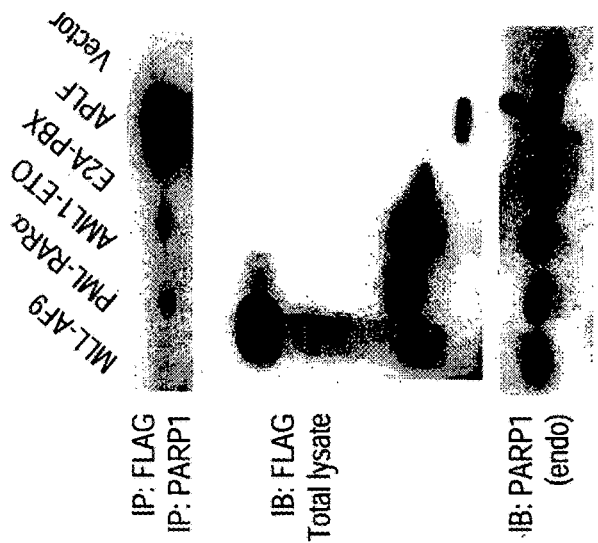
Figure 9D:
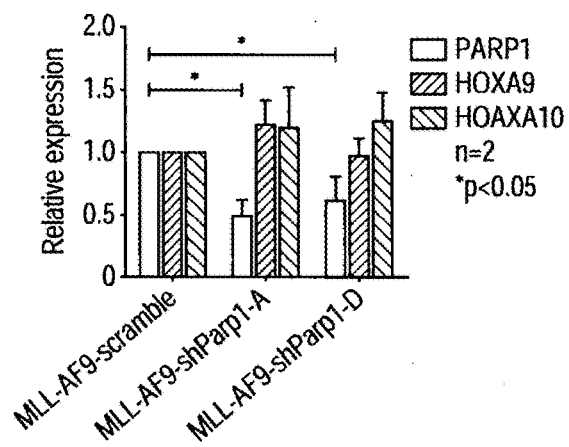
Figure 9E:
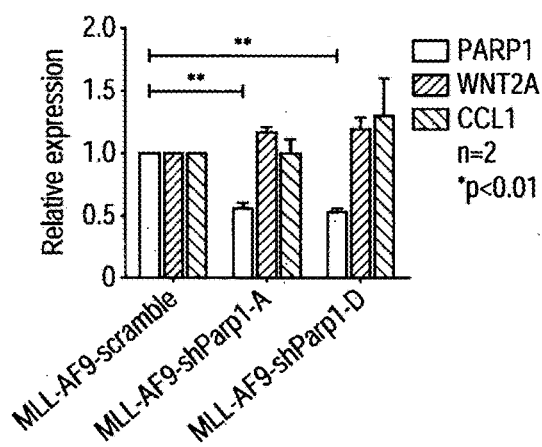
Figure 9F:
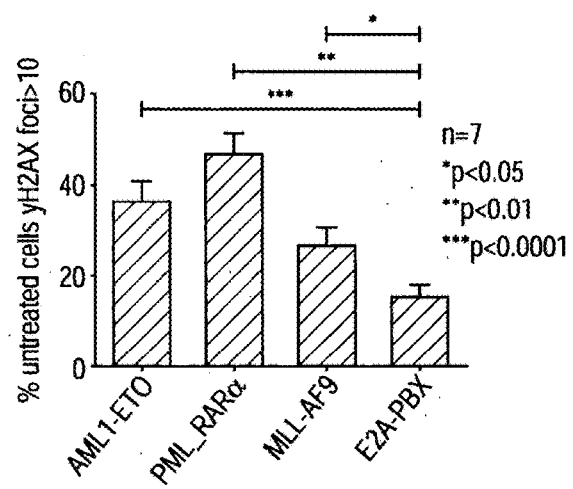
Figures 9I, 9J:
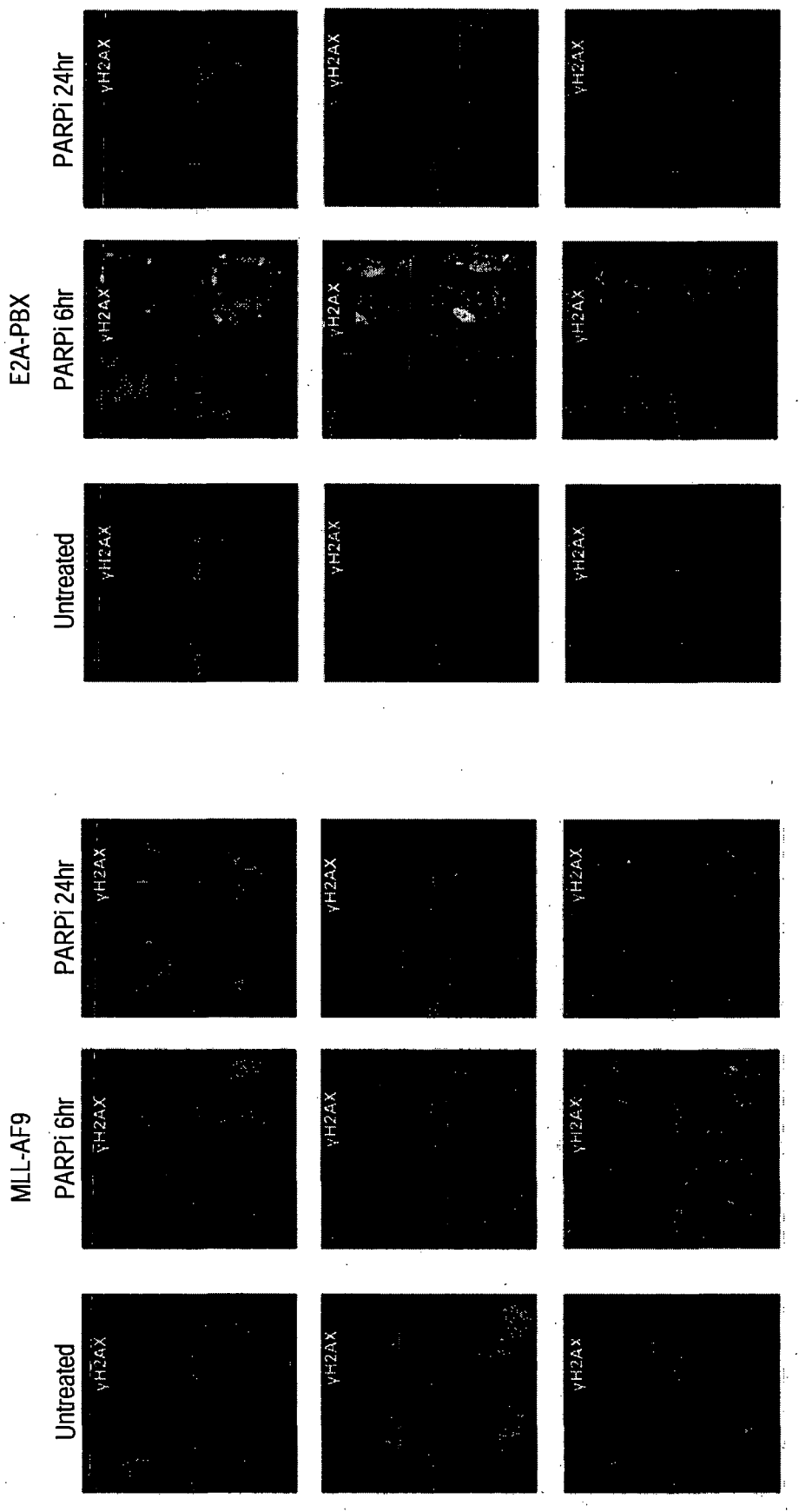
Figure 9N:
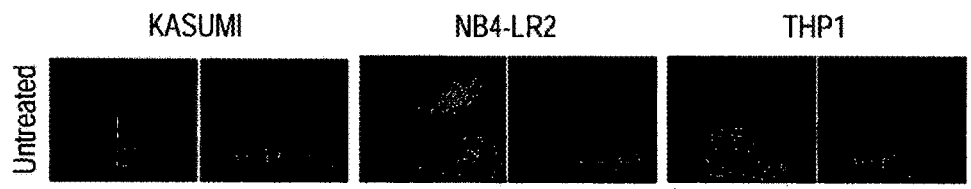
Figure 9O:
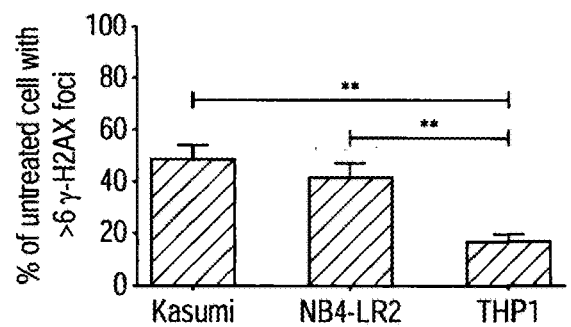
Figure 9P:
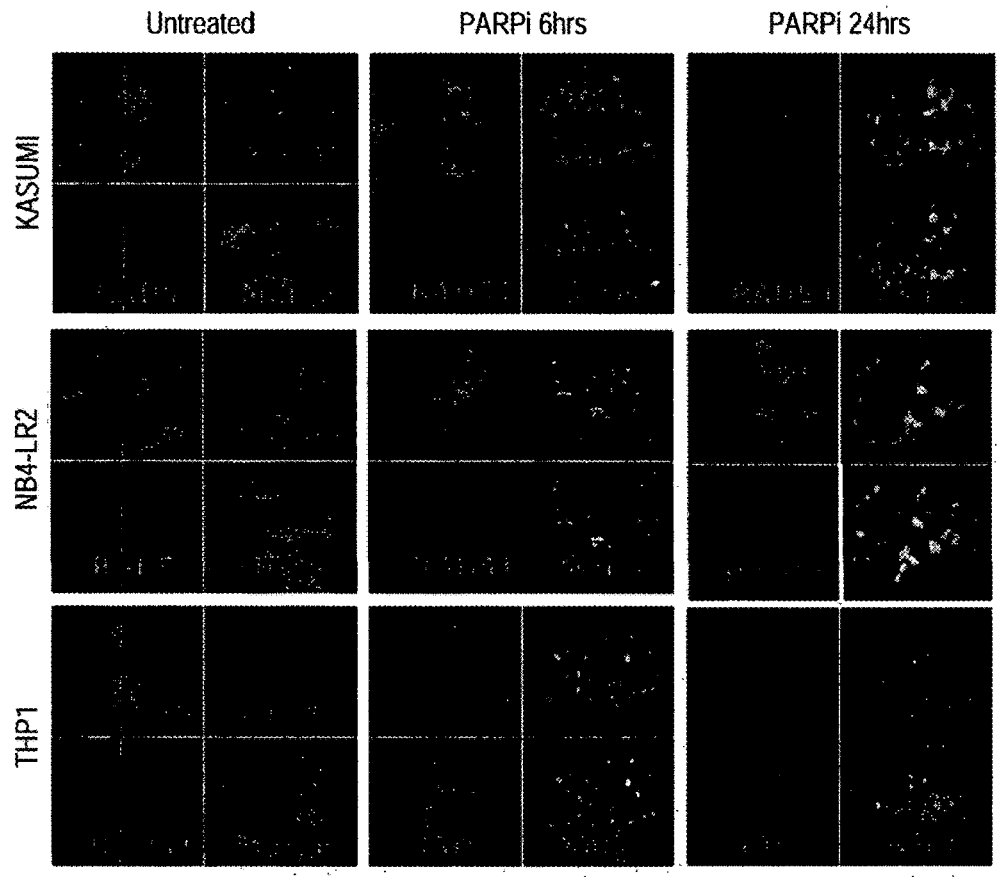

Although the general rationale behind the PARPi sensitivity is a defect in DDR[3,4,15,16,27], PARP also has transcriptional functions involved in gene regulation[1,28]. After the biochemical and transcriptional approaches detected no direct biochemical interaction (FIG. 9a and unpublished mass spectrometry data) and transcriptional regulation (FIG. 9b-e) between PARP1 and any of these fusion proteins, we assayed DNA damage and the kinetics of the DDR in the primary transformed cells by analyzing the frequency of Ser-139 phosphorylated γ-H2AX foci, which is considered as an early cellular response to DSBs, and the most well established chromatin modification linked to DNA damage and repair[29]. With the exception of E2A-PBX, untreated AML1-ETO, PML-RARα and MLL-AF9 transformed cells displayed significant levels of γH2AX-positive DNA damage foci (with both criteria of >6 and >10 foci), indicative of ongoing DNA damage or replication stress (FIG. 3a-b, FIG. 9f). Upon PARPi treatment, both PARPi insensitive (E2A-PBX and MLL-AF9 cells) and sensitive cells (AML1-ETO and PML-RARα) showed further inductions of γH2AX foci (FIG. 3c, FIG. 9g-k), suggesting that PARPi treatment induced DNA damage regardless of the oncofusion proteins expressed by the transformed cells. As PARPi have been demonstrated to selectively target HR deficient cells[3,15,16], we investigated whether PARPi sensitive cells were incapable of effective recruitment of Rad51 to DNA damage sites, as a readout of HR efficiency[30,31]. Upon PARPi treatment for 6 hours, E2A-PBX or MLL-AF9 cells, were able to form RAD51 foci (with both criteria of >6 and >10 foci), which then returned to basal level after the repair in 24 hours (FIG. 3c-d, FIG. 9g-j, l). In a stark contrast, no significant Rad51 recruitment was observed in AML1-ETO or PML-RARα transformed cells (FIG. 3c-d, Supplementary FIG. 3g-j, l), in which around 80% of the cells showed γH2AX and Rad51 foci ratio greater than 2 (FIG. 3e), indicating their HR deficient nature. The observed differential HR deficiency associated with PARPi treatment cannot be due to different cell cycle status of these cells, as PARPi exhibited no significant effect on cell cycle progression in first 24 hours (FIG. 9m) when these assays were performed. To further extend our findings to the human disease, human leukemia cell lines carrying the corresponding fusions were also subjected to similar DDR assays. Consistently, we observed higher levels of DNA damage in untreated Kasumi and NB4-LR2 cells (FIG. 9n-o), which also failed to effectively induce Rad51 repair foci upon PARPi treatment as compared with THP1 (FIG. 9p-r).

Figure 3F:
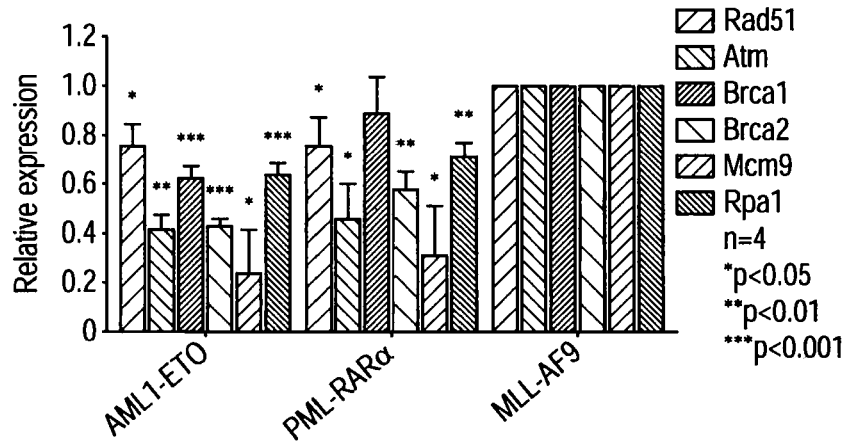

To gain further insights into the differential impacts of LATF on DDR, we investigated the expression of the major HR mediators and revealed a decreased expression of key HR genes including Rad51, Atm, Brca1 and Brca2 in both AML1-ETO and PML-RARα mouse models (FIG. 3f). To validate these findings in the corresponding human leukemias, we analysed the expression array data of these genes in patient samples carrying these distinctive LATFs32. Consistently, we observed very similar suppression of a large number of HR mediators in AML1-ETO and PML-RARα human leukemic cells as compared with MLL rearranged leukemia (FIG. 3g, Table S4). These results could be independently confirmed by a second set of array data from different patient cohorts[33] (FIG. 9s). We also further validated the results of two key HR mediators, RAD51 and BRCA2, at the protein level by Western blot using mouse primary leukemic cells transformed by the corresponding fusions (FIG. 3h), although the differential expression of RAD51 was milder than BRCA2, which were in line with the RNA expression data (FIG. 3f). These results consistently suggest that suppression of HR genes is a distinctive feature shared by PARPi sensitive AML1-ETO and PML-RARα transformed cells. To further assess the direct effect of these fusion proteins on DNA repair efficiency, we performed both plasmid end-joining assay34 and HR reporter assay[35]. Nuclear extracts from E2A-PBX and MLL-AF9 transformed cells could efficiently repair DSB and produced significantly higher total numbers of colonies as compared to those by AML1-ETO and PML-RARα transformed cells (FIG. 3i). Moreover, in contrast to E2A-PBX and MLL-AF9, most of the end-repairs by AML1-ETO or PML-RARα nuclear extracts were mis-matched (FIG. 3j). Consistently, we also observed significant suppression of HR efficiency upon expression of AML1-ETO or PML-RARα as opposite to a small notable and significant increase of HR efficiency by MLL-AF9 (FIG. 3k). Therefore these data indicate that leukemic cells driven by AML1-ETO and PML-RARα had a reduced ability to repair DSBs and that the repairs accompanied with an increased error rate, which may form the basis for their increased PARPi sensitivity.

Induction of Hoxa9 Expression by MLL Fusions Modulates PARPi Sensitivity

To gain novel mechanistic insights regulating the PARPi sensitivity, we analysed PARPi-resistant MLL leukemic cells, which showed a high basal level of phosphorylated γH2AX (FIG. 3a-b) but were able to efficiently recruit Rad51 to the DNA damage foci (FIG. 3c-d) and survived PARPi treatment (FIG. 1-2), suggesting HR competency. In contrast to AML1-ETO and PML-RARα 19,23, MLL fusion proteins recruit chromatin remodeling enzymes and transactivation complexes culminating in the expression of critical downstream genes, including the homeodomain transcription factor HOXA919,36,37, which has been previously identified as one of the single most critical independent poor prognostic factors associated with inferior treatment response in AML38 and its suppression has been linked to the drug resistant phenotype in glioblastoma 39,40. Consistently, we could observe specific and differential activation of Hoxa9 by MLL fusion in our mouse models and independent human patient data (FIG. 10a-c). Thus we hypothesized that the PARPi resistance exhibited by MLL-AF9 transformed cells might be dependent on its ability to activate Hoxa9 expression. To this end, we assessed the functional requirement of Hoxa9 in conferring PARPi resistance in MLL-AF9 transformed cells using RTTA in combined with a Hoxa9 knockout mouse model.

Figure 4A:
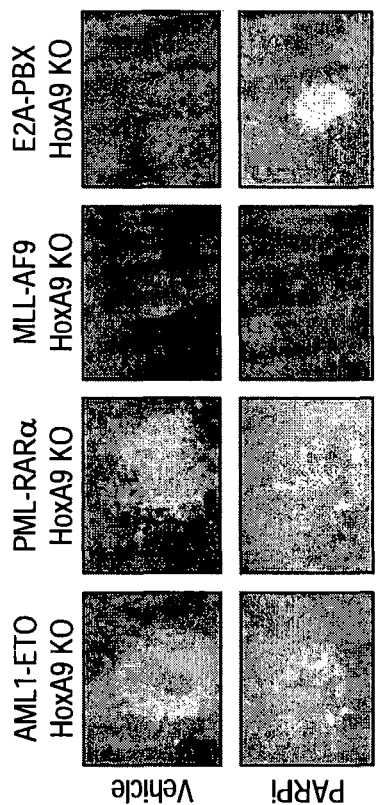
Figure 4B:
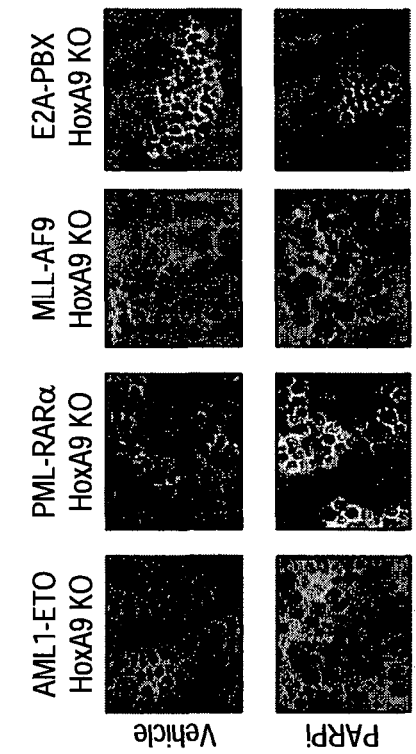
Figure 4C:
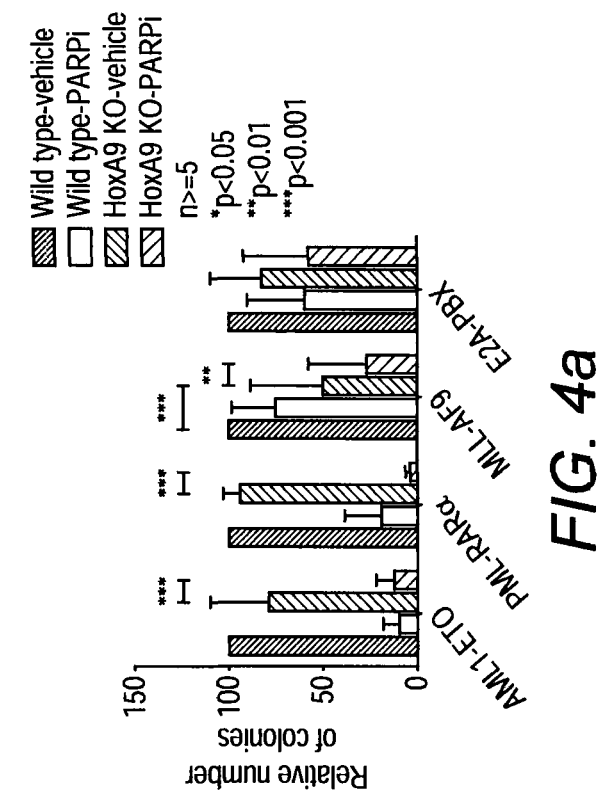
Figure 4D:
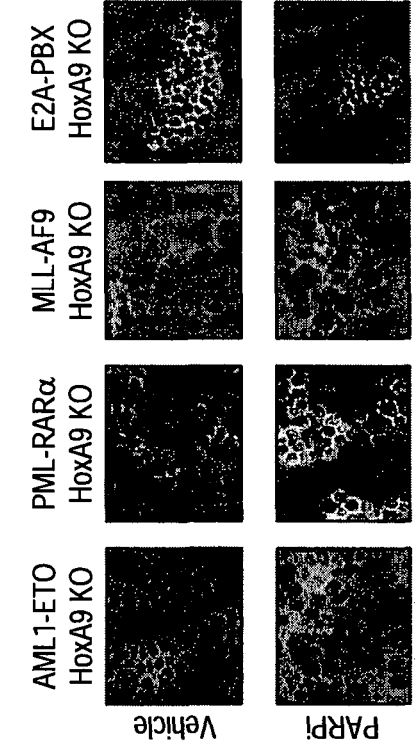
Figure 4E:
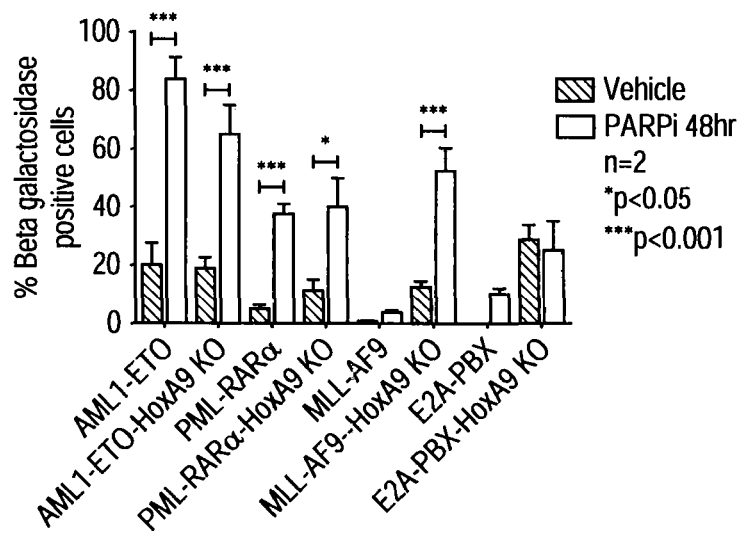
Figure 4F:
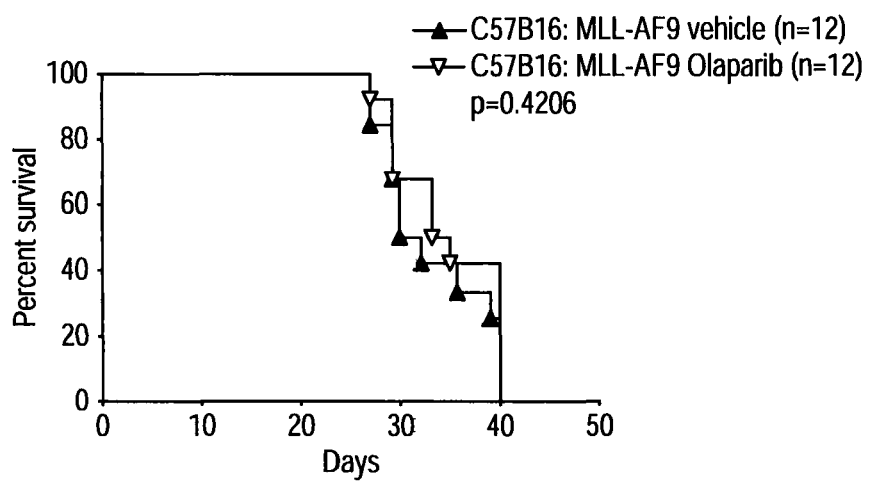
Figure 10D:
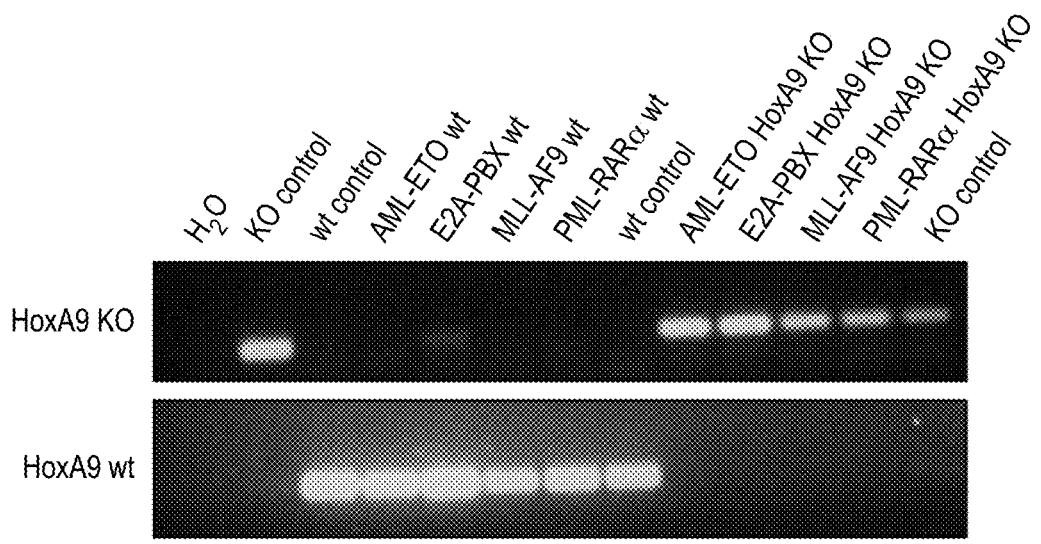
Figure 10E:
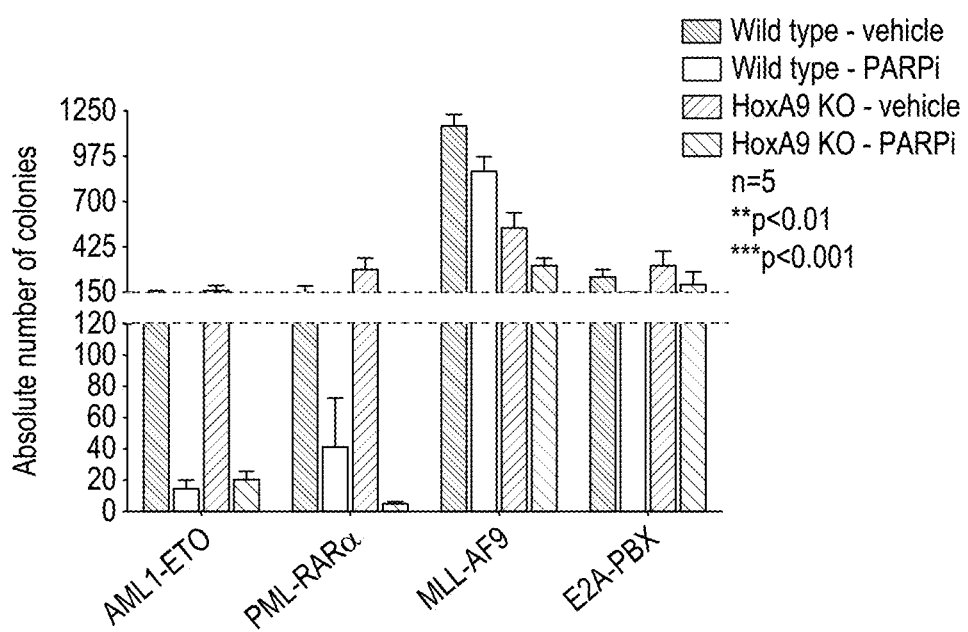
Figure 10F:
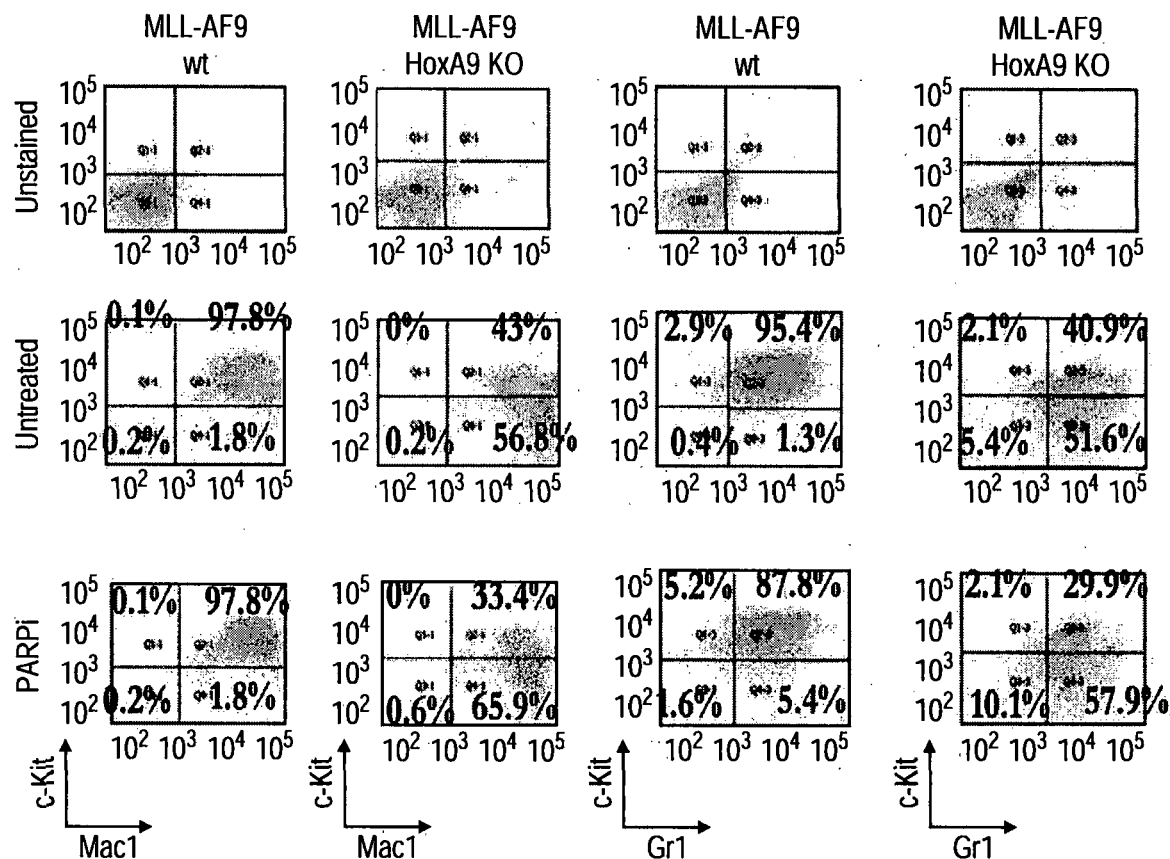
Figure 10G:
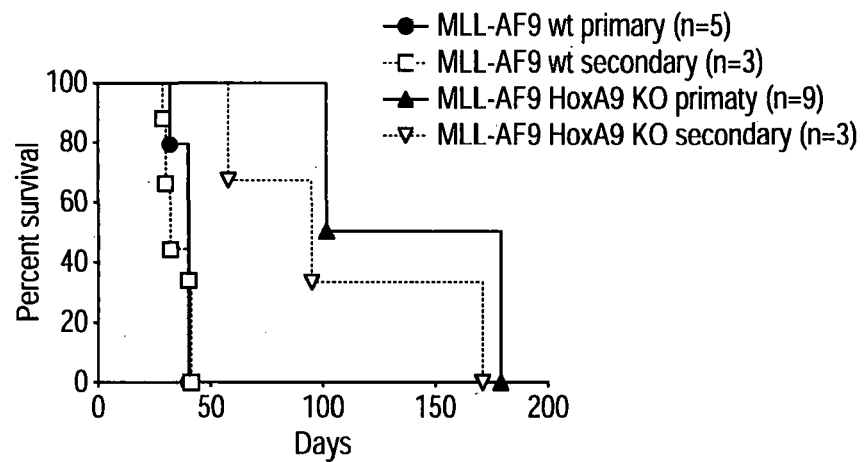
Figure 10H:
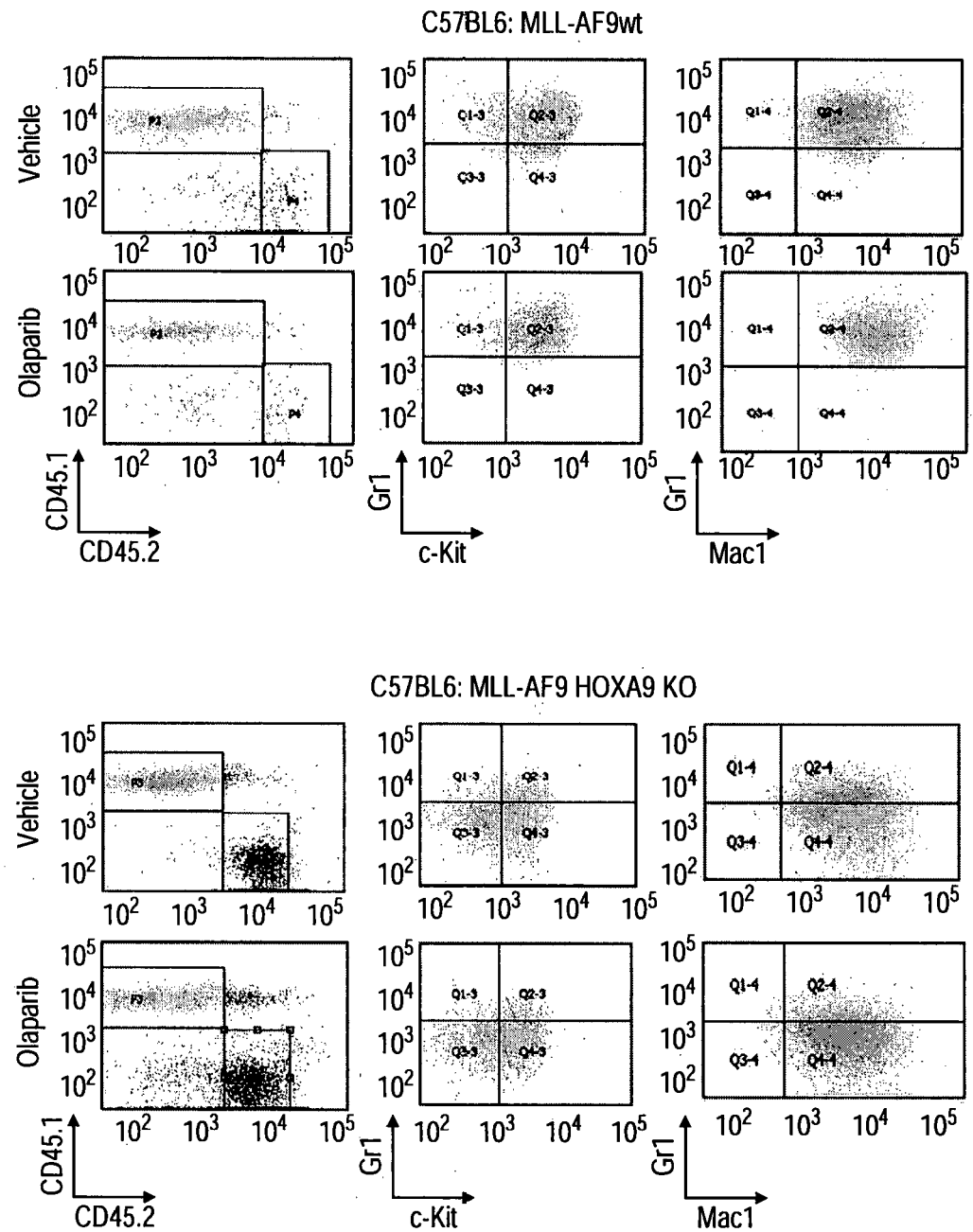
Figure 10I:
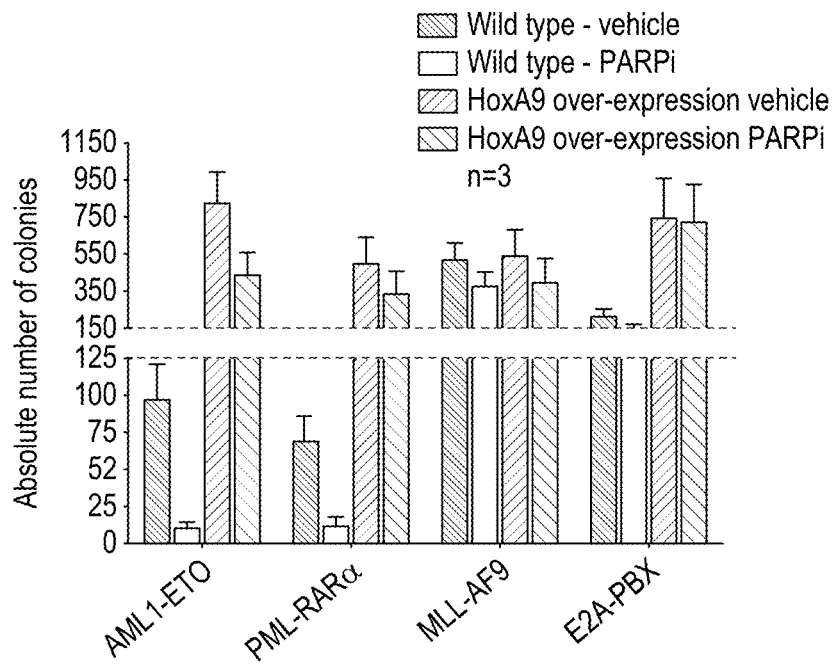
Figure 10J:
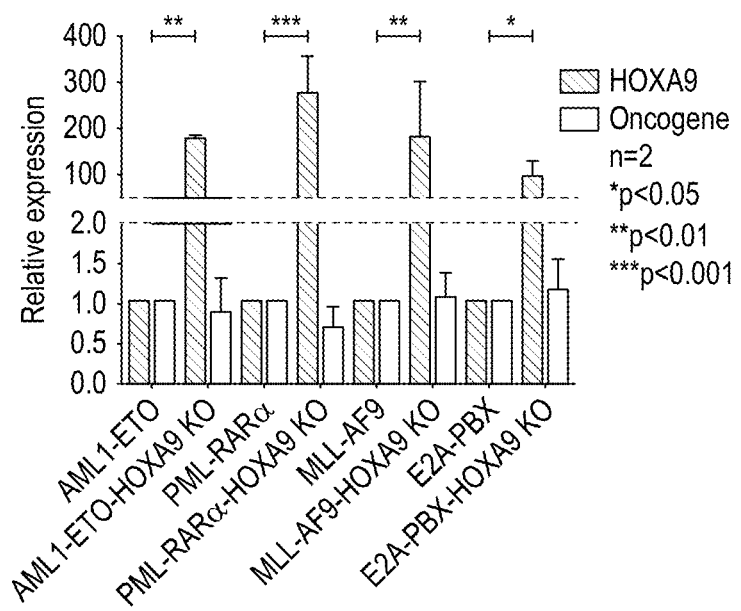

Consistent with the previous report[23,41,42], Hoxa9 knockout had relatively modest effect on both in vitro and in vivo transformation mediated by MLL-AF9 its spite of a more mature phenotype and a slightly reduced colony forming ability as compared with their wild type counterpart 41 (FIG. 4a-c and FIG. 10d-g). Strikingly, ablation of Hoxa9 expression sensitized MLL-AF9 transformed cells to PARPi treatment, which resulted in a significant suppression of colony forming ability and differentiation of MLL-AF9 transformed cells (FIG. 4a-c and FIG. 10e-f). In contrast, Hoxa9 knockout had a modest effect on E2A-PBX transformed cells, which have previously been shown as an Hoxa9 independent oncofusion[23,43] (FIG. 4a-c and FIG. 10d-e). We also observed induction of senescence in MLL-AF9 Hoxa9−/− transformed cells upon PARPi treatment (FIG. 4d-e), which is consistent with the role of Hoxa9 in suppressing cellular senescence[23], a common endpoint of excessive DNA damage. These data indicate that Hoxa9 may play a key role in mediating PARPi resistance in MLL transformed cells, and its suppression in combination with PARPi may represent a novel avenue for targeting MLL leukemia. To this end, we tested the in vivo efficacy of this approach using MLL-AF9 full-blown leukemic cells derived from primary transplanted mouse, which closely mimic the advanced clinical stage of the corresponding human disease[22]. As expected, Olaparib treatment did not have any significant effect on mice transplanted with wild type MLL-AF9 leukemic cells (FIG. 4f, FIG. 10h and Table S5). In contrast, while Hoxa9 deficient MLL-AF9 leukemic cells could efficiently induce leukemia, they were highly sensitive to PARPi treatment, which significantly delayed the disease latency (FIG. 4g, FIG. 10h and Table S6), indicating a critical function of Hoxa9 in mediating PARPi resistance in MLL leukemia.

To further demonstrate the role of Hoxa9 in mediating PARPi resistance, we also employed a gain of function approach by over-expressing Hoxa9 in PARPi sensitive AML-ETO and PML-RARα leukemic cells. As expected, AML1-ETO and PML-RARα cells transduced with the vector control remained sensitive to PARPi treatment. Interestingly, forced expression of Hoxa9 conferred PARPi resistant to AML1-ETO and PML-RARα cells without affecting the expression of the fusions (FIG. 4h-j and FIG. 10i-j); AML1-ETO or PML-RARα cells co-transduced with Hoxa9 could still form compact colonies with immature myeloblast phenotypes upon PARPi treatment. Hoxa9 expression also suppressed PARPi-induced senescence in AML1-ETO and PML-RARα cells (FIG. 4k-l). Together with the loss of function data, these results strongly suggest that Hoxa9 plays a key role in mediating PARPi resistance in leukemic cells.

Figure 5A:
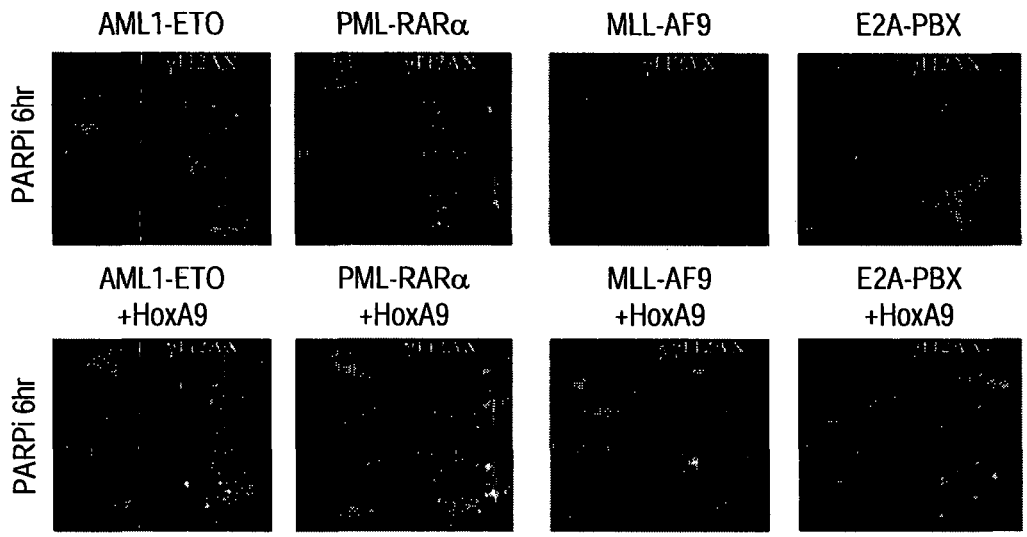
Figure 5B:
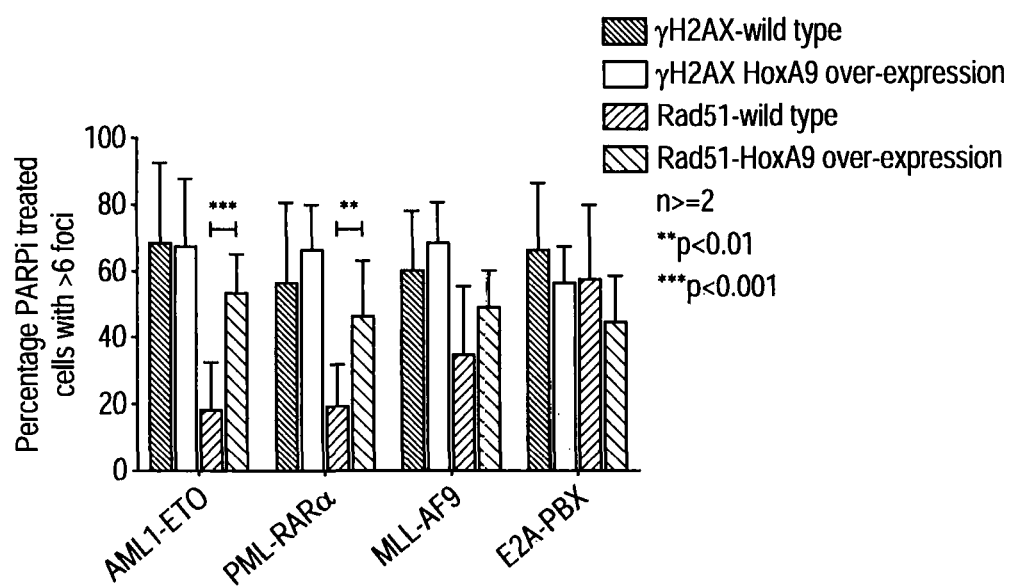
Figure 5G:
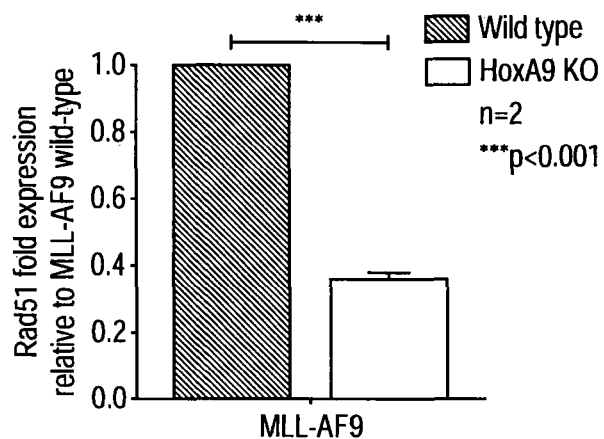
Figure 5H:
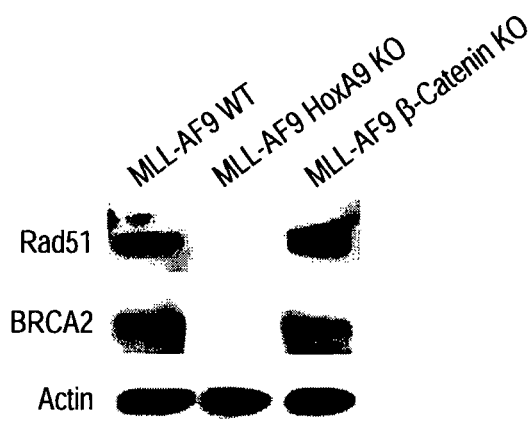
Figure 5I:
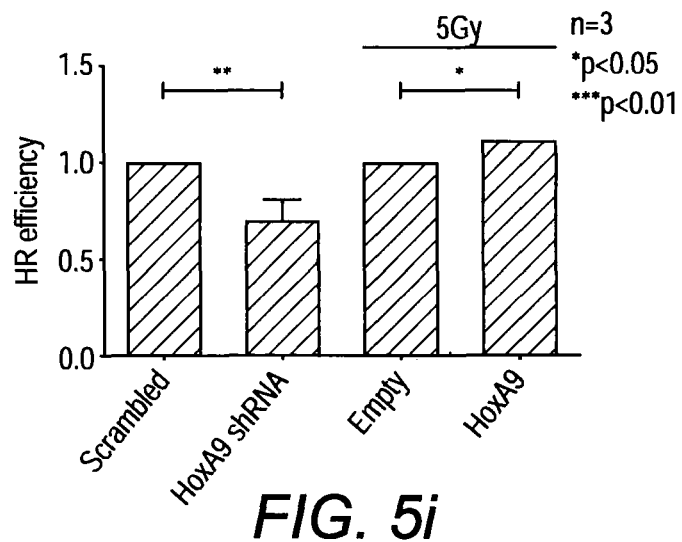

Hoxa9 Activates Expression of HR Gene Expression, Promotes Rad51 Foci Formation and DNA Repairs Given that the primary effect of PARPi treatment is on DNA repair, we analysed the effect of Hoxa9 in mediating DDR in transformed cells. In contrast to AML1-ETO and PML-RARα transformed cells, which were incompetent to mount significant Rad51 repair foci at DNA damage sites upon PARPi treatment (FIG. 3c), Hoxa9 over-expression conferred on these cells the ability to efficiently recruit Rad51 to DNA damage foci (FIG. 5a-b). Over-expression of Hoxa9 had modest effects on E2A-PBX or MLL-AF9 transformed cells, which already showed efficient recruitment of Rad51 (FIG. 5a-b). Conversely, suppression of Hoxa9 expression resulted in a significant impairment of Rad51 recruitment in MLL-AF9 transformed cells (FIG. 5c-d), leading to the hypothesis that Hoxa9 might be an upstream regulator of Rad51. To this end, we analyzed the expression array data of known Hoxa9 downstream targets in primary transformed myeloid cells[44,45]. The gene set enrichment analysis (GSEA) and gene ontology analysis (GO) revealed that genes involved in DNA repair, especially DNA repair with homologous recombination, were significantly enriched in HOXA9 responsive gene set (FIG. 5e, FIG. 11a-b, and Table S4). These results were also confirmed by RT-qPCR in Hoxa9 knockout MLL-AF9 transformed cells (FIG. 11c). Among them were key HR genes including Rad51[12,30,31], which was further validated in the primary transformed cells by both Hoxa9 over-expression (FIG. 5f) and knockout approaches (FIG. 5g). The regulation of RAD51 and BRCA2 expression by Hoxa9 in MLL-AF9 cells were also demonstrated at the protein level, where the expressions of these two proteins were significantly diminished in the absence of Hoxa9 (but not β-catenin control) (FIG. 5h). While these results consistently suggest an important involvement of common HR genes (e.g., Rad51 and Brca2) in mediating differential PARPi responses exhibited by different LATFs, there are also likely other HR targets uniquely regulated by individual LATFs that also contribute to their differential responses. Finally, to demonstrate a direct involvement of HOXA9 in DDR, HR-reporter assays further revealed an enhanced HR efficiency by Hoxa9 expression as opposite to a compromised HR response upon its suppression (FIG. 5i). These data strongly suggest that Hoxa9 confers resistance to PARPi in part by activating DDR transcription programs.

Targeting PARPi Resistant AML with a Combination Approach

Figure 6C:
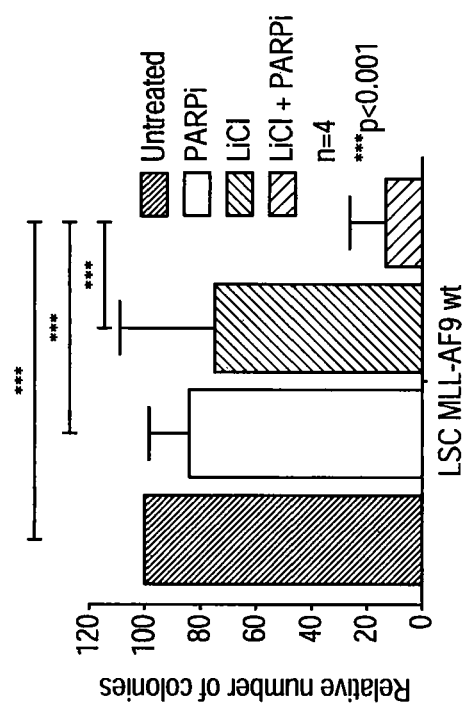
Figure 6E:
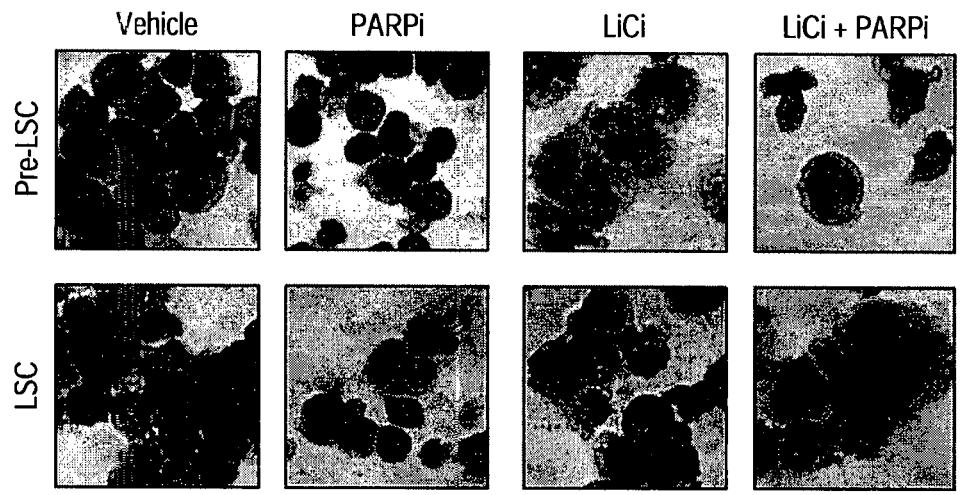
Figure 6F:
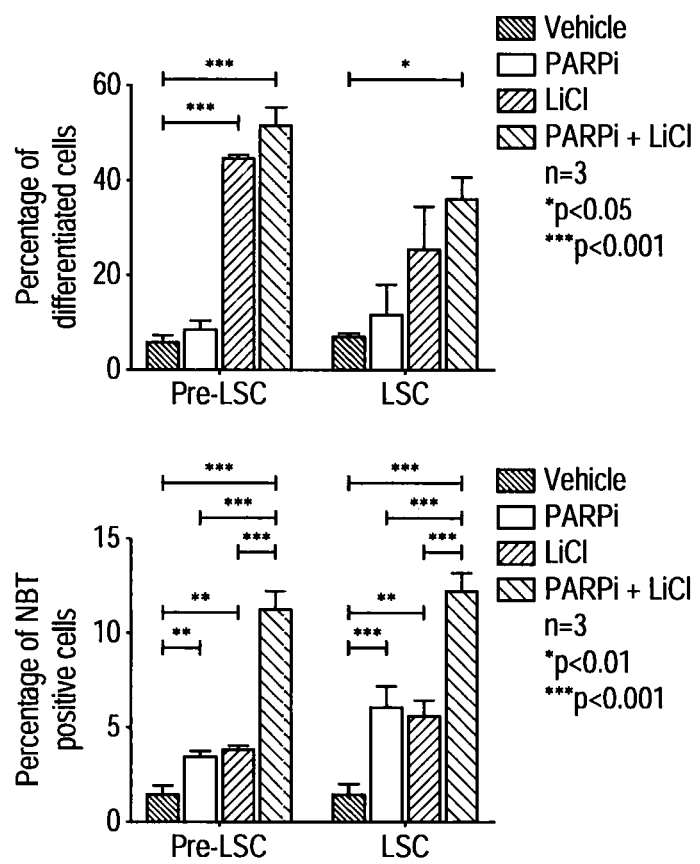
Figure 6H:
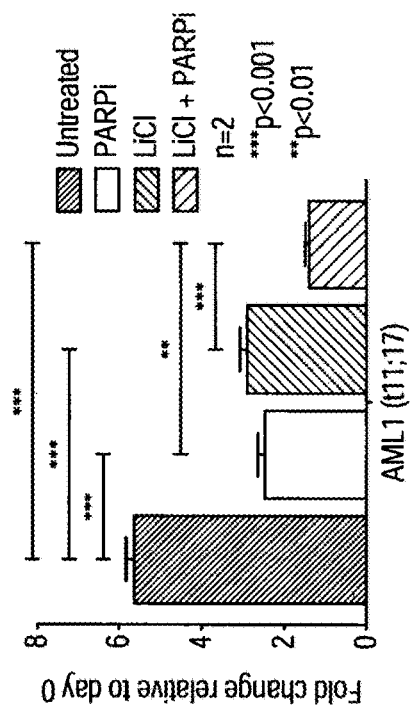
Figure 6J:
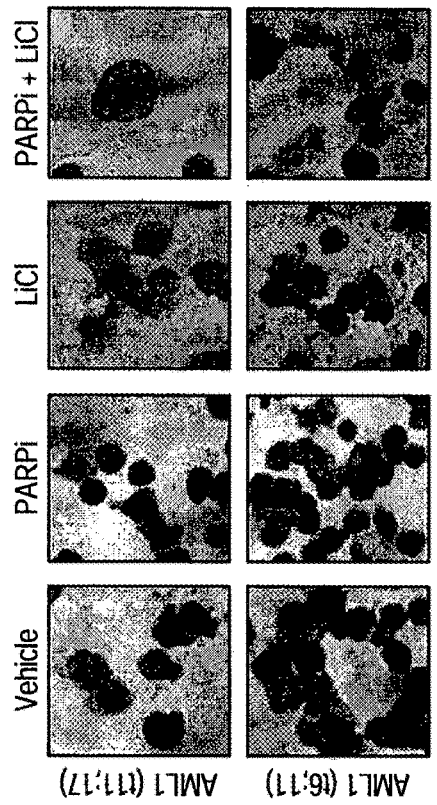
Figure 6G:
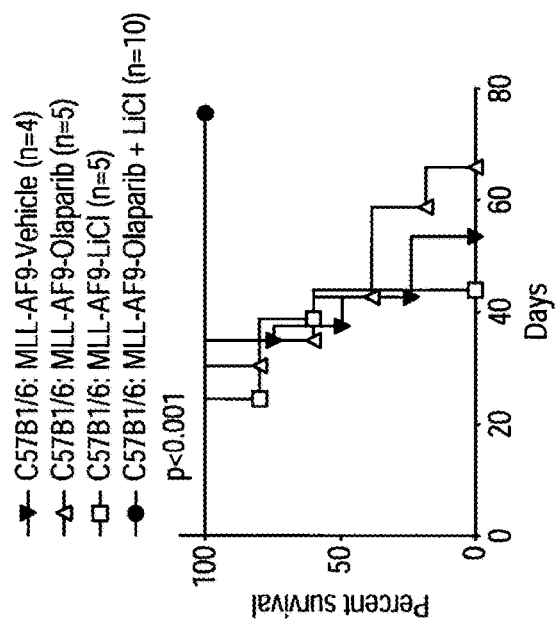
Figure 6I:
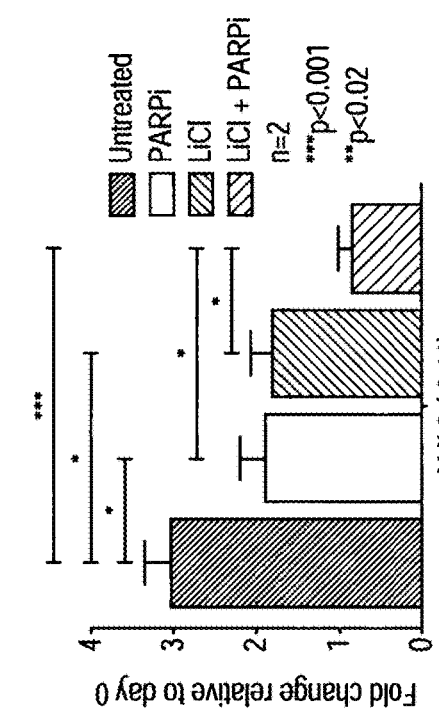
Figure 6K:
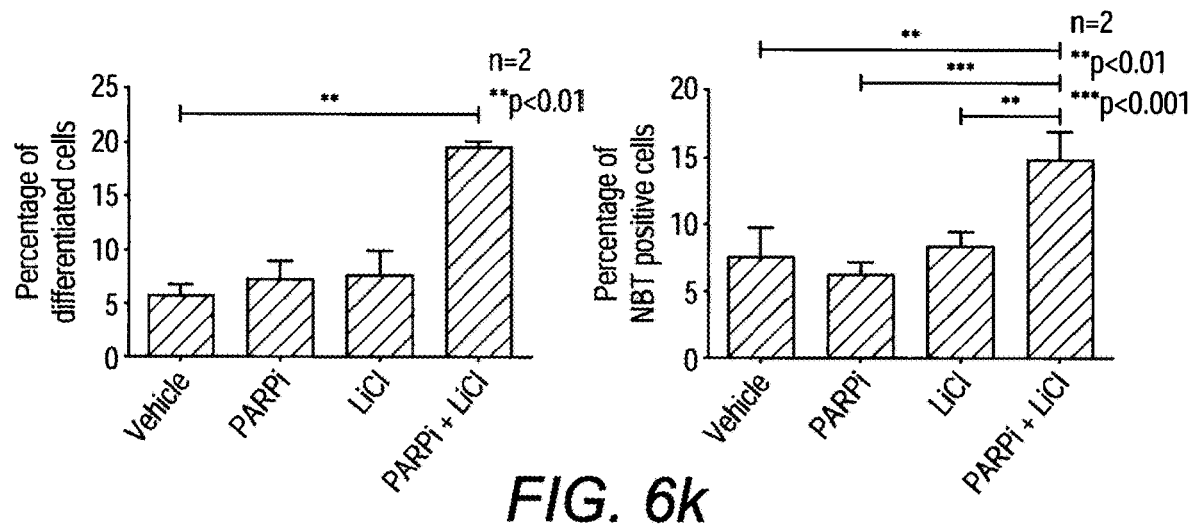
Figure 12A:
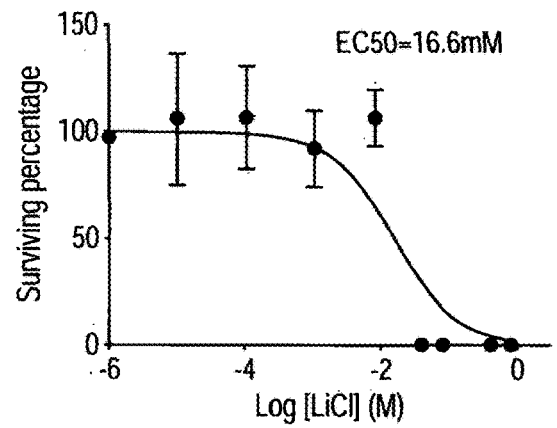
Figure 12B:
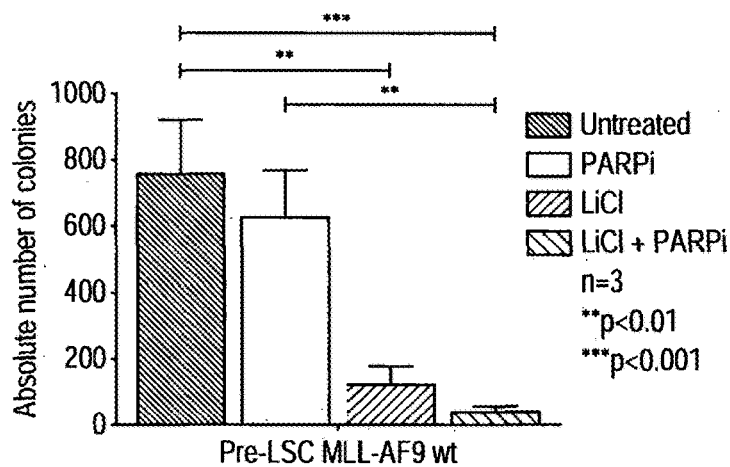
Figure 12C:
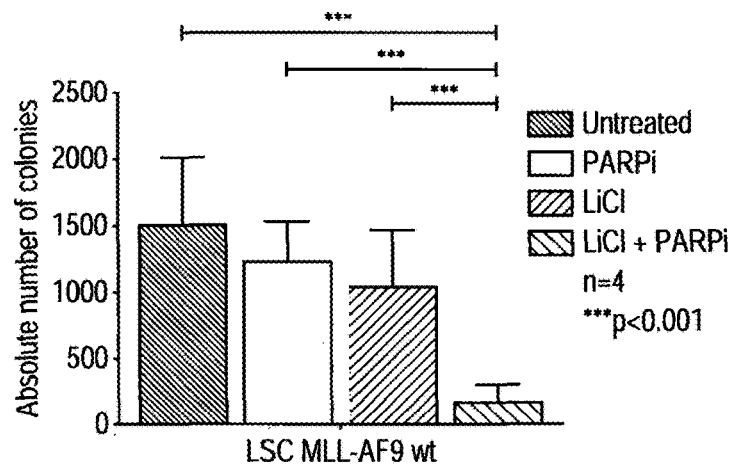
Figure 12D:
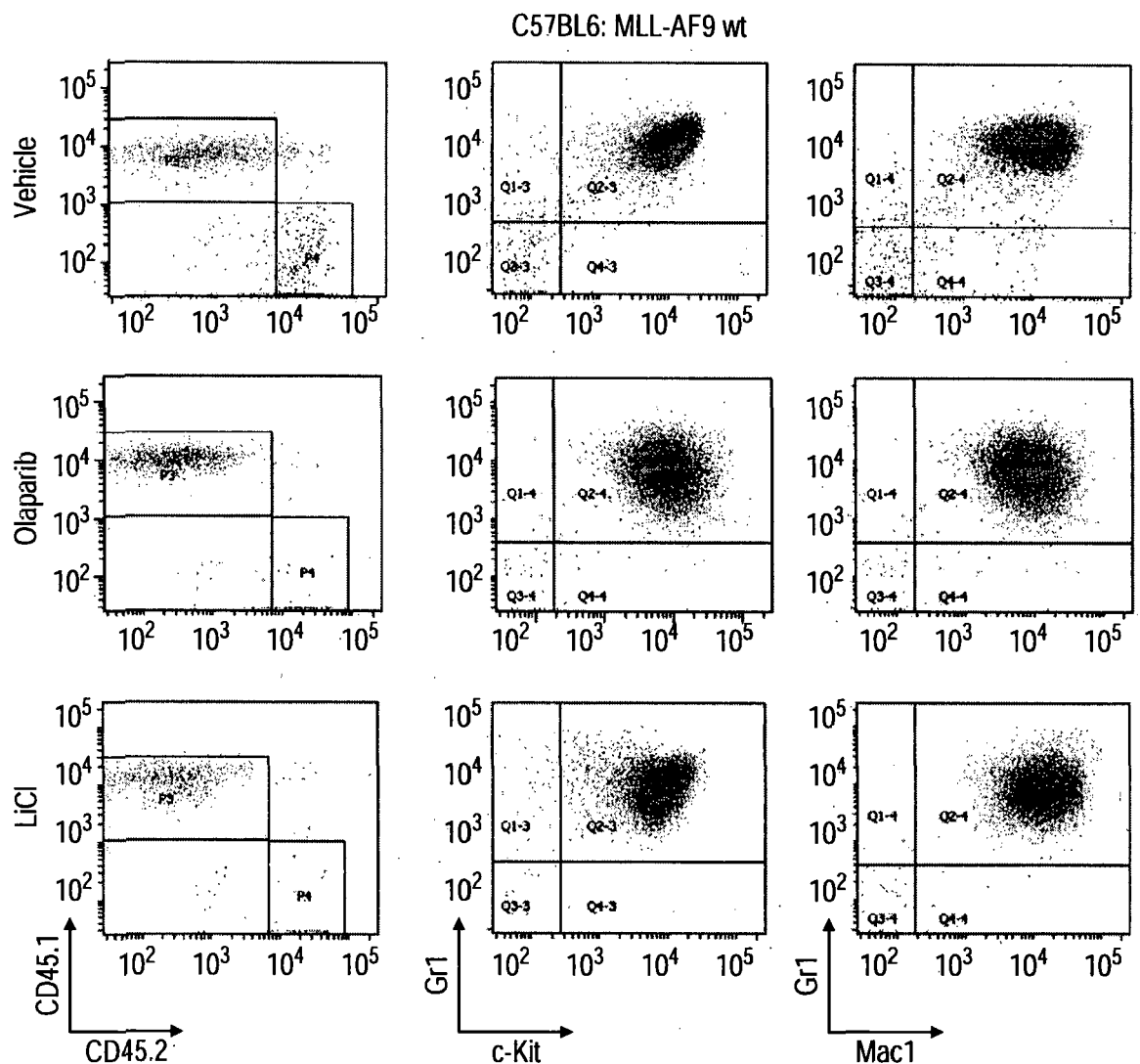
Figure 12E:
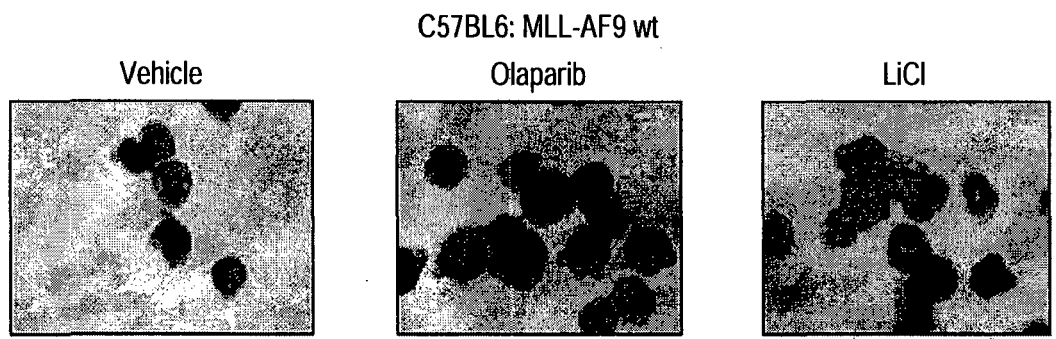

While there is not yet chemical inhibitor that can directly target Hoxa9, inhibitors are available to target its upstream regulators and essential co-factors, including GSK3, which mediates the phosphorylation of CREB/CBP required for Hox transcriptional functions[46]. We and others have previously shown that GSK3 inhibitor (GSKi) such as LiCl and LiCO3 were effective in suppressing the transcriptional activity of Hox and targeting MLL pre-leukemic stem cells (pre-LSC), but not the advanced stage MLL LSC that acquired resistance in part due to the activation of canonical Wnt/β-catenin pathways and were capable of inducing leukemia with a much shorter latency[22,46,47]. To further explore the potential application of PARPi on MLL leukemia, we assessed the effect of PARPi in combination with GSK3i (LiCl), on both MLL pre-LSC and MLL LSC enriched populations that exhibited contrasting GSKi sensitivity and disease latency[22]. As expected, the application of previously defined optimal concentration of LiCl (FIG. 12a)[22,46,47] significantly suppressed the colony forming ability of MLL pre-LSC, but not MLL LSC (FIG. 6a, c, and FIG. 12b-c). Interestingly, its combination with otherwise non-effective PARPi treatment led to further increased growth inhibition (FIG. 6a, c), which inversely correlated with transcriptional activity of Hoxa9 as assessed by the expression of its downstream target, c-myb (FIG. 6b, d). More strikingly, while individual PARPi or LiCl treatment was ineffective on MLL LSC, their combination dramatically suppressed leukemic cell growth and induced differentiation of MLL LSC (FIG. 6c, e, f). To further demonstrate the in vivo efficacy, pretreated MLL LSC were transplanted into syngeneic mice, and subjected to Olaparib, LiCO3, or their combined treatments (FIG. 6g). As expected, mice transplanted with control MLL-AF9 cells succumbed to leukemia within 8 weeks (FIG. 6g, FIG. 12d-e, and Table S7). PARPi or GSK3i treatment alone did not significantly extend the survival (FIG. 6g, FIG. 12d-e, and Table S7). Strikingly, the combined PARPi and GSK3i treatment suppressed leukemia development and all the mice still survived within the 80 days of observation period (FIG. 6g, FIG. 12d-e, and Table S7), highlighting the therapeutic potential of the novel combined treatment for MLL leukemia.

Figure 6L:
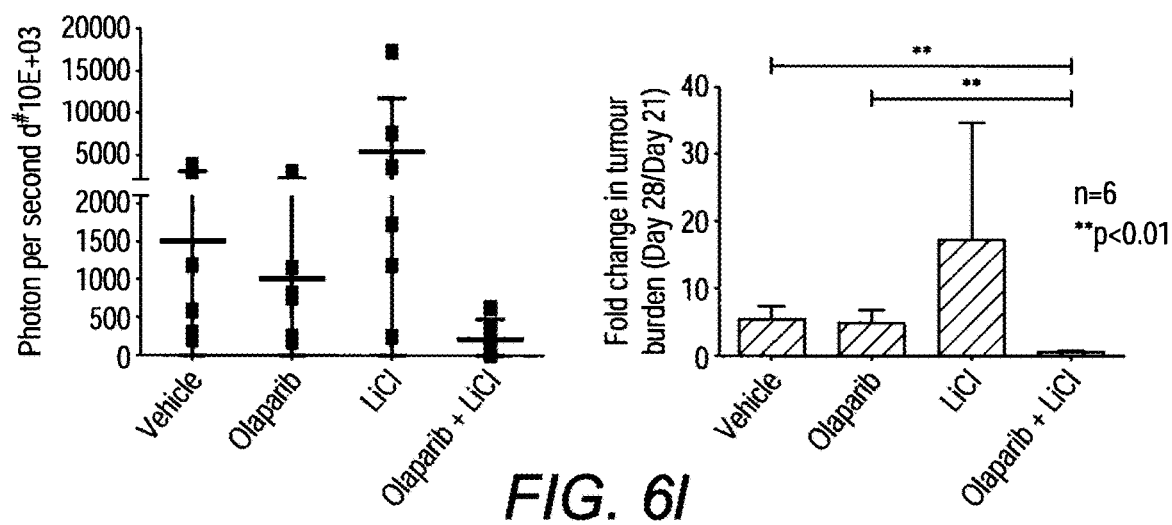
Figure 6M:
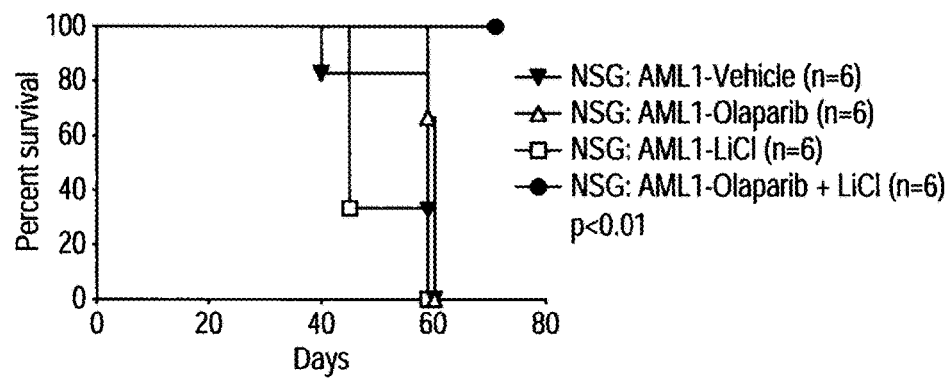
Figure 7B:
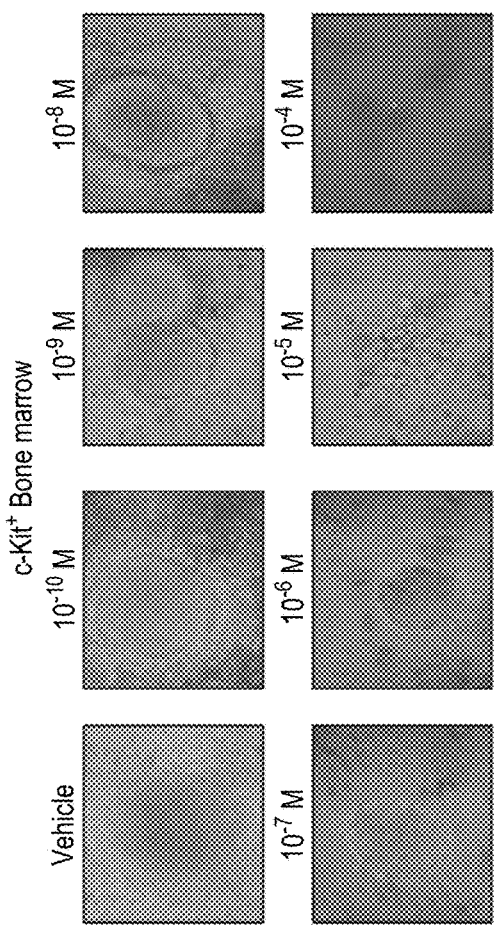
Figure 7D:
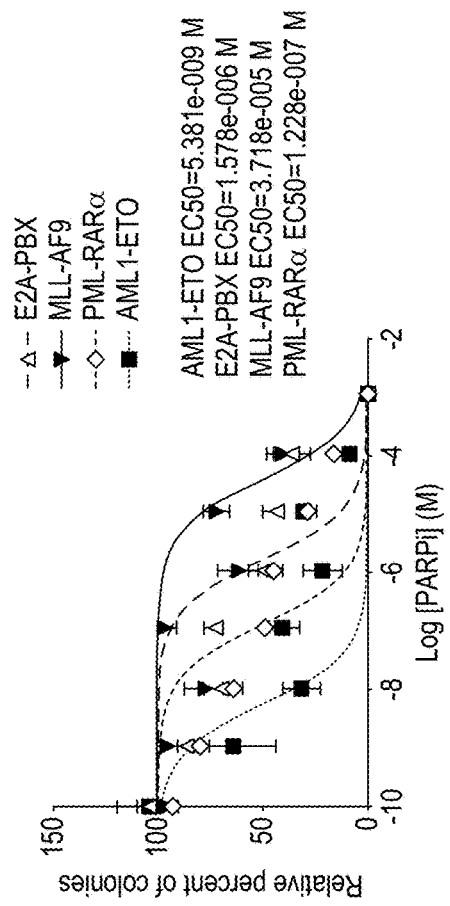
Figure 7A:
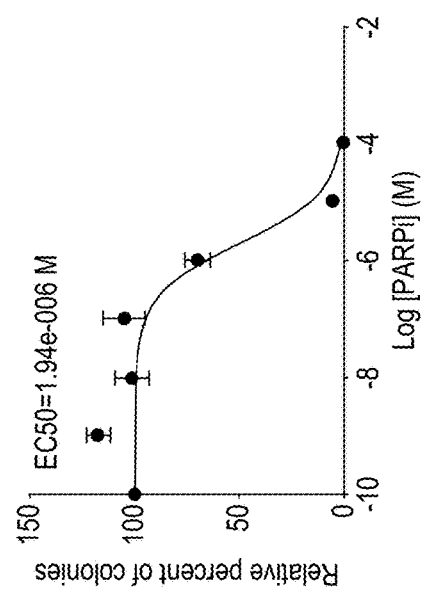
Figure 7C:
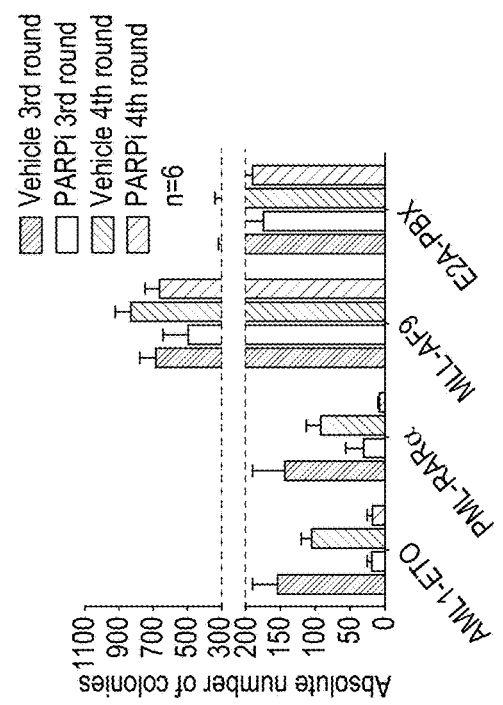
Figure 7I:
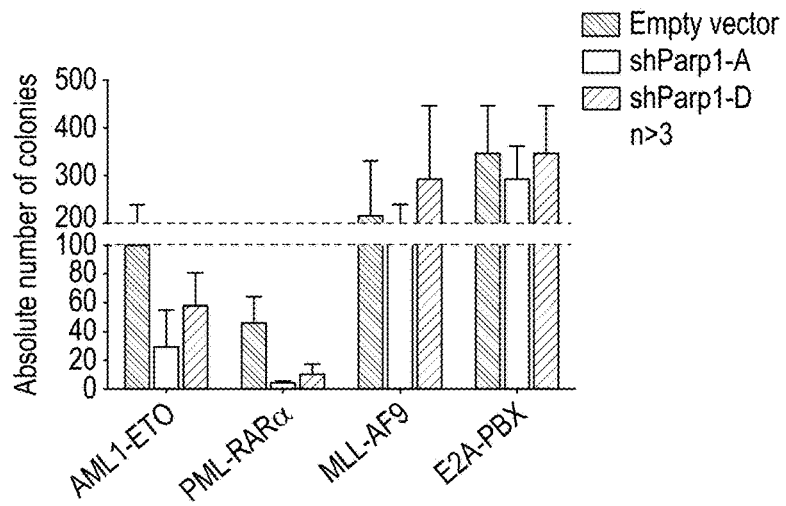
Figure 7J:
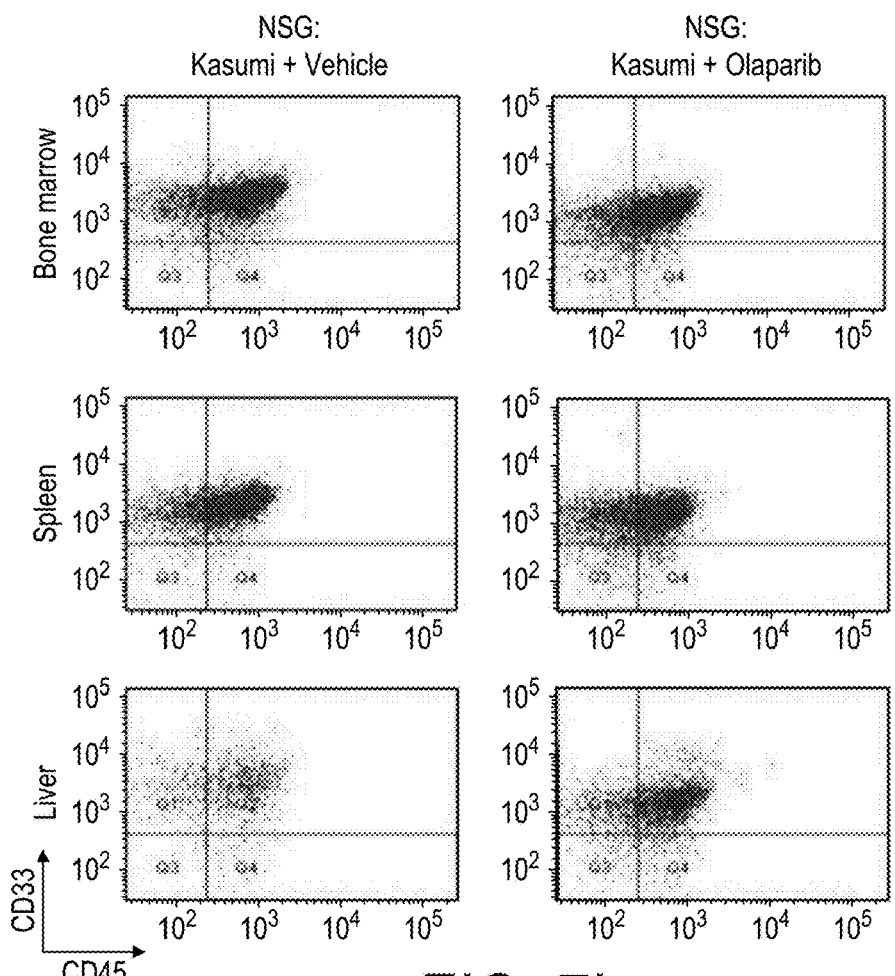
Figure 7I:
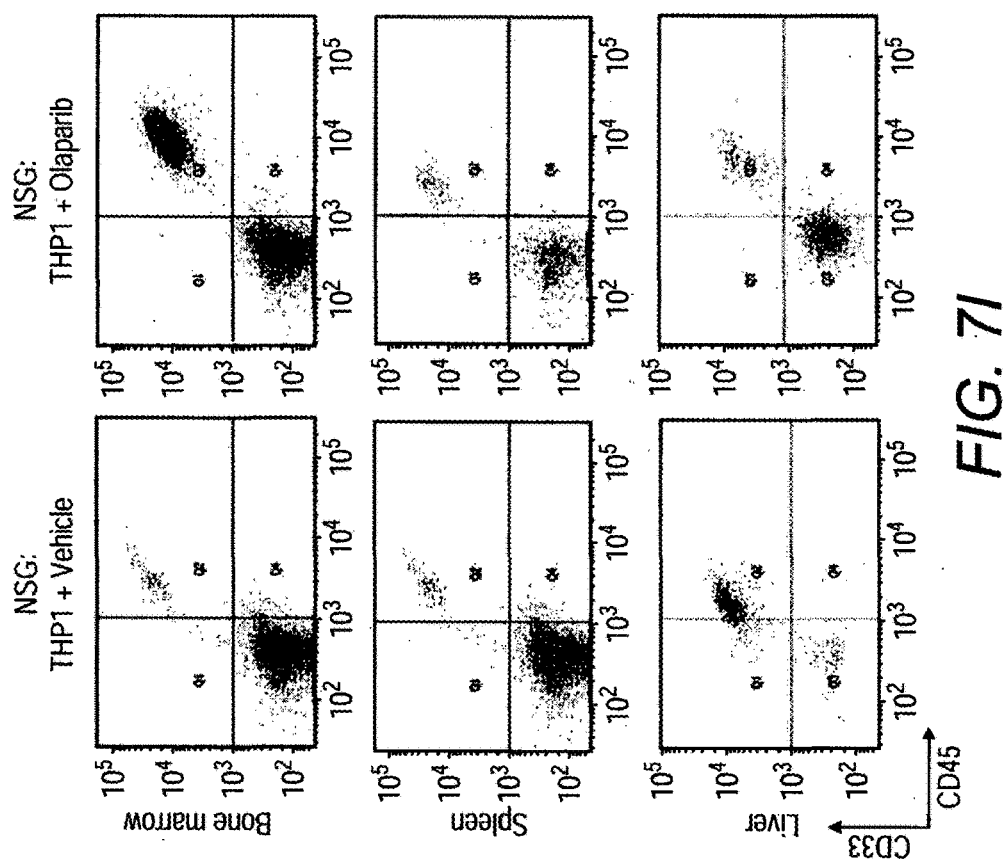
Figure 7K:
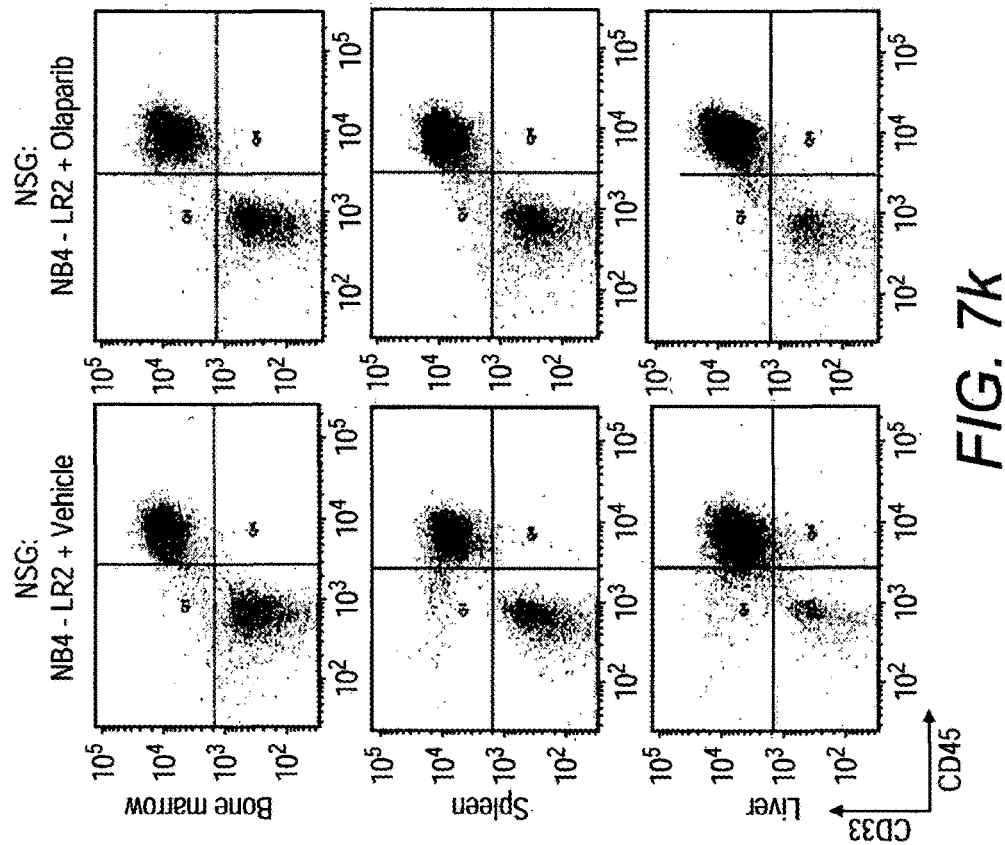
Figure 12F:
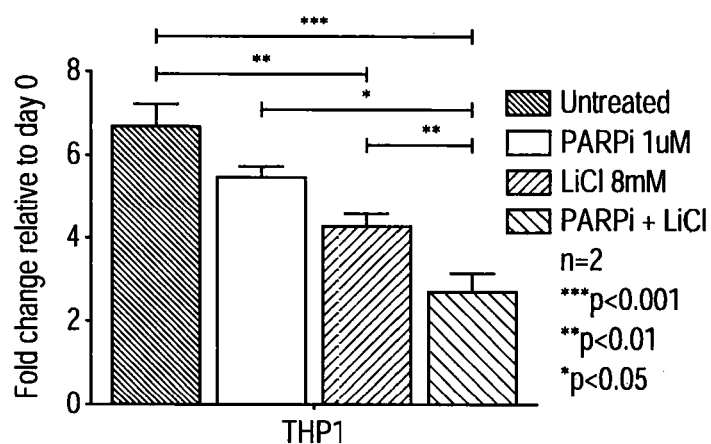
Figure 12G:
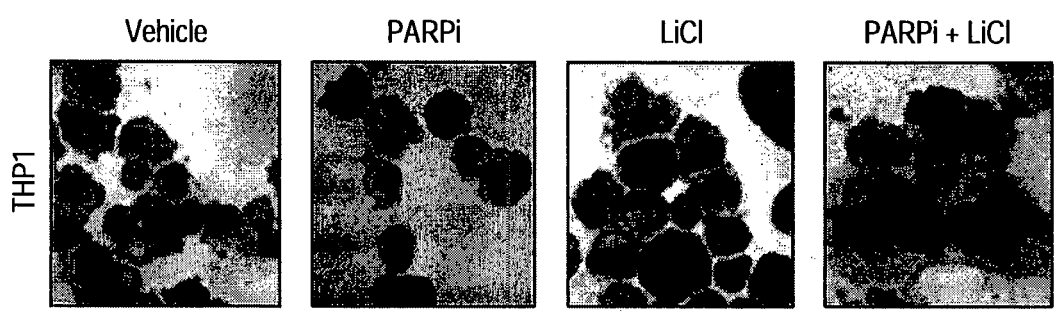
Figure 12H:
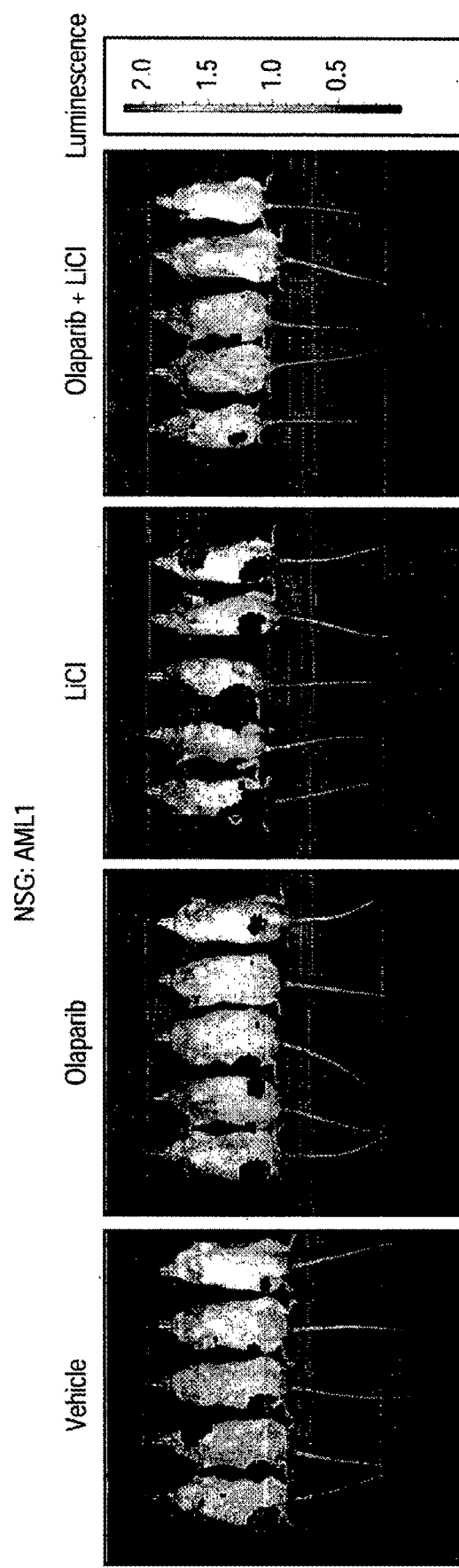
Figure 12I:
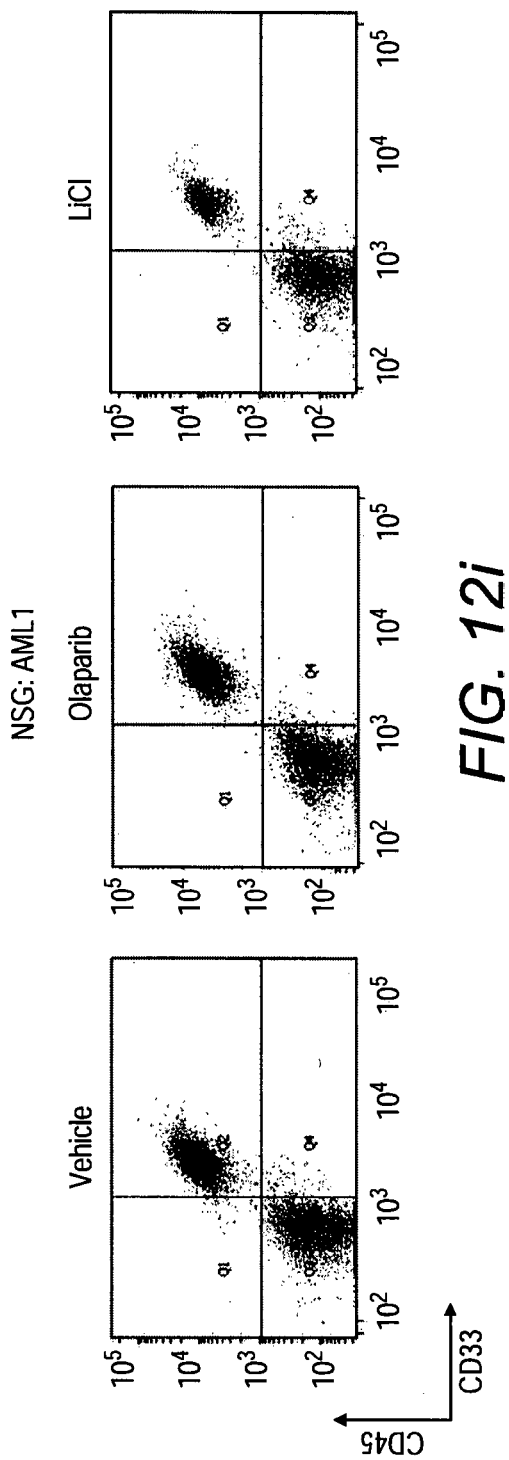
Figure 12J:
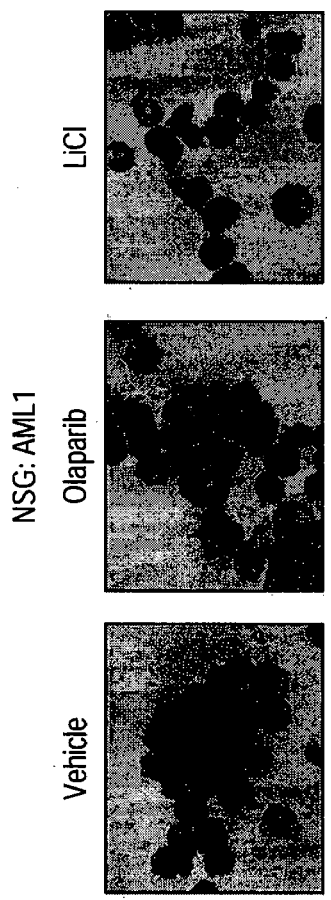

To investigate if a similar treatment could also be effective in the corresponding human leukemia, THP1 cells derived from the patient with MLL-AF9 fusion were also tested. As expected, Olaparib alone was ineffective and only modest suppression was observed with LiCl treatment (FIG. 12f-g). However in combination, LiCl could sensitize PARPi-resistant THP1 cells to the PARPi treatment resulting in significant growth suppression and differentiation of the leukemic cells (FIG. 12f-g). To further strengthen our findings in the relevant clinical setting, we performed the same treatments on two independent primary human patient samples carrying MLL fusions (i.e., patients AML1 and AML2). While limited inhibition was exhibited by individual treatments, their combination showed consistent and significant synergistic effects in suppressing growth and promoting differentiation of both primary MLL leukemic cells (FIG. 6h-k). Finally, to monitor and further demonstrate the in vivo treatment efficacy in primary, we labelled the primary MLL leukemic cells from patient AML1 with a luciferase reporter prior their transplantation into NSG mice for drug treatments. By in vivo imaging, we observed a rapid disease development as early as 4 weeks post-transplant in the untreated control (FIG. 6l, FIG. 12h). A similar rate of disease progression was also observed in cohorts receiving single drug treatments although LiCO3 treated group might exhibit an even faster rate of leukemic growth (FIG. 6l, FIG. 12h). In contrast, PARPi/LiCO3 combination treatment significantly prohibited leukemic cell growth in vivo (FIG. 6l, FIG. 12h). Following the long-term disease development, mice received single drug treatment succumbed to leukemia with a similar phenotype and disease latency as the control group (FIG. 6m, FIG. 12i-j, Table S8). Strikingly, the combination treatment significantly suppressed leukemia development and none of the tested subjects succumbed to leukemia throughout the observation period (FIG. 6m, FIG. 12i-j). Together, these independent results from mouse models and primary human xenograft models provide the first proof-of-principle pre-clinic evidence for a novel effective therapeutic strategy based on a combined PARPi and GSK3i treatment for MLL leukemia.

Discussion

In spite of the lack of genetic mutations directly affecting DDR genes, we provide molecular evidence and preclinical data showing the potential utility of PARPi-mediated selective killing of leukemic cells carrying specific oncogenic transcription factors (FIG. 13). This appears to be due to the differential impacts on these transcription factors on the expression of critical DDR genes involved DDR[48,52]. In addition to the discovery of strong PARPi sensitivity exhibited by AML1-ETO and PML-RARα transformed cells, we also demonstrate for the first time that Hoxa9, an independent poor prognostic factor in AML[38] and a key downstream target of MLL-fusions[53], can activate a potential back-up DDR pathway, which may allow leukemia cells to overcome PARPi. This finding may also in part explain the previously reported S-phase checkpoint dysfunction of MLL-rearranged leukemic cells showing radio-resistant DNA synthesis and chromatid-type genomic abnormalities[54].

Emerging evidence suggests that various Hox proteins may be involved in DNA repair[55,56]. HoxB7 interacts directly with PARP-1 and the complex DNA-PK-Ku80-Ku70 enabling NHEJ pathway[55], whereas HoxB9 promotes HR by inducing TGFβ, which in turn enhances ATM activation and ATM-dependent response in breast cancer cell lines56. Our data indicate that Hoxa9 mediates expression of critical DDR genes to stimulate HR and recruitment of Rad51 to DNA damage foci in response to PARPi treatment. Consistent with its putative role in mediating drug resistant in glioma[43,44], we further demonstrate that Hoxa9 over-expression rescues AML1-ETO and PML-RARα cells from PARPi treatment, whereas Hoxa9 KO makes MLL-AF9 sensitive to PARPi, revealing a novel function of Hoxa9 as a major player in governing PARPi resistance in MLL leukemia.

In line with a classical model of DDR barrier in cancer development[57], a recent study by Takacova et al. demonstrated that inactivation of the DDR barrier through ATM/ATR inhibitors accelerated leukemia driven by a tamoxifen-inducible MLL fusion[58]. On the other hand, Santos et al. have elegantly shown that total genetic ablation of critical DDR genes such as MLL4, ATM or BRCA1, instead of accelerating, inhibited MLL-driven leukemogenesis by inducing leukemic differentiation[59]. These results suggest dual roles of some of the key DDR players such as ATM in promoting and suppressing MLL leukemia, which may be dosage and context dependent. Interestingly, Hoxa9 that predominately drives leukemic growth and PARPi resistance is largely dispensable for normal development[23,42,60], highlighting its potential as a therapeutic target. As a proof-of-principle experiment, we further demonstrate that the combined use of PARPi together with the GSK3i that targeted the transcriptional function of Hoxa9[22,46,47] can achieve selective killing of otherwise PARPi-resistant MLL leukemic cells, revealing a potentially novel venue for overcoming PARPi-resistance in leukemia (FIG. 13).

Summary

Acute myeloid leukemia (AML) is mostly driven by oncogenic transcription factors, which have been classically viewed as intractable targets using small molecule inhibitor approaches. Here, we demonstrate that AML driven by repressive transcription factors including AML1-ETO and PML-RARα are extremely sensitive to Poly (ADP-ribose) Polymerase (PARP) inhibitor (PARPi), in part due to their suppressed expression of key homologous recombination genes and thus compromised DNA damage response (DDR). In contrast, leukemia driven by MLL fusions with dominant transactivation ability is proficient in DDR and insensitive to PARP inhibition. Intriguing, depletion of an MLL downstream target, Hoxa9 that activates expression of various HR genes, impairs DDR and sensitizes MLL leukemia to PARPi. Conversely, Hoxa9 over-expression confers PARPi resistance to AML1-ETO and PML-RARα transformed cells. Together, these studies describe a potential utility of PARPi-induced synthetic lethality for leukemia treatment and reveal a novel molecular mechanism governing PARPi sensitivity in AML.

REFERENCES

1. Krishnakumar, R. & Kraus, W. L. The PARP side of the nucleus: molecular actions, physiological outcomes, and clinical targets. *Mol Cell* 39, 8-24 (2010).
2. McLornan, D. P., List, A. & Mufti, G. J. Applying synthetic lethality for the selective targeting of cancer. *N Engl J Med* 371, 1725-1735 (2014).
3. De Lorenzo, S. B., Patel, A. G., Hurley, R. M. & Kaufmann, S. H. The Elephant and the Blind Men:

Making Sense of PARP Inhibitors in Homologous Recombination Deficient Tumor Cells. *Frontiers in oncology* 3, 228 (2013).
4. Helleday, T. The underlying mechanism for the PARP and BRCA synthetic lethality: clearing up the misunderstandings. *Mol Oncol* 5, 387-393 (2011).
5. El-Khamisy, S. F., Masutani, M., Suzuki, H. & Caldecott, K. W. A requirement for PARP-1 for the assembly or stability of XRCC1 nuclear foci at sites of oxidative DNA damage. *Nucleic Acids Res* 31, 5526-5533 (2003).
6. Masson, M., et al. XRCC1 is specifically associated with poly(ADP-ribose) polymerase and negatively regulates its activity following DNA damage. *Mol Cell Biol* 18, 3563-3571 (1998).
7. Bryant, H. E., et al. PARP is activated at stalled forks to mediate Mre11-dependent replication restart and recombination. *EMBO J* 28, 2601-2615 (2009).
8. Haince, J. F., et al. PARP1-dependent kinetics of recruitment of MRE11 and NBS1 proteins to multiple DNA damage sites. *J Biol Chem* 283, 1197-1208 (2008).
9. Haince, J. F., et al. Ataxia telangiectasia mutated (ATM) signaling network is modulated by a novel poly(ADP-ribose)-dependent pathway in the early response to DNA-damaging agents. *J Biol Chem* 282, 16441-16453 (2007).
10. Paddock, M. N., et al. Competition between PARP-1 and Ku70 control the decision between high-fidelity and mutagenic DNA repair. *DNA repair* 10, 338-343 (2011).
11. Roy, R., Chun, J. & Powell, S. N. BRCA1 and BRCA2: different roles in a common pathway of genome protection. *Nat Rev Cancer* 12, 68-78 (2012).
12. Carreira, A., et al. The BRC repeats of BRCA2 modulate the DNA-binding selectivity of RAD51. *Cell* 136, 1032-1043 (2009).
13. Fong, P. C., et al. Inhibition of poly(ADP-ribose) polymerase in tumors from BRCA mutation carriers. *N Engl J Med* 361, 123-134 (2009).
14. Tutt, A., et al. Oral poly(ADP-ribose) polymerase inhibitor olaparib in patients with BRCA1 or BRCA2 mutations and advanced breast cancer: a proof-of-concept trial. *Lancet* 376, 235-244 (2010).
15. Bryant, H. E., et al. Specific killing of BRCA2-deficient tumours with inhibitors of poly(ADP-ribose) polymerase. *Nature* 434, 913-917 (2005).
16. Farmer, H., et al. Targeting the DNA repair defect in BRCA mutant cells as a therapeutic strategy. *Nature* 434, 917-921 (2005).
17. Helleday, T., Petermann, E., Lundin, C., Hodgson, B. & Sharma, R. A. DNA repair pathways as targets for cancer therapy. *Nat Rev Cancer* 8, 193-204 (2008).
18. Esposito, M. T. & So, C. W. DNA damage accumulation and repair defects in acute myeloid leukemia: implications for pathogenesis, disease progression, and chemotherapy resistance. *Chromosoma* (2014).
19. Cheung, N. & So, C. W. Transcriptional and epigenetic networks in haematological malignancy. *FEBS Lett* 585, 2100-2111 (2011).
20. Zeisig, B. B., Kulasekararaj, A. G., Mufti, G. J. & So, C. W. Acute Myeloid Leukemia: Snapshot. *Cancer Cell* 22, 698 (2012).
21. Zeisig, B. B. & So, C. W. Retroviral/Lentiviral transduction and transformation assay. *Methods Mol Biol* 538, 207-229 (2009).
22. Yeung, J., et al. beta-Catenin mediates the establishment and drug resistance of MLL leukemic stem cells. *Cancer Cell* 18, 606-618 (2010).
23. Smith, L. L., et al. Functional crosstalk between Bmi1 and MLL/Hoxa9 axis in establishment of normal hematopoietic and leukemic stem cells. *Cell Stem Cell* 8, 649-662 (2011).
24. Arteaga, M. F., et al. The histone demethylase PHF8 governs retinoic acid response in acute promyelocytic leukemia. *Cancer Cell* 23, 376-389 (2013).
25. Fung, T. K. & So, C. W. Overcoming treatment resistance in acute promyelocytic leukemia and beyond. *Oncotarget* 4, 1128-1129 (2013).
26. Santos, M. A., et al. DNA-damage-induced differentiation of leukaemic cells as an anticancer barrier. *Nature* 514, 107-111 (2014).
27. Turner, N., Tutt, A. & Ashworth, A. Hallmarks of 'BRCAness' in sporadic cancers. *Nat Rev Cancer* 4, 814-819 (2004).
28. Kraus, W. L. Transcriptional control by PARP-1: chromatin modulation, enhancer-binding, coregulation, and insulation. *Curr Opin Cell Biol* 20, 294-302 (2008).
29. Mah, L. J., El-Osta, A. & Karagiannis, T. C. gammaH2AX: a sensitive molecular marker of DNA damage and repair. *Leukemia* 24, 679-686 (2010).
30. Baumann, P., Benson, F. E. & West, S. C. Human Rad51 protein promotes ATP-dependent homologous pairing and strand transfer reactions in vitro. *Cell* 87, 757-766 (1996).
31. Moynahan, M. E. & Jasin, M. Mitotic homologous recombination maintains genomic stability and suppresses tumorigenesis. *Nature reviews. Molecular cell biology* 11, 196-207 (2010).
32. Valk, P. J., et al. Prognostically useful gene-expression profiles in acute myeloid leukemia. *N Engl J Med* 350, 1617-1628 (2004).
33. Verhaak, R. G., et al. Prediction of molecular subtypes in acute myeloid leukemia based on gene expression profiling. *Haematologica* 94, 131-134 (2009).
34. Gaymes, T. J., Mufti, G. J. & Rassool, F. V. Myeloid leukemias have increased activity of the nonhomologous end-joining pathway and concomitant DNA misrepair that is dependent on the Ku70/86 heterodimer. *Cancer Res* 62, 2791-2797 (2002).
35. Pierce, A. J., Johnson, R. D., Thompson, L. H. & Jasin, M. XRCC3 promotes homology-directed repair of DNA damage in mammalian cells. *Genes Dev* 13, 2633-2638 (1999).
36. Yip, B. H. & So, C. W. Mixed lineage leukemia protein in normal and leukemic stem cells. *Exp Biol Med (Maywood)* 238, 315-323 (2013).
37. Krivtsov, A. V. & Armstrong, S. A. MLL translocations, histone modifications and leukaemia stem-cell development. *Nat Rev Cancer* 7, 823-833 (2007).
38. Golub, T. R., et al. Molecular classification of cancer: class discovery and class prediction by gene expression monitoring. *Science* 286, 531-537 (1999).
39. Costa, B. M., et al. Reversing HOXA9 oncogene activation by PI3K inhibition: epigenetic mechanism and prognostic significance in human glioblastoma. *Cancer Res* 70, 453-462 (2010).
40. Gaspar, N., et al. MGMT-independent temozolomide resistance in pediatric glioblastoma cells associated with a PI3-kinase-mediated HOX/stem cell gene signature. *Cancer Res* 70, 9243-9252 (2010).
41. Kumar, A. R., et al. Hoxa9 influences the phenotype but not the incidence of Mll-AF9 fusion gene leukemia. *Blood* 103, 1823-1828 (2004).
42. So, C. W., Karsunky, H., Wong, P., Weissman, I. L. & Cleary, M. L. Leukemic transformation of hematopoietic progenitors by MLL-GAS7 in the absence of Hoxa7 or Hoxa9. *Blood* 103, 3192-3199 (2004).
43. So, C. W., et al. MLL-GAS7 transforms multipotent hematopoietic progenitors and induces mixed lineage leukemias in mice. *Cancer Cell* 3, 161-171 (2003).
44. Faber, J., et al. HOXA9 is required for survival in human MLL-rearranged acute leukemias. *Blood* 113, 2375-2385 (2009).
45. Huang, Y., et al. Identification and characterization of Hoxa9 binding sites in hematopoietic cells. *Blood* 119, 388-398 (2012).
46. Wang, Z., et al. GSK-3 promotes conditional association of CREB and its coactivators with MEIS1 to facilitate HOX-mediated transcription and oncogenesis. *Cancer Cell* 17, 597-608 (2010).
47. Wang, Z., et al. Glycogen synthase kinase 3 in MLL leukaemia maintenance and targeted therapy. *Nature* 455, 1205-1209 (2008).
48. Viale, A., et al. Cell-cycle restriction limits DNA damage and maintains self-renewal of leukaemia stem cells. *Nature* 457, 51-56 (2009).
49. Boichuk, S., Hu, L., Makielski, K., Pandolfi, P. P. & Gjoerup, O. V. Functional connection between Rad51 and PML in homology-directed repair. *PLoS One* 6, e25814 (2011).
50. Yeung, P. L., et al. Promyelocytic leukemia nuclear bodies support a late step in DNA double-strand break repair by homologous recombination. *J Cell Biochem* (2011).
51. Zhong, S., et al. A role for PML and the nuclear body in genomic stability. *Oncogene* 18, 7941-7947 (1999).
52. Alcalay, M., et al. Acute myeloid leukemia fusion proteins deregulate genes involved in stem cell maintenance and DNA repair. *J Clin Invest* 112, 1751-1761 (2003).
53. Armstrong, S. A., et al. MLL translocations specify a distinct gene expression profile that distinguishes a unique leukemia. *Nat Genet* 30, 41-47 (2002).
54. Liu, H., et al. Phosphorylation of MLL by ATR is required for execution of mammalian S-phase checkpoint. *Nature* 467, 343-346 (2010).
55. Rubin, E., et al. A role for the HOXB7 homeodomain protein in DNA repair. *Cancer Res* 67, 1527-1535 (2007).
56. Chiba, N., et al. Homeobox B9 induces epithelial-to-mesenchymal transition-associated radioresistance by accelerating DNA damage responses. *Proc Natl Acad Sci USA* 109, 2760-2765 (2012).
57. Blanpain, C., Mohrin, M., Sotiropoulou, P. A. & Passegue, E. DNA-damage response in tissue-specific and cancer stem cells. *Cell Stem Cell* 8, 16-29 (2011).
58. Takacova, S., et al. DNA Damage Response and Inflammatory Signaling Limit the MLL-ENL-Induced Leukemogenesis In Vivo. *Cancer Cell* 21, 517-531 (2012).
59. Santos, M. A., et al. DNA-damage-induced differentiation of leukaemic cells as an anticancer barrier. *Nature* (2014).
60. Lawrence, H. J., et al. Loss of expression of the Hoxa-9 homeobox gene impairs the proliferation and repopulating ability of hematopoietic stem cells. *Blood* 106, 3988-3994 (2005).
61. Yeung, J. & So, C. W. Identification and characterization of hematopoietic stem and progenitor cell populations in mouse bone marrow by flow cytometry. *Methods Mol Biol* 538, 301-315 (2009).
62. Dimri, G. P., et al. A biomarker that identifies senescent human cells in culture and in aging skin in vivo. *Proc Natl Acad Sci USA* 92, 9363-9367 (1995).
63. Choi, E. J., Kim, S. M., Song, K. J., Lee, J. M. & Kee, S. H. Axin1 expression facilitates cell death induced by aurora kinase inhibition through PARP activation. *J Cell Biochem* 112, 2392-2402 (2011).
64. Schmittgen, T. D. & Livak, K. J. Analyzing real-time PCR data by the comparative C(T) method. *Nat Protoc* 3, 1101-1108 (2008).
65. Gaymes, T. J., et al. Increased error-prone non homologous DNA end-joining—a proposed mechanism of chromosomal instability in Bloom's syndrome. *Oncogene* 21, 2525-2533 (2002).
66. Gautier, L., Cope, L., Bolstad, B. M. & Irizarry, R. A. affy—analysis of Affymetrix GeneChip data at the probe level. *Bioinformatics* 20, 307-315 (2004).
67. Martin, N., et al. Interplay between Homeobox proteins and Polycomb repressive complexes in p16INK(4)a regulation. *EMBO J* 32, 982-995 (2013).

All publications mentioned in the above specification are herein incorporated by reference. Various modifications and variations of the described embodiments of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed various modifications of the described modes for carrying out the invention which are obvious to those skilled in the art are intended to be within the scope of the following claims.

TABLE S1

Table, related to FIG. 1g, summarising the characteristics of NSG mice succumbed with Kasumi driven disease

|  | Vehicle (n = 6) | Olaparib (n = 5) | Normal* |
|---|---|---|---|
| Disease Latency (days; median) | 5S | 102 | N/A |
| Spleen (g) | 0.0873 ± 0.0409 | 0.1630 ± 0.1198 | 0.03997 ± 0.0056 |
| Liver (g) | 1.843 ± 0.1330 | 1.999 ± 0.3720 | 1.037 ± 0.1050 |
| BM Engraftment (%) | 49.22 ± 21.47 | 41.35 ± 27.73 | N/A |
| Hematopoietic Spleen Engraftment (%) | 39.84 ± 21.93 | 48.68 ± 33.71 | N/A |
| Hematopoietic Liver Engraftment (%) | 42.76 ± 30.9 | 41.68 ± 26.19 | N/A |
| CBC WBC ($10^9$/L) | 2.5 ± 0.8485 | 2.9 ± 2.832 | 5.238 ± 3.763 |
| CBC RBC ($10^{12}$/L) | 6.68 ± 0.396 | 6.835 ± 1.328 | 7.235 ± 0.8716 |
| CBC Platelets ($10^9$/L) | 349 ± 39.6 | 514.8 ± 245.2 | 467.9 ± 231.7 |

N/A: not applicable
*Normal: normal NSG mice. Data collected from 3 animals

TABLE S2

Table, relating to FIG. 1h, summarising the characteristics of NSG mice succumbed with NB4-LR2 driven disease

|  | Vehicle (n = 5) | Olaparib (n = 10) | Normal* |
|---|---|---|---|
| Disease Latency (days; median) | 39 | 51 | N/A |
| Spleen (g) | 0.1216 ± 0.0232 | 0.5226 ± 0.5279 | 0.03997 ± 0.0056 |
| Liver (g) | 2.26 ± 0.401 | 2.415 ± 1.844 | 1.037 ± 0.1050 |
| BM Engraftment (%) | 30.94 ± 23.11 | 40.27 ± 23.73 | N/A |
| Hematopoietic Spleen Engraftment (%) | 22.8 ± 25.13 | 33.39 ± 25.3 | N/A |
| Hematopoietic Liver Engraftment (%) | 47.64 ± 19.68 | 58.99 ± 27.07 | N/A |
| CBC WBC ($10^9$/L) | 3.875 ± 3.288 | 2.322 ± 1.177 | 5.238 ± 3.763 |
| CBC RBC ($10^{12}$/L) | 8.14 ± 3.857 | 7.576 ± 3.309 | 7.235 ± 0.8716 |
| CBC Platelets ($10^9$/L) | 442.3 ± 177.9 | 406.3 ± 43.46 | 467.9 ± 231.7 |

N/A: not applicable
*Normal: normal NSG mice. Data collected from 3 animals.

TABLE S3

Table, relating to FIG. 1i, summarising the characteristics of NSG mice succumbed with THP1 driven disease

|  | Vehicle (n = 6) | Olaparib (n = 6) | Normal |
|---|---|---|---|
| Disease Latency (days; median) | 81 | 81 | N/A |
| Spleen (g) | 0.108 ± 0.0146 | 0.0822 ± 0.0301 | 0.03997 ± 0.0056 |
| Liver (g) | 1.28 ± 0.147 | 1.31 ± 0.153 | 1.037 ± 0.1050 |
| BM Engraftment (%) | 3.266 ± 2.153 | 30.7 ± 33.27 | N/A |
| Hematopoietic Spleen Engraftment (%) | 8.831 ± 5.679 | 8.53 ± 6.946 | N/A |
| Hematopoietic Liver Engraftment (%) | 46.48 ± 43.05 | 27.81 ± 31.79 | N/A |
| CBC WBC ($10^9$/L) | 4.1 ± 3.69 | 6.18 ± 4.22 | 5.238 ± 3.763 |
| CBC RBC ($10^{12}$/L) | 7.653 ± 0.611 | 8.526 ± 1.575 | 7.235 ± 0.8716 |
| CBC Platelets ($10^9$/L) | 183.83 ± 70.25 | 132.2 ± 27.58 | 467.9 ± 231.7 |

N/A: not applicable
* Normal: normal NSG mice. Data collected from 3 animals.

TABLE S5

Table, relating to FIG. 4f, summarising the characteristics of C57bl6 mice succumbed with MLL-AF9 wild-type driven leukemia

|  | Vehicle (n = 12) | Olaparib (n = 12) | Normal* |
|---|---|---|---|
| Disease Latency (days; median) | 31 | 34 | N/A |
| Spleen (g) | 0.7968 ± 0.39 | 0.9309 ± 0.3767 | 0.1130 ± 0.03430 |
| Liver (g) | 3.486 ± 1.71 | 4.204 ± 1.425 | 1.331 ± 0.2650 |
| BM Engraftment (%) | 95.99 ± 5.054 | 93.30 ± 9.257 | N/A |
| Hematopoietic Spleen Engraftment (%) | 90.25 ± 8.872 | 86.85 ± 13.12 | N/A |
| Hematopoietic Liver Engraftment (%) | 94.22 ± 3.393 | 93.16 ± 6.838 | N/A |
| CBC WBC ($10^9$/L) | 26.87 ± 35.61 | 26.03 ± 34.48 | 19.32 ± 3.177 |
| CBC RBC ($10^{12}$/L) | 5.573 ± 0.7508 | 5.735 ± 3.426 | 8.620 ± 0.3385 |
| CBC Platelets ($10^9$/L) | 190 ± 68.02 | 203 ± 255.1 | 357.8 ± 83.54 |

N/A: not applicable
*Normal C57Bl6 mice: Data collected from 3 mice

TABLE S6

Figure 4G:
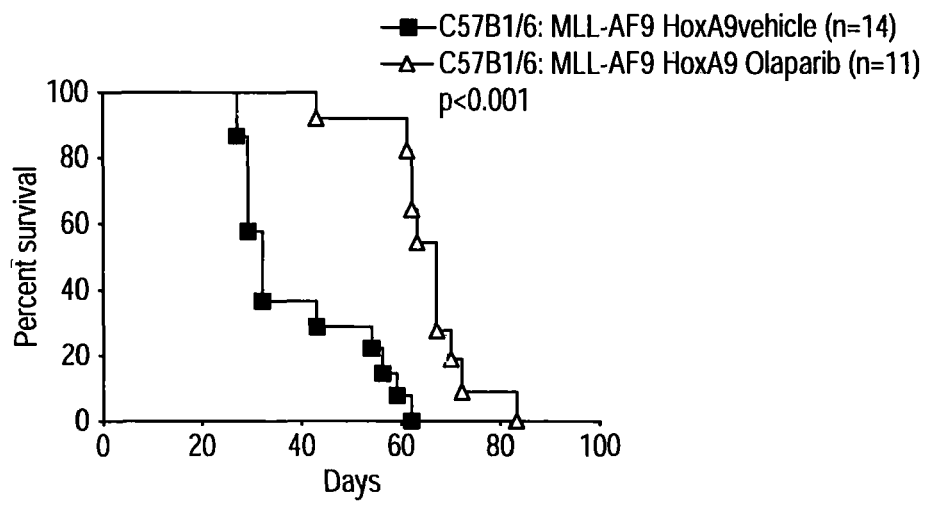
Figure 4H:
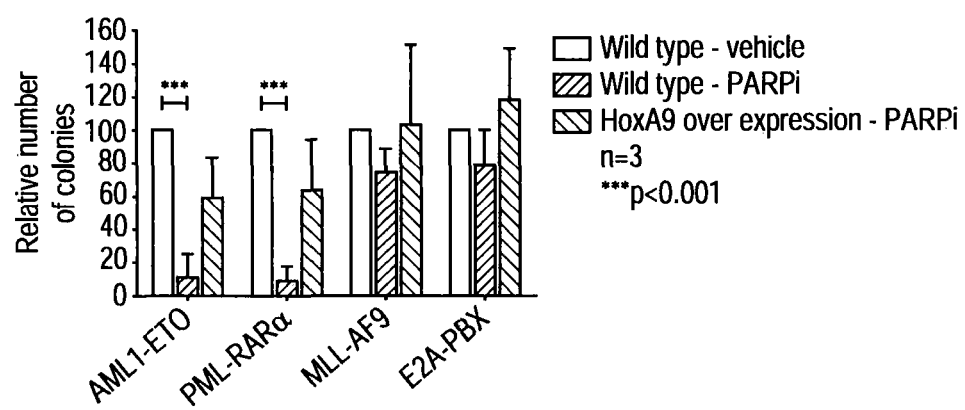

Table relating to FIG. 4g, summarising the characteristics of C57Bl6 mice succumbed with MLL-AF9-Hoxa9 KO driven leukemia

|  | Vehicle (n = 14) | Olaparib (n = 11) | Normal* |
|---|---|---|---|
| Disease Latency (days; median) | 32 | 67 | N/A |
| Spleen (g) | 0.5429 ± 0.1810 | 0.4337 ± 0.1559 | 0.1130 ± 0.03430 |
| Liver (g) | 2.127 ± 0.5528 | 1.696 ± 0.1262 | 1.331 ± 0.2650 |
| BM Engraftment (%) | 61.3 ± 28.64 | 82.06 ± 18.95 | N/A |
| Hematopoietic Spleen Engraftment (%) | 50.62 ± 33.78 | 65.4 ± 33.45 | N/A |
| Hematopoietic Liver Engraftment (%) | 64.02 ± 23.34 | 62.18 ± 38.26 | N/A |
| CBC WBC ($10^9$/L) | 41.4 ± 47.8 | 53.93 ± 51.06 | 19.32 ± 3.177 |
| CBC RBC ($10^{12}$/L) | 5.187 ± 1.95 | 4.153 ± 2.066 | 8.620 ± 0.3385 |
| CBC Platelets ($10^9$/L) | 223 ± 83.45 | 227 ± 166 | 357.8 ± 83.54 |

N/A: not applicable
*Normal C57Bl6 mice: Data collected from 3 mice

TABLE S4

Genes associated with GO:0000724: double-strand break repair via homologous recombination analysis enriched in gene ontology (GO) analysis of gene expression in human leukemia with MLL-rearrangement compared to APL and AML1-ETO subtypes (column 1) and HOXA9 responsive genes (column 2) in published datasets. Bolded are DDR genes commonly activated by MLL fusions and Hoxa9.

| MLL-rearrangement | HOXA9 |
|---|---|
| RAD51 | RAD51 |
| MCM9 | MCM9 |
| ATM | ATM |
| BLM | BLM |
| BRCA1 | BRCA1 |
| BRCA2 | BRCA2 |
| CHEK1 | CHEK1 |
| HUS1 | HUS1 |
| MRE11A | MRE11A |
| PARPBP | PARPBP |
| RAD51C | RAD51C |
| RPA1 | RPA1 |
| RAD50 | ERCC4 |
| MORF4L1 | NABP2 |
| TERF2IP | PPP4C |
| NBN | RAD21L1 |
| H2AFX | RAD51B |
| NABP2 | RAD51D |
| RBBP8 | RAD52 |
| MDC1 | RAD54B |
| RAD51AP1 | RTEL1 |
| PSMD14 | SIRT6 |
| PALB2 | SMC6 |
| RPA2 | TEX15 |
| LIG1 | TONSL |
| RPA3 | XRCC3 |
| SHFM1 | |
| SMC5 | |
| UBE2N | |
| YY1 | |

TABLE S7

Table, relating to FIG. 6g, summarising the characteristics of C57Bl6 mice succumbed with MLL-AF9 wild-type driven leukemia.

|  | Vehicle (n = 4) | Olaparib (n = 5) | LiCl (n = 5) | Olaparib + LiCl (n = 10) | Normal* |
|---|---|---|---|---|---|
| Disease Latency (days; median) | 41.5 | 45.8 | 38.2 | N/A** | N/A |
| Spleen (g) | 1.115 ± 0.3960 | 1.218 ± 0.3266 | 1.108 ± 0.4018 | N/A | 0.1130 ± 0.03430 |
| Liver (g) | 2.483 ± 0.4211 | 2.868 ± 0.4089 | 2.625 ± 0.6598 | N/A | 1.331 ± 0.2650 |
| BM Engraftment (%) | 95.03 ± 2.2937 | 80.23 ± 23.70 | 97.23 ± 1.408 | N/A | N/A |
| Hematopoietic Spleen Engraftment (%) | 86.47 ± 3.523 | 65.07 ± 43.46 | 91.28 ± 4.623 | N/A | N/A |
| Hematopoietic Liver Engraftment (%) | 92.97 ± 3.175 | 76.5 ± 19.21 | 93.73 ± 5.5508 | N/A | N/A |
| CBC WBC ($10^9$/L) | 26.87 ± 35.61 | 26.03 ± 34.48 | 24.03 ± 28.11 | N/A | 19.32 ± 3.177 |
| CBC RBC ($10^{12}$/L) | 5.573 ± 0.7508 | 5.735 ± 3.426 | 5.29 ± 2.578 | N/A | 8.620 ± 0.3385 |
| CBC Platelets ($10^9$/L) | 190 ± 68.02 | 203 ± 255.1 | 135.8 ± 89.68 | N/A | 357.8 ± 83.54 |

N/A: not applicable
*Normal C57Bl6 mice: Data collected from 5 mice
**No disease latency because no animal comes down with disease.

TABLE S8

Table, relating to FIG. 6m, summarising the characteristics of NSG mice succumbed to leukemia driven by primary AML1 cells treated with Olaparib, Li diet or combination therapy in vivo.

| | Vehicle (n = 6) | Olaparib (n = 6) | Li diet (n = 6) | Olaparib + Li diet (n = 6) | Normal* |
|---|---|---|---|---|---|
| Disease Latency (days; median) | 59 | 60 | 45 | N/A** | N/A |
| Spleen (g) | 0.076 ± 0.030 | 0.136 ± 0.029 | 0.133 ± 0.060 | N/A | 0.03997 ± 0.0056 |
| Liver (g) | 1.20 ± 0.157 | 1.30 ± 0.134 | 1.27 ± 0.091 | N/A | 1.037 ± 0.1050 |
| BM Engraftment (%) | 57.98 ± 30.49 | 53.23 ± 23.21 | 28.72 ± 15.19 | N/A | N/A |
| Hematopoietic Spleen Engraftment (%) | 11.30 ± 7.885 | 2.733 ± 4.166 | 1.760 ± 3.266 | N/A | N/A |
| Hematopoietic Liver Engraftment (%) | 42.65 ± 22.61 | 23.20 ± 20.61 | 16.93 ± 17.75 | N/A | N/A |
| CBC WBC ($10^9$/L) | 3.000 ± 2.160 | 3.950 ± 3.265 | 5.267 ± 7.450 | N/A | 5.238 ± 3.763 |
| CBC RBC ($10^{12}$/L) | 7.978 ± 0.659 | 6.652 ± 1.908 | 5.960 ± 2.003 | N/A | 7.235 ± 0.8716 |
| CBC Platelets ($10^9$/L) | 307.8 ± 160.9 | 393.2 ± 293.6 | 314.3 ± 274.1 | N/A | 467.9 ± 231.7 |

N/A: not applicable
*Normal NSG mice: Data collected from 6 mice
**No disease latency and engraftment data because no animal comes down with disease.

TABLE S9

List of antibodies (The antibodies provided as gift were mentioned in materials and methods).

| Antibody | Supplier | Catalog number | Application | Dilution |
|---|---|---|---|---|
| Actin-HRP | Scbt | Sc-1616 | Western Blot | 1:1000 |
| Phospho-γ H2AX (ser139) | Upstate | 05-636 | Immunofluorescence | 1:200 |
| Rad51 | Scbt | Sc-8349 | Western Blot | 1:500 |
| Rad51 | Scbt | Sc-8349 | Immunofluorescence | 1:100 |
| PARP1 | Cell signaling | #9542S | Western Blot | 1:1000 |
| FLAG (M2) | Sigma | F1804 | Western Blot | 1:5000 |
| | | | Immunoprecipitation | 1 ug |

The invention claimed is:

1. A method of treatment of mixed lineage leukaemia (MLL) subtype of acute myeloid leukaemia (AML) in a subject in need thereof, the method comprising administering to the subject a combination, in synergistically effective amounts, of
   (a) a poly-(ADP-ribose)-polymerase (PARP) inhibitor, wherein the PARP inhibitor comprises olaparib, veliparib, CEP-8983, rucaparib, E7016, BMN-673, INO-1001, iniparib, and analogues and derivatives thereof; and
   (b) a second agent comprising
      (i) an inhibitor of glycogen synthase kinase 3 (GSK-3), wherein the GSK-3 inhibitor comprises lithium or a salt thereof, SB216763, SB415286, or 6-bromo-indirubin-3'-oxime (6-BIO); or
      (ii) an inhibitor of disrupter of telomeric silencing 1-like (DOT1L), wherein the inhibitor of DOT1L comprises EPZ-5676 or EPZ-4777;
wherein the subject has a cytogenetic abnormality at chromosome 11q23 resulting in a rearranged MLL gene and/or expression of a MLL fusion protein.

2. The method according to claim 1, wherein the second agent comprises the inhibitor of GSK-3.

3. The method according to claim 2, wherein the GSK-3 inhibitor comprises lithium.

4. The method according to claim 1, wherein the second agent comprises the inhibitor DOT1L.

5. The method according to claim 1, wherein the PARP inhibitor is selected from olaparib, veliparib, CEP-8983, rucaparib, E7016, BMN-673 and INO-1001, and analogues and derivatives thereof.

6. A method for treatment of a subject suffering from mixed lineage leukaemia (MLL) subtype of acute myeloid leukaemia, comprising:
   identifying a chromosomal abnormality at 11q23 in the subject; and
   administering to the subject identified as having the chromosomal abnormality at 11q23 a therapy comprising combined administration, in synergistic amounts, of
   (a) a poly-(ADP-ribose)-polymerase (PARP) inhibitor, wherein the PARP inhibitor comprises olaparib, veliparib, CEP-8983, rucaparib, E7016, BMN-673, INO-1001, iniparib, and analogues and derivatives thereof; and
   (b) a second agent comprising
      (i) an inhibitor of glycogen synthase kinase 3 (GSK-3), wherein the GSK-3 inhibitor comprises lithium or a salt thereof, SB216763, SB415286, or 6-bromo-indirubin-3'-oxime (6-BIO); or
      (ii) an inhibitor of disrupter of telomeric silencing 1-like (DOT1L), wherein the inhibitor of DOT1L comprises EPZ-5676 or EPZ-4777.

7. The method according to claim 6, wherein the chromosomal abnormality at 11823 comprises a rearranged MLL gene and/or expression of a MLL fusion protein.

8. The method according to claim 6, wherein the second agent comprises the inhibitor of GSK-3.

9. The method according to claim 8, wherein the GSK-3 inhibitor comprises lithium.

10. The method according to claim 6 wherein the second agent comprises the inhibitor of DOT1L.

* * * * *

UNITED STATES PATENT AND TRADEMARK OFFICE
CERTIFICATE OF CORRECTION

PATENT NO. : 10,799,501 B2  
APPLICATION NO. : 15/773947  
DATED : October 13, 2020  
INVENTOR(S) : Chi Wai Eric So Page 1 of 1

It is certified that error appears in the above-identified patent and that said Letters Patent is hereby corrected as shown below:

At Column 15, Line 39, "06,444,676" should read --6,444,676--.

At Column 15, Line 51, "06,635,642" should read --6,635,642--.

At Column 15, Line 53, "US2005/6924284" should read --U.S. Pat. No. 6,924,284--.

At Column 15, Line 54, "US2004/6828319" should read --U.S. Pat. No. 6,828,319--.

At Column 15, Line 58, "05,587,384" should read --5,587,384--.

At Column 15, Line 66, "06,426,415" should read --6,426,415--.

At Column 15, Line 66, "06,476,048" should read --6,476,048--.

At Column 17, Line 41, "β and β" should read --α and β--.

At Column 31, Line 19, "5×103-1.5×104" should read --$5\times10^3$-$1.5\times10^4$--.

In Claim 7 at Column 54, Line 24, "11823" should read --11q23--.

Signed and Sealed this  
Second Day of March, 2021

Drew Hirshfeld  
*Performing the Functions and Duties of the  
Under Secretary of Commerce for Intellectual Property and  
Director of the United States Patent and Trademark Office*